United States Patent
Widdowson et al.

(10) Patent No.: US 11,471,539 B2
(45) Date of Patent: Oct. 18, 2022

(54) GENETIC CONSTRUCT

(71) Applicant: Quethera Limited, Canterbury (GB)

(72) Inventors: Peter Widdowson, Canterbury (GB); Keith Martin, Canterbury (GB)

(73) Assignee: QUETHERA LIMITED, Canterbury (GB)

( * ) Notice: Subject to any disclaimer, the term of this patent is extended or adjusted under 35 U.S.C. 154(b) by 656 days.

(21) Appl. No.: 16/436,676

(22) Filed: Jun. 10, 2019

(65) Prior Publication Data
US 2020/0040360 A1 Feb. 6, 2020

Related U.S. Application Data

(63) Continuation of application No. 15/762,089, filed as application No. PCT/GB2016/053319 on Oct. 25, 2016, now Pat. No. 10,342,880.

(30) Foreign Application Priority Data

Oct. 26, 2015 (GB) .................................... 1518911

(51) Int. Cl.
| | | |
|---|---|---|
| A61K 39/00 | (2006.01) | |
| A61K 48/00 | (2006.01) | |
| C12N 15/86 | (2006.01) | |
| A61B 3/032 | (2006.01) | |
| A61K 31/7088 | (2006.01) | |
| C07K 14/48 | (2006.01) | |
| C12N 15/864 | (2006.01) | |
| C12N 9/12 | (2006.01) | |
| A61P 27/02 | (2006.01) | |
| A61P 25/00 | (2006.01) | |
| A61K 38/18 | (2006.01) | |
| C12N 15/10 | (2006.01) | |
| C12N 15/62 | (2006.01) | |
| C12N 15/85 | (2006.01) | |
| A61K 38/00 | (2006.01) | |

(52) U.S. Cl.
CPC ........ *A61K 48/0066* (2013.01); *A61K 38/185* (2013.01); *A61K 48/0058* (2013.01); *A61P 25/00* (2018.01); *A61P 27/02* (2018.01); *C07K 14/48* (2013.01); *C12N 9/12* (2013.01); *C12N 15/1027* (2013.01); *C12N 15/62* (2013.01); *C12N 15/85* (2013.01); *C12N 15/86* (2013.01); *C12N 15/8645* (2013.01); *A61K 38/00* (2013.01); *A61K 48/00* (2013.01); *C12N 2750/14132* (2013.01); *C12N 2750/14143* (2013.01); *C12N 2830/008* (2013.01); *C12N 2840/203* (2013.01)

(58) Field of Classification Search
CPC ............ A61K 2300/00; A61K 31/7088; A61K 38/179; A61K 38/45; A61K 48/00
See application file for complete search history.

(56) References Cited

U.S. PATENT DOCUMENTS

2004/0110711 A1 6/2004 Krueger et al.
2011/0288160 A1 11/2011 During et al.

OTHER PUBLICATIONS

Cheng, L. et al., "TrkB gene transfer protects retinal ganglion cells from axotomy-induced death in vivo", 2002, J. Neurosci, vol. 22, No. 10, 3977-3986.*
Bai, et al., "An Agonistic TrkB mAb Causes Sustained TrkB Activation, Delays RGC Death, and Protects the Retinal Structure in Optic Nerve Axotomy and in Glaudoma", Investigative Ophthalmology & Visual Science, 2010, 51(9):4722-4731.
Chader, "Advances in Glaucoma Treatment and Management: Neurotrophic Agents", Investigative Ophthalmology & Visual Science, 2012, 53(5): 2501-2505.
Cheng et al., "TrkB Gene Transfer Protects Retinal Ganglion Cells from Axotomy-lnduced Death In Vivo", The Journal of Neuroscience, 2002, 22(10): 3977-3986.
Khalin et al., "Targeted delivery of brain-derived neurotrophic factor for the treatment of blindness and deafness", International Journal of Nanomedicine, 2015, 10:3245-3267.
Liu et al., "Gene Therapy Targeting Glaucoma: Where Are We?" Survey of Ophthalmology, 2009, 54(4):472-486.
Martin et al., "Gene Therapy with Brain-Derived Neurotrophic Factor As a Protection: Retinal Ganglion Cells in a Rat Glaucoma Model", Investigative Ophthalmology & Visual Science, 2003, 44(10): 4357-4365.
Ren et al., "Long-Term Rescue of Rat Retinal Ganglion Cells and Visual Function by AAV-Mediated BDNF Expression after Acute Elevation of Intraocular Pressure", Investigative Ophthalmology & Visual Science, 2012, 53(2):1003-1011.
Wang et al., "BDNF and NT-3 expression by using glucocorticoid-induced bicistronic expression vector pGc-BDNF-IRES-NT3 protects apoptotic cells in a cellular injury model", Brain Research, 2012, 1448: 137-143.

* cited by examiner

*Primary Examiner* — Barry A Chestnut
(74) *Attorney, Agent, or Firm* — James S. Keddie; Bozicevic, Field & Francis LLP

(57) ABSTRACT

The invention provides genetic constructs and recombinant vectors comprising such constructs. The constructs and vectors can be used in gene therapy methods for treating a range of disorders, including glaucoma and deafness, or for promoting nerve regeneration and/or survival.

21 Claims, 17 Drawing Sheets

Specification includes a Sequence Listing.

Figure 6

BDNF canonical peptide and coding sequence $\begin{Bmatrix} M & T & I & L & F & L & T & M & V & I & S & Y & F & G & C & M & K & A \\ ATGACG & ATCCTTTTCCTT & ACTATGGTTATTCATACTTCGGTTGCATGAAGGCG \end{Bmatrix}$ — [SEQ ID No. 60]

[SEQ ID No. 61]

Where the Threonine codon is replaced by coding sequences for basic residues which may include the following sequences:

62 $\begin{Bmatrix} M & R \\ ATGAGA \end{Bmatrix}$ 63

64 $\begin{Bmatrix} M & R & R \\ ATGAGAAGA \end{Bmatrix}$ 65

66 $\begin{Bmatrix} M & R & R & R \\ ATGAGAAGAAGA \end{Bmatrix}$ 67

68 $\begin{Bmatrix} M & K \\ ATGAAA \end{Bmatrix}$ 69

70 $\begin{Bmatrix} M & K & K \\ ATGAAAAAA \end{Bmatrix}$ 71

72 $\begin{Bmatrix} M & K & K & K \\ ATGAAAAAAAAA \end{Bmatrix}$ 73

74 $\begin{Bmatrix} M & K & R & R \\ ATGAAAAGAAGA \end{Bmatrix}$ 75

76 $\begin{Bmatrix} M & K & K & R \\ ATGAAAAAAAGA \end{Bmatrix}$ 77

78 $\begin{Bmatrix} M & R & R & K \\ ATGAGAAGAAAA \end{Bmatrix}$ 79

80 $\begin{Bmatrix} M & K & R \\ ATGAAAAGA \end{Bmatrix}$ 81

Where the coding sequence for isoleucine-leucine,phenylalanine-leucine may be substituted with an alternative coding sequence for more hydrophobic amino acids as exemplified by:

82 $\begin{Bmatrix} F & L & F & L \\ TTCCTTTTCCTT \end{Bmatrix}$ 83

84 $\begin{Bmatrix} F & F & F & L \\ TTCTTCTTCCTT \end{Bmatrix}$ 85

86 $\begin{Bmatrix} F & I & F & L \\ TTCATCTTCCTT \end{Bmatrix}$ 87

88 $\begin{Bmatrix} F & I & F & I \\ TTCATCTTCATC \end{Bmatrix}$ 89

90 $\begin{Bmatrix} F & V & F & I \\ TTCGTTTTCATC \end{Bmatrix}$ 91

92 $\begin{Bmatrix} F & V & F & V \\ TTCGTTTTCGTT \end{Bmatrix}$ 93

94 $\begin{Bmatrix} F & L & F & V \\ TTCCTTTTCGTT \end{Bmatrix}$ 95

96 $\begin{Bmatrix} F & I & F & V \\ TTCATCTTCGTT \end{Bmatrix}$ 97

98 $\begin{Bmatrix} F & F & F & I \\ TTCTTCTTCATC \end{Bmatrix}$ 99

100 $\begin{Bmatrix} F & F & F & V \\ TTCTTCTTCGTT \end{Bmatrix}$ 101

102 $\begin{Bmatrix} F & I & L & F & L \\ TTCATCCTTTTCCTT \end{Bmatrix}$ 103

Figure 13
A: BDNF in the HEK293 cell lysates
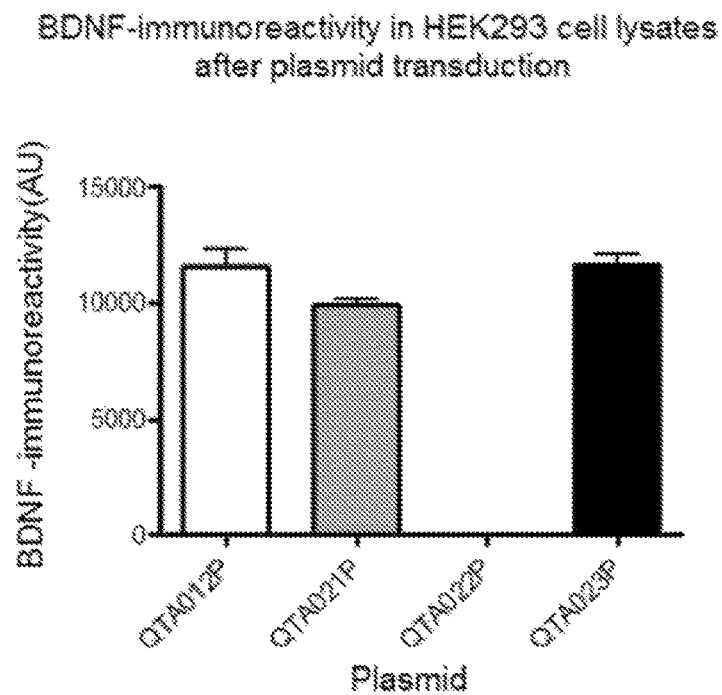
B: eGFP in HEK293 cell lysates
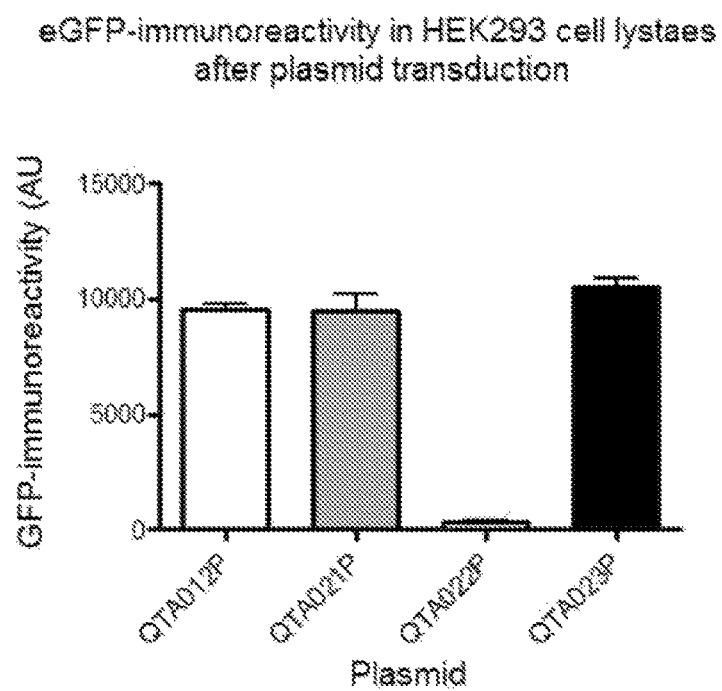

C: BDNF release from HEK293 cells

A: Western blot of HEK293 cells

Figure 14 (cont.)
B: TrkB expression in HEK293 cells
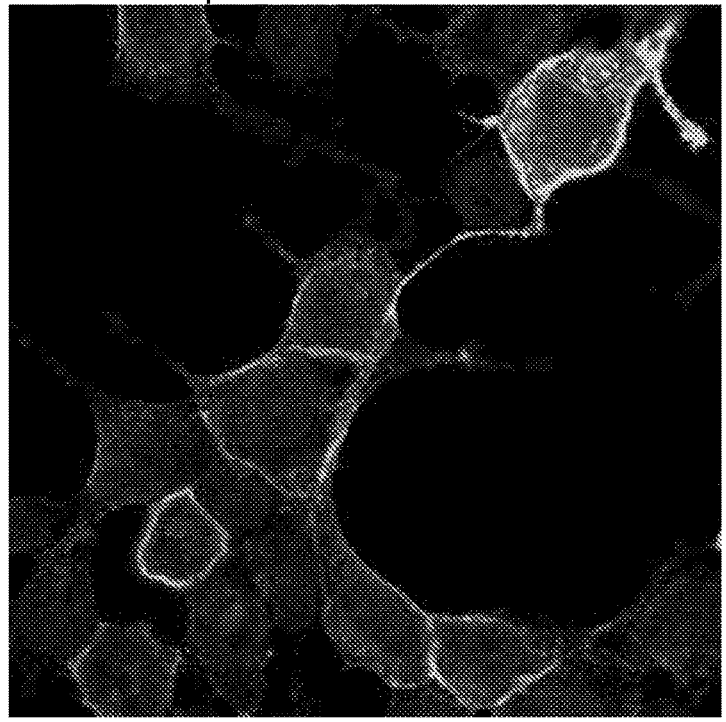
C: BDNF expression in HEK293 cells
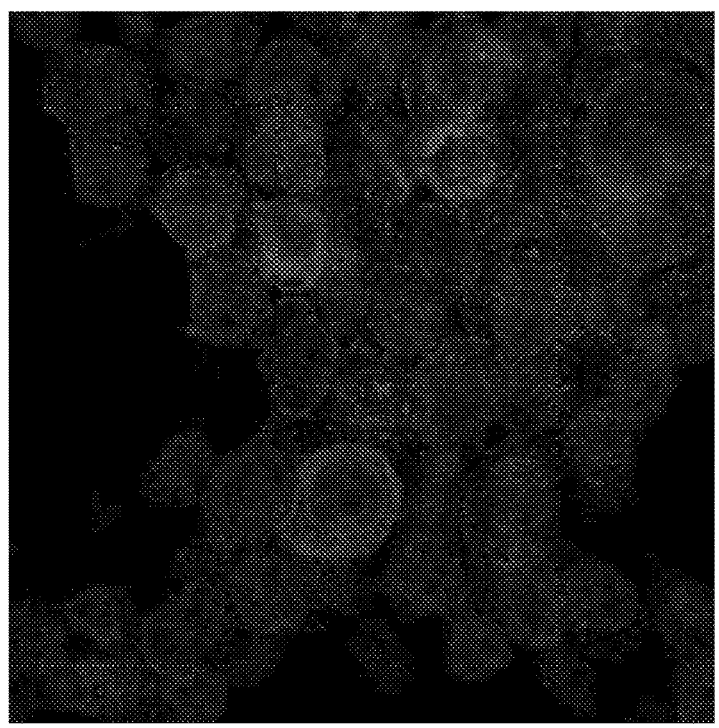

Figure 15
A: TrkB receptor expression
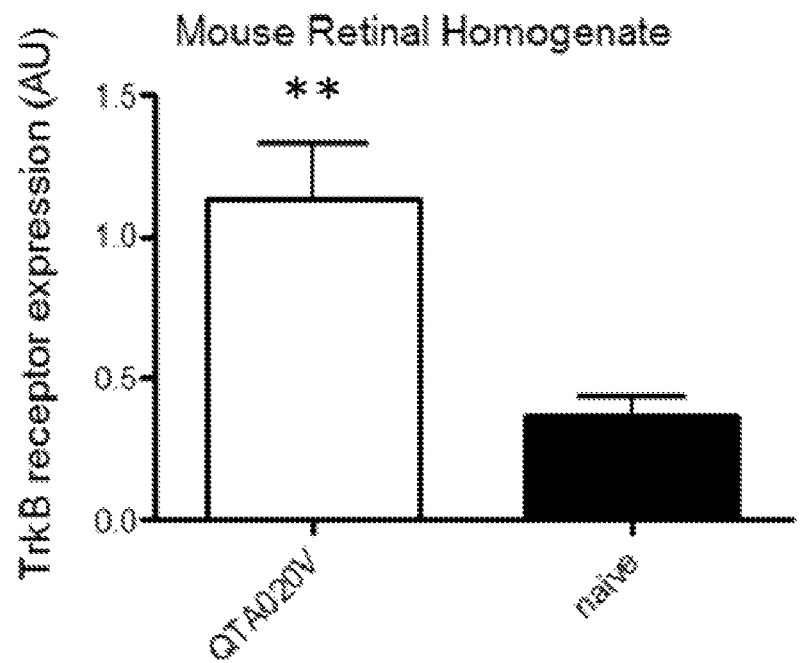
B: BDNF protein expression
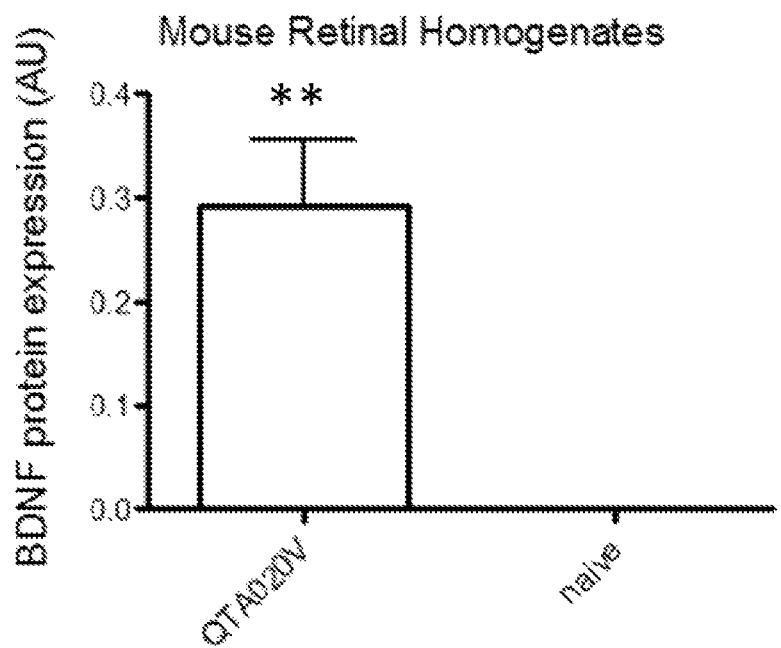

Figure 16
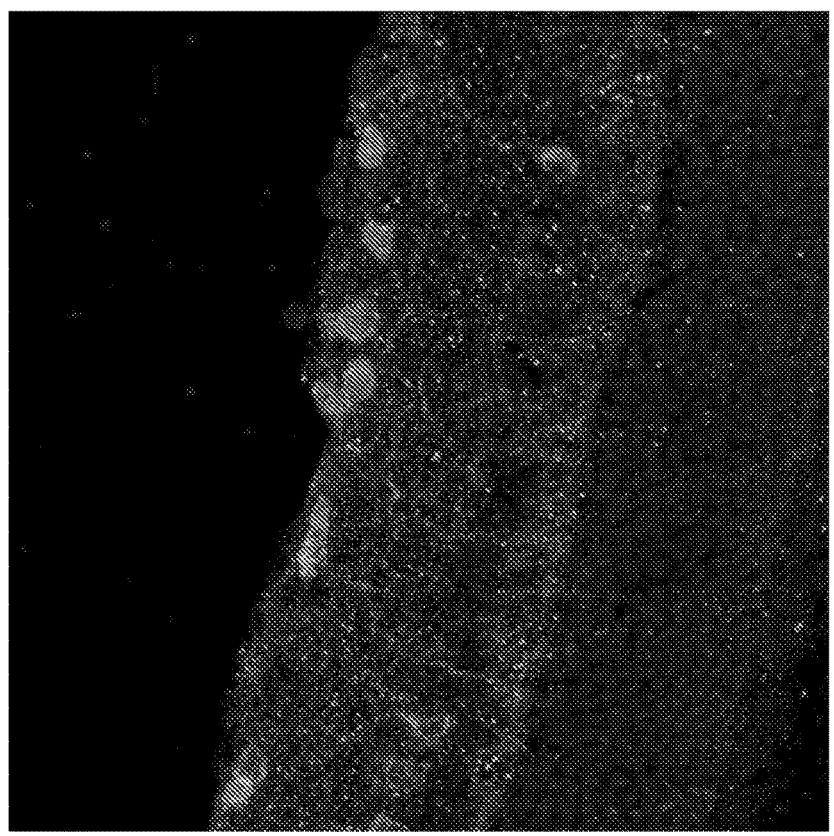
B: BDNF staining (green)
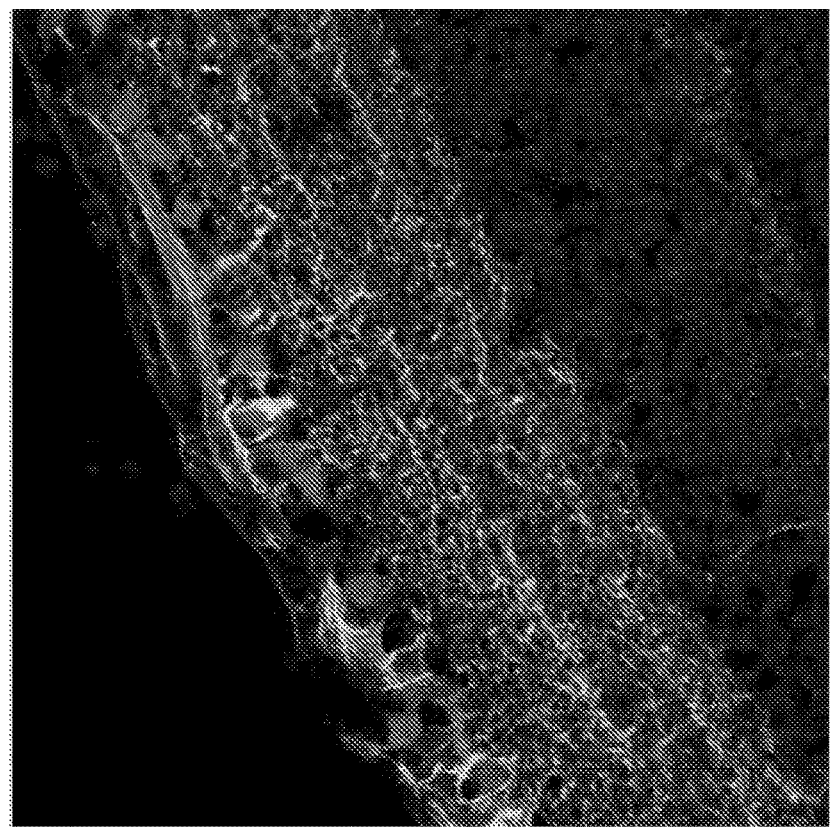
A: TrkB staining (cyan)

GENETIC CONSTRUCT

CROSS-REFERENCE TO RELATED APPLICATIONS

This application is a continuation of U.S. patent application Ser. No. 15/762,089, filed on Mar. 21, 2018, which is a § 371 national phase of International Application No. PCT/GB2016/053319, filed on Oct. 25, 2016, which claims the benefit of United Kingdom Application No. 1518911.1, filed on Oct. 26, 2015, which applications are incorporated by reference herein.

The present invention relates to genetic constructs and recombinant vectors comprising such constructs, and to the uses of the constructs and vectors in gene therapy methods for treating a range of disorders, including glaucoma and deafness, or for promoting nerve regeneration and/or survival.

Glaucoma is a term used to define a group of ocular disorders characterised by progressive optic nerve degeneration, death of retinal ganglion cells (RGC) and axon loss, which results in an excavated appearance of the optic nerve head and loss of vision. Glaucoma is a leading cause of blindness worldwide [1] and the incidence of glaucoma increases dramatically with age. Around half a million people in the U.K. and more than 2.2 million people in North America aged 40 and older have glaucoma. Moreover, every hour, someone goes blind from this sight-threatening disease in the U.S. [2]. As the size of the elderly population continues to grow rapidly, glaucoma has become an imminent social as well as medical problem. Elevated intraocular pressure (IOP) is the most important risk factor for glaucoma [3], besides age and all currently licensed treatments work by lowering IOP [4-5].

Glaucoma can be diagnosed prior to loss of vision by visual field testing and by ophthalmoscopic examination of the optic nerve to detect "cupping". Current management of glaucoma is based on lowering the IOP to normal levels, which are between to and 21 mm Hg, in order to prevent further optic nerve damage using topically applied drugs [6]. The mean IOP in normal adults is 15 to 16 mm Hg. Currently there are five major classes of medications that are used to lower the IOP: β-adrenergic antagonists, adrenergic agonists, parasympathomimetics, prostaglandin-like analogues and carbonic anhydrase inhibitors [7]. Whilst relatively effective in reducing IOP when correctly used, these drugs can cause severe side effects in some patients and thereby adversely affect the quality of the patient's life. In addition, adherence to IOP-lowering eye drop treatment is often poor, particularly in elderly patients who are required to take multiple medications. It has been estimated that less than 50% of patients prescribed IOP lowering treatment actually use it regularly as directed, with obvious implications for control of the underlying condition. If additional lowering of IOP is indicated, or if medication fails to sufficiently lower the IOP, laser trabeculoplasty may be used, but this treatment fails to achieve adequate IOP lowering in many patients. If IOP is still not adequately controlled, incisional glaucoma surgery may be indicated. However, IOP lowering treatment fails to prevent deterioration in many patients and glaucoma remains the leading cause of irreversible blindness worldwide. Neuroprotection of the glaucomatous RGCs and their axon projections, which form the optic nerve, would therefore be a valuable therapeutic paradigm for use as an adjunct to conventional IOP lowering treatments and particularly important in patients deteriorating despite conventional therapy [8].

Glaucomatous optic neuropathy appears to result from specific pathophysiological changes and subsequent death of RGCs and their axons. The process of RGC death is thought to be biphasic, i.e. a primary injury responsible for initiation of damage followed by a slower, secondary degeneration attributable to the hostile environment surrounding the degenerating cells [9].

RGC death mechanisms in experimental animal models of glaucoma and human glaucoma have been shown to involve apoptosis [10]. Although the molecular mechanism triggering apoptosis has not been identified, deprivation of neurotrophic factors, ischemia, chronic elevation of glutamate and disorganized nitric oxide metabolism are suspected to be possible mechanisms [11].

Brain-derived neurotrophic factor (BDNF) along with nerve growth factor (NGF), neurotrophin-3 (NT-3), and neurotrophin-4/5 (NT-4/5) are members of the neurotrophin family of trophic factors [12-13]. The neurotrophins play essential roles in the development, survival and function of a wide range of neurons in both the peripheral and central nervous systems, including RGCs. Neurotrophins interact with two cell surface receptors, low affinity $p75^{NTR}$ receptors and the high affinity tyrosine receptor kinase (Trk) family [12-13]. Nerve growth factor (NGF) preferentially binds TrkA, Brain Derived Neurotrophic Factor (BDNF) and Neurotrophin-4/5 (NT4/5) bind to tropmyosin receptor kinase-B (TrkB), and Neurotrophin-3 (NT-3) binds TrkC (and TrkA to a lesser extent) [12-13].

Among neurotrophins, BDNF is the most potent survival factor for injured RGCs [14-21]. BDNF is a protein molecule produced in the brain and transported to the retina by way of retrograde axonal transport through the optic nerve, where it supports RGCs and maintains their survival [15-21]. In certain conditions, such as during excitotoxic insults with glutamate receptor agonists, such as N-methyl-D-aspartate, BDNF can also be produced in RGCs although at relatively low levels [22-23]. BDNF is normally produced as a prepro-polypeptide (i.e. preproBDNF) containing a short signal peptide sequence, which facilitates trafficking of the entire polypeptide to vesicles for release into the extracellular space. Cleavage and removal of the signal peptide converts preproBDNF into proBDNF. An N-terminal proBDNF sequence is then cleaved either intracellulary or extracellularly to create mature BDNF (mBDNF) [24]. Both pro-BDNF and mBDNF possess biological activity with pro-BDNF preferentially activating $p75^{NTR}$ receptors and the shorter mBDNF activating TrkB receptors [25-27]. Activation of $P75^{NTR}$ and TrkB receptors in the retina show opposing effects on RGC survival, the former being responsible for apoptosis through direct RGC-cell-body-$p75^{NTR}$-activation [25-28] or indirectly via $p75^{NTR}$ activation on Müller cells, thereby stimulating release of Tumour Necrosis Factor-alpha (TNF-α) which further promotes RGC loss [29].

Animal models of glaucoma have demonstrated that following nerve crush, or raised IOP, there is a shift away from neurotrophic mBDNF/TrkB signalling towards pro-BDNF/$p75^{NTR}$ pathways. Reduced levels of mBDNF and TrkB receptors in the retina have been demonstrated [27, 30-31] together with opposing elevations in the relative levels of pro-BDNF [28] and $p75^{NTR}$ receptors [32]. Supplementation of mBDNF through ocular injections of recombinant protein to rats with experimentally elevated IOP increases the survival of RGCs compared with untreated eyes, thereby confirming a key neuroprotective role for this neurotrophin [19-21].

To maintain levels of mBDNF in eyes with glaucoma, regular injections of mBDNF would be required as mBDNF is rapidly degraded within the eye. To overcome the need for regular intraocular injections of mBDNF, attempts to provide constant elevated BDNF have resorted to using recombinant adenovirus or adeno-associated viral (rAAV) vector delivery of the transgene coding for BDNF to the retina to delay or prevent RGC death in animal models of glaucoma [18, 33-34]. rAAV vectors consist of a single-stranded DNA genome. They have has been successfully used as a viral vector for gene therapy in multiple clinical trials whilst displaying limited toxicity. Whilst intravitreal injections of recombinant mBDNF alone, or increasing local BDNF production via gene therapy, have been shown to be effective in preventing loss in RGCs over a short period following IOP elevation or other optic nerve damage, the beneficial effect of BDNF have been shown to be transient [18]. However, gene therapy which incorporates the endogenous BDNF gene sequence is also capable of producing and releasing pro-BDNF as well as the intended mBDNF.

Gene therapy aimed at attenuating or preventing loss in TrkB signalling through increased expression of the receptor in RGCs or through constant stimulation of remaining extracellular TrkB receptors using an antibody with agonist properties has also demonstrated success in preventing RGC loss [35-36]. However, reductions in trophic signalling through the mBDNF/TrkB pathway is further complicated by internalisation of mBDNF-activated TrkB receptors and replacement of these receptors at the cell surface with TrkB isoforms incapable of intracellular signalling [37-38]. Furthermore, the biochemical system responsible for deactivation of TrkB receptors following autophosphorylation of TrkB receptor dimers in the presence of mBDNF is upregulated in retinas subjected to raised IOP [39].

Furthermore, in addition to glaucoma, the BDNF/TrkB axis has also been implicated in neuroprotection of components of the inner ear, specifically of the cochlear structure where insults can result in loss of hair cells resulting in deafness [40-42], and of nerve regeneration [43-44].

There is therefore a need for an improved gene therapy for the treatment of glaucoma and deafness, and for promoting nerve regeneration or survival.

The inventors have constructed a novel genetic construct, which encodes the tyrosine kinase receptor B (TrkB), and an agonist of the TrkB receptor under the control of a single promoter. The promoter of the construct may be used to ensure that the agonist and the receptor are only expressed in retinal ganglion cells (RGCs), cochlear or nerve cells, and promote the survival of these cells.

Thus, according to a first aspect of the invention, there is provided a genetic construct comprising a promoter operably linked to a first coding sequence, which encodes the tyrosine kinase receptor B (TrkB), and a second coding sequence, which encodes an agonist of the TrkB receptor.

The inventors have demonstrated in the Examples that it is possible to combine the genes which code for both the TrkB receptor and its agonist in a single genetic construct. This was especially challenging given their large sizes, and it could not have been predicted that it would have been possible to co-express them in physiologically useful concentrations. Advantageously, with the construct of the invention, there is no need to inject a recombinant protein, as described in the prior art. Furthermore, in the prior art, it is still necessary to perform regular injections of protein, whereas the construct of the invention only requires a single gene therapy injection.

Preferably, in use, the TrkB receptor is activated by the agonist to thereby promote survival of retinal ganglion cells (RGCs), nerve cells or cochlear cells. Advantageously, the construct of the invention may therefore be used to target RGCs, nerve cells or cochlear cells in order to maintain or enhance TrkB-signalling in these cells. Thus, the construct may be used to maximise protection against pathophysiological stressors of glaucoma and deafness, and to promote nerve regeneration and/or survival. Furthermore, the construct may be used to provide long-term treatment of glaucoma or deafness due to the expression of the TrkB receptor and an agonist of the receptor under the control of one or more promoter. Consequently, the construct has overcome the need to use multiple alternative treatments, which, even in combination, provide a transient therapeutic effect. Moreover, the construct of the invention is advantageous because it may be used to significantly enhance RGC or cochlear cell sensitivity to TrkB receptor agonists due to a localised increase in both the TrkB receptor and the agonist of the receptor.

Preferably, the genetic construct of the invention comprises an expression cassette, one embodiment of which is shown in FIG. 1. As can be seen in FIG. 1, the construct comprises the promoter, the first nucleotide sequence encoding the TrkB receptor, and the second nucleotide sequence encoding mature brain derived neurotrophic (mBDNF), which acts as a preferred agonist of the TrkB receptor. It will be appreciated, however, that other agonist may be used, as discussed herein. Also as shown in FIG. 1, the expression cassette also includes a 2A spacer sequence, a sequence encoding Hepatitis Virus Post-transcriptional Regulatory Element (WHPE), a sequence encoding a polyA tail, and left and right hand Inverted Terminal Repeat sequences (ITRs).

Hence, preferably the genetic construct comprises a spacer sequence disposed between the first and second coding sequences, which spacer sequence encodes a peptide spacer that is configured to be digested or cut to thereby produce the TrkB receptor and the agonist as separate molecules. In the embodiment illustrated in FIG. 1, the coding sequence for the TrkB receptor is disposed 5' of the coding sequence for the receptor agonist (BDNF) with the spacer sequence therebetween. However, in another embodiment, the coding sequence for the receptor agonist may be disposed 5' of the coding sequence for the receptor with the spacer sequence therebetween.

Preferably, the genetic construct comprises a nucleotide sequence encoding Woodchuck Hepatitis Virus Post-transcriptional Regulatory Element (WHPE), which enhances the expression of the two transgenes, i.e. the TrkB receptor and its agonist, which is preferably BDNF. Preferably, the WHPE coding sequence is disposed 3' of the transgene coding sequence.

One embodiment of the Woodchuck Hepatitis Virus Post-transcriptional Regulatory Element (WHPE) is 592 bp long, including gamma-alpha-beta elements, and is referred to herein as SEQ ID No: 57, as follows:

```
                                          [SEQ ID NO. 57]
AATCAACCTCTGGATTACAAAATTTGTGAAAGATTGACTGGTATTCTTAA

CTATGTTGCTCCTTTTACGCTATGTGGATACGCTGCTTTAATGCCTTTGT

ATCATGCTATTGCTTCCCGTATGGCTTTCATTTTCTCCTCCTTGTATAAA

TCCTGGTTGCTGTCTCTTTATGAGGAGTTGTGGCCCGTTGTCAGGCAACG

TGGCGTGGTGTGCACTGTGTTTGCTGACGCAACCCCCACTGGTTGGGGCA
```

-continued

```
TTGCCACCACCTGTCAGCTCCTTTCCGGGACTTTCGCTTTCCCCCTCCCT

ATTGCCACGGCGGAACTCATCGCCGCCTGCCTTGCCCGCTGCTGGACAGG

GGCTCGGCTGTTGGGCACTGACAATTCCGTGGTGTTGTCGGGGAAGCTGA

CGTCCTTTCCATGGCTGCTCGCCTGTGTTGCCACCTGGATTCTGCGCGGG

ACGTCCTTCTGCTACGTCCCTTCGGCCCTCAATCCAGCGGACCTTCCTTC

CCGCGGCCTGCTGCCGGCTCTGCGGCCTCTTCCGCGTCTTCGCCTTCGCC

CTCAGACGAGTCGGATCTCCCTTTGGGCCGCCTCCCCGCCTG
```

Preferably, the WHPE comprises a nucleic acid sequence substantially as set out in SEQ ID No: 57, or a fragment or variant thereof.

However, in a preferred embodiment, a truncated WHPE is used, which is 247 bp long due to deletion of the beta element, and which is referred to herein as SEQ ID No: 58, as follows:

[SEQ ID NO. 58]
```
AATCAACCTCTGGATTACAAAATTTGTGAAAGATTGACTGGTATTCTTAA

CTATGTTGCTCCTTTTACGCTATGTGGATACGCTGCTTTAATGCCTTTGT

ATCATGCTATTGCTTCCCGTATGGCTTTCATTTTCTCCTCCTTGTATAAA

TCCTGGTTAGTTCTTGCCACGGCGGAACTCATCGCCGCCTGCCTTGCCCG

CTGCTGGACAGGGGCTCGGCTGTTGGGCACTGACAATTCCGTGGTGT
```

Advantageously, the truncated WHPE sequence used in the construct saved about 300 bp in total without negatively impacting on transgene expression. Preferably, the WHPE comprises a nucleic acid sequence substantially as set out in SEQ ID No: 58, or a fragment or variant thereof.

Preferably, the genetic construct comprises a nucleotide sequence encoding a polyA tail. Preferably, the polyA tail coding sequence is disposed 3' of the transgene coding sequence, and preferably 3' of the WHPE coding sequence.

Preferably, the polyA tail comprises the simian virus 40 poly-A 224 bp sequence. One embodiment of the polyA tail is referred to herein as SEQ ID No: 59, as follows:

[SEQ ID NO. 59]
```
AGCAGACATGATAAGATACATTGATGAGTTTGGACAAACCACAACTAGAA

TGCAGTGAAAAAAATGCTTTATTTGTGAAATTTGTGATGCTATTGCTTTA

TTTGTAACCATTATAAGCTGCAATAAACAAGTTAACAACAACAATTGCAT

TCATTTTATGTTTCAGGTTCAGGGGGAGGTGTGGGAGGTTTTTTAAAGCA

AGTAAAACCTCTACAAATGTGGTA
```

Preferably, the polyA tail comprises a nucleic acid sequence substantially as set out in SEQ ID No: 59, or a fragment or variant thereof.

Preferably, the genetic construct comprises left and/or right Inverted Terminal Repeat sequences (ITRs). Preferably, each ITR is disposed at the 5' and/or 3' end of the construct.

The promoter in the genetic construct of the first aspect may be any nucleotide sequence that is capable of inducing RNA polymerase to bind to and transcribe the first and second coding sequences. In one preferred embodiment, the promoter is the human synapsin I (SYN I) promoter. One embodiment of the 469 nucleotide sequence encoding the human synapsin I (SYN I) promoter is referred to herein as SEQ ID NO.1, as follows:

[SEQ ID NO. 1]
```
CTGCAGAGGGCCCTGCGTATGAGTGCAAGTGGGTTTTAGGACCAGGATGA

GGCGGGGTGGGGGTGCCTACCTGACGACCGACCCCGACCCACTGGACAAG

CACCCAACCCCCATTCCCCAAATTGCGCATCCCCTATCAGAGAGGGGGAG

GGGAAACAGGATGCGGCGAGGCGCGTGCGCACTGCCAGCTTCAGCACCGC

GGACAGTGCCTTCGCCCCCGCCTGGCGGCGCGCGCCACCGCCGCCTCAGC

ACTGAAGGCGCGCTGACGTCACTCGCCGGTCCCCCGCAAACTCCCCTTCC

CGGCCACCTTGGTCGCGTCCGCGCCGCCGCCGGCCCAGCCGGACCGCACC

ACGCGAGGCGCGAGATAGGGGGGCACGGGCGCGACCATCTGCGCTGCGGC

GCCGGCGACTCAGCGCTGCCTCAGTCTGCGGTGGGCAGCGGAGGAGTCGT

GTCGTGCCTGAGAGCGCAG
```

Preferably, therefore, the promoter may comprise a nucleotide acid sequence substantially as set out in SEQ ID No: 1, or a fragment or variant thereof.

In another preferred embodiment, the promoter is the CAG promoter. The CAG promoter preferably comprises the cytomegalovirus early enhancer element, the first exon and the first intron of chicken beta-actin gene and the splice acceptor of the rabbit beta-globin gene, thereby facilitating tissue specific expression in RGCs and cochlear cells only. One embodiment of the 1733 nucleotide sequence encoding the CAG promoter is referred to herein as SEQ ID NO.2, as follows:

[SEQ ID NO. 2]
```
CTCGACATTGATTATTGACTAGTTATTAATAGTAATCAATTACGGGGTCA

TTAGTTCATAGCCCATATATGGAGTTCCGCGTTACATAACTTACGGTAAA

TGGCCCGCCTGGCTGACCGCCCAACGACCCCCGCCCATTGACGTCAATAA

TGACGTATGTTCCCATAGTAACGCCAATAGGGACTTTCCATTGACGTCAA

TGGGTGGAGTATTTACGGTAAACTGCCCACTTGGCAGTACATCAAGTGTA

TCATATGCCAAGTACGCCCCCTATTGACGTCAATGACGGTAAATGGCCCG

CCTGGCATTATGCCCAGTACATGACCTTATGGGACTTTCCTACTTGGCAG

TACATCTACGTATTAGTCATCGCTATTACCATGGTCGAGGTGAGCCCCAC

GTTCTGCTTCACTCTCCCCATCTCCCCCCCCTCCCCACCCCCAATTTTGT

ATTTATTTATTTTTTAATTATTTTGTGCAGCGATGGGGGCGGGGGGGGGG

GGGGGGCGCGCGCCAGGCGGGGCGGGGCGGGGCGAGGGGCGGGGCGGGGC

GAGGCGGAGAGGTGCGGCGGCAGCCAATCAGAGCGGCGCGCTCCGAAAGT

TTCCTTTTATGGCGAGGCGGCGGCGGCGGCGGCCCTATAAAAAGCGAAGC

GCGCGGCGGGCGGGAGTCGCTGCGCGCTGCCTTCGCCCCGTGCCCCGCTC

CGCCGCCGCCTCGCGCCGCCCGCCCCGGCTCTGACTGACCGCGTTACTCC

CACAGGTGAGCGGGCGGGACGGCCCTTCTCCTCCGGGCTGTAATTAGCGC

TTGGTTTAATGACGGCTTGTTTCTTTTCTGTGGCTGCGTGAAAGCCTTGA

GGGGCTCCGGGAGGGCCCTTTGTGCGGGGGGAGCGGCTCGGGGGTGCGT

GCGTGTGTGTGTGCGTGGGGAGCGCCGCGTGCGGCTCCGCGCTGCCCGGC

GGCTGTGAGCGCTGCGGGCGCGGCGCGGGGCTTTGTGCGCTCCGCAGTGT

GCGCGAGGGGAGCGCGGCCGGGGGCGGTGCCCCGCGGTGCGGGGGGGCT
```

```
GCGAGGGGAACAAAGGCTGCGTGCGGGGTGTGTGCGTGGGGGGTGAGCA

GGGGGTGTGGGCGCGTCGGTCGGGCTGCAACCCCCCCTGCACCCCCCTCC

CCGAGTTGCTGAGCACGGCCCGGCTTCGGGTGCGGGGCTCCGTACGGGGC

GTGGCGCGGGGCTCGCCGTGCCGGGCGGGGGTGGCGGCAGGTGGGGGTG

CCGGGCGGGGCGGGGCCGCCTCGGGCCGGGAGGGCTCGGGGGAGGGGCG

CGGCGGCCCCCGGAGCGCCGGCGGCTGTCGAGGCGCGGCGAGCCGCAGCC

ATTGCCTTTTATGGTAATCGTGCGAGAGGGCGCAGGGACTTCCTTTGTCC

CAAATCTGTGCGGAGCCGAAATCTGGGAGGCGCCGCCGCACCCCCTCTAG

CGGGCGCGGGGCGAAGCGGTGCGGCGCCGGCAGGAAGGAAATGGGCGGGG

AGGGCCTTCGTGCGTCGCCGCGCCGCCGTCCCCTTCTCCCTCTCCAGCCT

CGGGGCTGTCCGCGGGGGACGGCTGCCTTCGGGGGGACGGGGCAGGGC

GGGGTTCGGCTTCTGGCGTGTGACCGGCGGCTCTAGAGCCTCTGCTAACC

ATGTTCATGCCTTCTTCTTTTTCCTACAGCTCCTGGGCAACGTGCTGGTT

ATTGTGCTGTCTCATCATTTTGGCAAAGAATTG
```

In another preferred embodiment, the promoter is a truncated form of the CAG promoter, such as a 664 nucleotide form of the promoter referred to herein as SEQ ID NO.3, as follows:

[SEQ ID No: 3]
```
CTAGATCTGAATTCGGTACCCTAGTTATTAATAGTAATCAATTACGGGGT

CATTAGTTCATAGCCCATATATGGAGTTCCGCGTTACATAACTTACGGTA

AATGGCCCGCCTGGCTGACCGCCCAACGACCCCCGCCCATTGACGTCAAT

AATGACGTATGTTCCCATAGTAACGCCAATAGGGACTTTCCATTGACGTC

AATGGGTGGACTATTTACGGTAAACTGCCCACTTGGCAGTACATCAAGTG

TATCATATGCCAAGTACGCCCCCTATTGACGTCAATGACGGTAAATGGCC

CGCCTGGCATTATGCCCAGTACATGACCTTATGGGACTTTCCTACTTGGC

AGTACATCTACGTATTAGTCATCGCTATTACCATGGTCGAGGTGAGCCCC

ACGTTCTGCTTCACTCTCCCCATCTCCCCCCCCTCCCCACCCCCAATTTT

GTATTTATTTATTTTTTAATTATTTTGTGCAGCGATGGGGGCGGGGGGGG

GGGGGGGCGCGCGCCAGGCGGGGCGGGGCGGGGCGAGGGCGGGGCGGG

GCGAGGCGGAGAGGTGCGGCGGCAGCCAATCAGAGCGGCGCGCTCCGAAA

GTTTCCTTTTATGGCGAGGCGGCGGCGGCGGCGGCCCTATAAAAGCGAA

GCGCGCGGCGGGCG
```

In yet a further preferred embodiment, the promoter is a truncated form of the CAG promoter, such as a 584 nucleotide form of the promoter referred to herein as SEQ ID NO. 48, as follows:

[SEQ ID No: 48]
```
GCGTTACATAACTTACGGTAAATGGCCCGCCTGGCTGACCGCCCAACGAC

CCCCGCCCATTGACGTCAATAATGACGTATGTTCCCATAGTAACGCCAAT

AGGGACTTTCCATTGACGTCAATGGGTGGACTATTTACGGTAAACTGCCC

ACTTGGCAGTACATCAAGTGTATCATATGCCAAGTACGCCCCCTATTGAC

GTCAATGACGGTAAATGGCCCGCCTGGCATTATGCCCAGTACATGACCTT

ATGGGACTTTCCTACTTGGCAGTACATCTACGTATTAGTCATCGCTATTA

CCATGGTCGAGGTGAGCCCCACGTTCTGCTTCACTCTCCCCATCTCCCCC

CCCTCCCCACCCCCAATTTTGTATTTATTTATTTTTTAATTATTTTGTGC

AGCGATGGGGCGGGGGGGGGGGGGGCGCGCGCCAGGCGGGGCGGGC

GGGGCGAGGGCGGGCGGGCGAGGCGGAGAGGTGCGGCGGCAGCCAAT

CAGAGCGGCGCGCTCCGAAAGTTTCCTTTTATGGCGAGGCGGCGGCGGCG

GCGGCCCTATAAAAGCGAAGCGCGCGGCGGGCG
```

Therefore, preferably the promoter comprises a nucleotide acid sequence substantially as set out in SEQ ID No: 2, 3 or 48, or a fragment or variant thereof.

Many bicistronic gene constructs presented in the scientific literature have either (i) incorporated dual promoters to separately drive expression of two genes, or (ii) use the internal ribosome entry site (IRES) of the encepahlomyocarditis virus (EMCV) to link two genes transcribed from a single promoter within recombinant viral vectors [45-46]. However, the efficiency of IRES-dependent translation may vary in different cells and tissues and IRES-dependent second gene expression can be significantly lower than cap-dependent first gene expression in bicistronic vectors [47]. Moreover, the size limitation of rAAV vectors (generally <5 kb) will prevent the incorporation of large gene constructs, such as the TrkB receptor together with BDNF using dual promoters or IRES linkers.

Accordingly, in a preferred embodiment, the genetic construct comprises a spacer sequence disposed between the first and second coding sequences, which spacer sequence encodes a peptide spacer that is configured to be digested to thereby produce the TrkB receptor and agonist as separate molecules. Preferably, the spacer sequence comprises and encodes a viral peptide spacer sequence, more preferably a viral 2A peptide spacer sequence [47]. Preferably, the 2A peptide sequence connects the first coding sequence to the second coding sequence. This enables the construct to overcome the size restrictions that occur with expression in various vectors and enables expression of all of the peptides encoded by the construct of the first aspect to occur under control of a single promoter, as a single protein.

Thus, following the translation of the single protein containing the sequences of TrkB, the 2A peptide, and the agonist (preferably BDNF), cleavage occurs in the viral 2A peptide sequence at the terminal glycine-proline link, thereby liberating two proteins, i.e. TrkB and agonist (i.e. mBDNF). The genetic construct is designed such that the remaining short N-terminal amino acid sequence of the viral 2A peptide remain attached to the intracellular portion of the TrkB receptor, thereby removing immunogenicity risks and not interfering with the intracellular signalling capability of the mature receptor. The residual proline amino acid from the C-terminal viral 2A sequence remains attached to the N-terminal BDNF signal peptide and is ultimately removed from the mBDNF protein following cleavage of the signal sequence from the mature protein.

The inventors have generated two embodiments of the spacer sequence. One important section of the peptide spacer sequence, which is common to both embodiments described herein, is the C-terminus. Accordingly, preferably the peptide spacer sequence comprises an amino acid sequence referred to herein as SEQ ID NO. 4, or a fragment or variant thereof, as follows:

[SEQ ID No: 4]
QAGDVEENPGP

Preferably, the digestion or cut site of the peptide spacer sequence is disposed between the terminal glycine and end proline in SEQ ID No:4.

In a first preferred embodiment, the spacer sequence comprises a nucleotide sequence referred to herein as SEQ ID NO.5, or a fragment or variant thereof, as follows:

[SEQ ID No: 5]
GGAAGCGGAGCTACTAACTTCAGCCTGCTGAAGGCTGGAGACGTGGAGGA
GAACCCTGGACCT

In this first embodiment, the peptide spacer sequence comprises an amino acid sequence referred to herein as SEQ ID NO. 6, or a fragment or variant thereof, as follows:

[SEQ ID No: 6]
GSGATNFSLLQAGDVEENPGP

In a second preferred embodiment, the spacer sequence comprises a nucleotide sequence referred to herein as SEQ ID NO. 7, or a fragment or variant thereof, as follows:

[SEQ ID No: 7]
AGCGGAGCTACTAACTTCAGCCTGCTGAAGCAGGCTGGAGACGTGGAGGA
GAACCCTGGACCT

In this second embodiment, the peptide spacer sequence comprises an amino acid sequence referred to herein as SEQ ID NO. 8, or a fragment or variant thereof, as follows:

[SEQ ID No: 8]
SGATNFSLLKQAGDVEENPGP

The inventors have carefully considered the sequences of the TrkB receptor, and have produced several preferred embodiments of the receptor that is encoded by the first coding sequence in the genetic construct of the first aspect.

In one preferred embodiment, the first coding sequence comprises a nucleotide sequence encoding the human canonical isoform of TrkB. Preferably, the canonical isoform of TrkB comprises an amino acid sequence (822 residues) referred to herein as SEQ ID NO. 9, or a fragment or variant thereof, as set out below:

[SEQ ID No: 9]
MSSWIRWHGPAMARLWGFCWLVVGFWRAAFACPTSCKCSASRIWCSDPSP
GIVAFPRLEPNSVDPENITEIFIANQKRLEIINEDDVEAYVGLRNLTIVD
SGLKFVAHKAFLKNSNLQHINFTRNKLTSLSRKHFRHLDLSELILVGNPF
TCSCDIMWIKTLQEAKSSPDTQDLYCLNESSKNIPLANLQIPNCGLPSAN
LAAPNLTVEEGKSITLSCSVAGDPVPNMYWDVGNLVSKHMNETSHTQGSL
RITNISSDDSGKQISCVAENLVGEDQDSVNLTVHFAPTITFLESPTSDHH
WCIPFTVKGNPKPALQWFYNGAILNESKYICTKIHVTNHTEYHGCLQLDN
PTHMNNGDYTLIAKNEYGKDEKQISAHFMGWPGIDDGANPNYPDVIYEDY
GTAANDIGDTTNRSNEIPSTDVTDKTGREHLSVYAVVVIASVVGFCLLVM

-continued
LFLLKLARHSKFGMKGPASVISNDDDSASPLHHISNGSNTPSSSEGGPDA
VIIGMTKIPVIENPQYFGITNSQLKPDTFVQHIKRHNIVLKRELGEGAFG
KVFLAECYNLCPEQDKILVAVKTLKDASDNARKDFHREAELLTNLQHEHI
VKFYGVCVEGDPLIMVFEYMKHGDLNKFLRAHGPDAVLMAEGNPPTELTQ
SQMLHIAQQIAAGMVYLASQHFVHRDLATRNCLVGENLLVKIGDFGMSRD
VYSTDYYRVGGHTMLPIRWMPPESIMYRKFTTESDVWSLGVVLWEIFTYG
KQPWYQLSNNEVIECITQGRVLQRPRTCPQEVYELMLGCWQREPHMRKNI
KGIHTLLQNLAKASPVYLDILG Preferably, in this embodiment, the first coding sequence comprises a nucleotide sequence referred to herein as SEQ ID NO. 10, or a fragment or variant thereof, as set out below:

[SEQ ID No: 10]
ATGTCGTCCTGGATAAGGTGGCATGGACCCGCCATGGCGCGGCTCTGGGG
CTTCTGCTGGCTGGTTGTGGGCTTCTGGAGGGCCGCTTTCGCCTGTCCCA
CGTCCTGCAAATGCAGTGCCTCTCGGATCTGGTGCAGCGACCCTTCTCCT
GGCATCGTGGCATTTCCGAGATTGGAGCCTAACAGTGTAGATCCTGAGAA
CATCACCGAAATTTTCATCGCAAACCAGAAAAGGTTAGAAATCATCAACG
AAGATGATGTTGAAGCTTATGTGGGACTGAGAAATCTGACAATTGTGGAT
TCTGGATTAAAATTTGTGGCTCATAAAGCATTTCTGAAAAACAGCAACCT
GCAGCACATCAATTTTACCCGAAACAAACTGACGAGTTTGTCTAGGAAAC
ATTTCCGTCACCTTGACTTGTCTGAACTGATCCTGGTGGGCAATCCATTT
ACATGCTCCTGTGACATTATGTGGATCAAGACTCTCCAAGAGGCTAAATC
CAGTCCAGACACTCAGGATTTGTACTGCCTGAATGAAAGCAGCAAGAATA
TTCCCCTGGCAAACCTGCAGATACCCAATTGTGGTTTGCCATCTGCAAAT
CTGGCCGCACCTAACCTCACTGTGGAGGAAGGAAAGTCTATCACATTATC
CTGTAGTGTGGCAGGTGATCCGGTTCCTAATATGTATTGGGATGTTGGTA
ACCTGGTTTCCAAACATATGAATGAAACAAGCCACACACAGGGCTCCTTA
AGGATAACTAACATTTCATCCGATGACAGTGGGAAGCAGATCTCTTGTGT
GGCGGAAAATCTTGTAGGAGAAGATCAAGATTCTGTCAACCTCACTGTGC
ATTTTGCACCAACTATCACATTTCTCGAATCTCCAACCTCAGACCACCAC
TGGTGCATTCCATTCACTGTGAAAGGCAACCCCAAACCAGCGCTTCAGTG
GTTCTATAACGGGGCAATATTGAATGAGTCCAAATACATCTGTACTAAAA
TACATGTTACCAATCACACGGAGTACCACGGCTGCCTCCAGCTGGATAAT
CCCACTCACATGAACAATGGGGACTACACTCTAATAGCCAAGAATGAGTA
TGGGAAGGATGAGAAACAGATTTCTGCTCACTTCATGGGCTGGCCTGGAA
TTGACGATGGTGCAAACCCAAATTATCCTGATGTAATTTATGAAGATTAT
GGAACTGCAGCGAATGACATCGGGGACACCACGAACAGAAGTAATGAAAT
CCCTTCCACAGACGTCACTGATAAAACCGGTCGGGAACATCTCTCGGTCT
ATGCTGTGGTGGTGATTGCGTCTGTGGTGGGATTTTGCCTTTTGGTAATG
CTGTTTCTGCTTAAGTTGGCAAGACACTCCAAGTTTGGCATGAAAGGCCC
AGCCTCCGTTATCAGCAATGATGATGACTCTGCCAGCCCACTCCATCACA

```
TCTCCAATGGGAGTAACACTCCATCTTCTTCGGAAGGTGGCCCAGATGCT

GTCATTATTGGAATGACCAAGATCCCTGTCATTGAAAATCCCCAGTACTT

TGGCATCACCAACAGTCAGCTCAAGCCAGACACATTTGTTCAGCACATCA

AGCGACATAACATTGTTCTGAAAAGGGAGCTAGGCGAAGGAGCCTTTGGA

AAAGTGTTCCTAGCTGAATGCTATAACCTCTGTCCTGAGCAGGACAAGAT

CTTGGTGGCAGTGAAGACCCTGAAGGATGCCAGTGACAATGCACGCAAGG

ACTTCCACCGTGAGGCCGAGCTCCTGACCAACCTCCAGCATGAGCACATC

GTCAAGTTCTATGGCGTCTGCGTGGAGGGCGACCCCCTCATCATGGTCTT

TGAGTACATGAAGCATGGGGACCTCAACAAGTTCCTCAGGGCACACGGCC

CTGATGCCGTGCTGATGGCTGAGGGCAACCCGCCCACGGAACTGACGCAG

TCGCAGATGCTGCATATAGCCCAGCAGATCGCCGCGGGCATGGTCTACCT

GGCGTCCCAGCACTTCGTGCACCGCGATTTGGCCACCAGGAACTGCCTGG

TCGGGGAGAACTTGCTGGTGAAAATCGGGGACTTTGGGATGTCCCGGGAC

GTGTACAGCACTGACTACTACAGGGTCGGTGGCCACACAATGCTGCCCAT

TCGCTGGATGCCTCCAGAGAGCATCATGTACAGGAAATTCACGACGGAAA

GCGACGTCTGGAGCCTGGGGGTCGTGTTGTGGGAGATTTTCACCTATGGC

AAACAGCCCTGGTACCAGCTGTCAAACAATGAGGTGATAGAGTGTATCAC

TCAGGGCCGAGTCCTGCAGCGACCCCGCACGTGCCCCCAGGAGGTGTATG

AGCTGATGCTGGGGTGCTGGCAGCGAGAGCCCCACATGAGGAAGAACATC

AAGGGCATCCATACCCTCCTTCAGAACTTGGCCAAGGCATCTCCGGTCTA

CCTGGACATTCTAGGC
```

In another preferred embodiment, the first coding sequence comprises a nucleotide sequence which encodes isoform 4 of TrkB. Preferably, isoform 4 of TrkB comprises an amino acid sequence referred to herein as SEQ ID NO. 11, or a fragment or variant thereof, as set out below:

```
                                          [SEQ ID No: 11]
MSSWIRWHGPAMARLWGFCWLVVGFWRAAFACPTSCKCSASRIWCSDPSP

GIVAFPRLEPNSVDPENITEIFIANQKRLEIINEDDVEAYVGLRNLTIVD

SGLKFVAHKAFLKNSNLQHINFTRNKLTSLSRKHFRHLDLSELILVGNPF

TCSCDIMWIKTLQEAKSSPDTQDLYCLNESSKNIPLANLQIPNCGLPSAN

LAAPNLTVEEGKSITLSCSVAGDPVPNMYWDVGNLVSKHMNETSHTQGSL

RITNISSDDSGKQISCVAENLVGEDQDSVNLTVHFAPTITFLESPTSDHH

WCIPFTVKGNPKPALQWFYNGAILNESKYICTKIHVTNHTEYHGCLQLDN

PTHMNNGDYTLIAKNEYGKDEKQISAHFMGWPGIDDGANPNYPDVIYEDY

GTAANDIGDTTNRSNEIPSTDVTDKTGREHLSVYAVVVIASVVGFCLLVM

LFLLKLARHSKFGMKDFSWFGFGKVKSRQGVGPASVISNDDDSASPLHHI

SNGSNTPSSSEGGPDAVIIGMTKIPVIENPQYFGITNSQLKPDTFVQHIK

RHNIVLKRELGEGAFGKVFLAECYNLCPEQDKILVAVKTLKDASDNARKD

FHREAELLTNLQHEHIVKFYGVCVEGDPLIMVFEYMKHGDLNKFLRAHGP

DAVLMAEGNPPTELTQSQMLHIAQQIAAGMVYLASQHFVHRDLATRNCLV

GENLLVKIGDFGMSRDVYSTDYYRVGGHTMLPIRWMPPESIMYRKFTTES
```

```
DVWSLGVVLWEIFTYGKQPWYQLSNNEVIECITQGRVLQRPRTCPQEVYE

LMLGCWQREPHMRKNIKGIHTLLQNLAKASPVYLDILG
```

Preferably, this embodiment of the first coding sequence comprises a nucleotide sequence referred to herein as SEQ ID NO. 12, or a fragment or variant thereof, as set out below:

```
                                          [SEQ ID No: 12]
ATGTCGTCCTGGATAAGGTGGCATGGACCCGCCATGGCGCGGCTCTGGGG

CTTCTGCTGGCTGGTTGTGGGCTTCTGGAGGGCCGCTTTCGCCTGTCCCA

CGTCCTGCAAATGCAGTGCCTCTCGGATCTGGTGCAGCGACCCTTCTCCT

GGCATCGTGGCATTTCCGAGATTGGAGCCTAACAGTGTAGATCCTGAGAA

CATCACCGAAATTTTCATCGCAAACCAGAAAAGGTTAGAAATCATCAACG

AAGATGATGTTGAAGCTTATGTGGGACTGAGAAATCTGACAATTGTGGAT

TCTGGATTAAAATTTGTGGCTCATAAAGCATTTCTGAAAAACAGCAACCT

GCAGCACATCAATTTTACCCGAAACAAACTGACGAGTTTGTCTAGGAAAC

ATTTCCGTCACCTTGACTTGTCTGAACTGATCCTGGTGGGCAATCCATTT

ACATGCTCCTGTGACATTATGTGGATCAAGACTCTCCAAGAGGCTAAATC

CAGTCCAGACACTCAGGATTTGTACTGCCTGAATGAAAGCAGCAAGAATA

TTCCCCTGGCAAACCTGCAGATACCCAATTGTGGTTTGCCATCTGCAAAT

CTGGCCGCACCTAACCTCACTGTGGAGGAAGGAAAGTCTATCACATTATC

CTGTAGTGTGGCAGGTGATCCGGTTCCTAATATGTATTGGGATGTTGGTA

ACCTGGTTTCCAAACATATGAATGAAACAAGCCACACACAGGGCTCCTTA

AGGATAACTAACATTTCATCCGATGACAGTGGGAAGCAGATCTCTTGTGT

GGCGGAAAATCTTGTAGGAGAAGATCAAGATTCTGTCAACCTCACTGTGC

ATTTTGCACCAACTATCACATTTCTCGAATCTCCAACCTCAGACCACCAC

TGGTGCATTCCATTCACTGTGAAAGGCAACCCCAAACCAGCGCTTCAGTG

GTTCTATAACGGGGCAATATTGAATGAGTCCAAATACATCTGTACTAAAA

TACATGTTACCAATCACACGGAGTACCACGGCTGCCTCCAGCTGGATAAT

CCCACTCACATGAACAATGGGGACTACACTCTAATAGCCAAGAATGAGTA

TGGGAAGGATGAGAAACAGATTTCTGCTCACTTCATGGGCTGGCCTGGAA

TTGACGATGGTGCAAACCCAAATTATCCTGATGTAATTTATGAAGATTAT

GGAACTGCAGCGAATGACATCGGGGACACCACGAACAGAAGTAATGAAAT

CCCTTCCACAGACGTCACTGATAAAACCGGTCGGGAACATCTCTCGGTCT

ATGCTGTGGTGGTGATTGCGTCTGTGGTGGGATTTTGCCTTTTGGTAATG

CTGTTTCTGCTTAAGTTGGCAAGACACTCCAAGTTTGGCATGAAAGATTT

CTCATGGTTTGGATTTGGGAAAGTAAAATCAAGACAAGGTGTTGGCCCAG

CCTCCGTTATCAGCAATGATGATGACTCTGCCAGCCCACTCCATCACATC

TCCAATGGGAGTAACACTCCATCTTCTTCGGAAGGTGGCCCAGATGCTGT

CATTATTGGAATGACCAAGATCCCTGTCATTGAAAATCCCCAGTACTTTG

GCATCACCAACAGTCAGCTCAAGCCAGACACATTTGTTCAGCACATCAAG

CGACATAACATTGTTCTGAAAAGGGAGCTAGGCGAAGGAGCCTTTGGAAA

AGTGTTCCTAGCTGAATGCTATAACCTCTGTCCTGAGCAGGACAAGATCT
```

```
-continued
TGGTGGCAGTGAAGACCCTGAAGGATGCCAGTGACAATGCACGCAAGGAC

TTCCACCGTGAGGCCGAGCTCCTGACCAACCTCCAGCATGAGCACATCGT

CAAGTTCTATGGCGTCTGCGTGGAGGGCGACCCCCTCATCATGGTCTTTG

AGTACATGAAGCATGGGGACCTCAACAAGTTCCTCAGGGCACACGGCCCT

GATGCCGTGCTGATGGCTGAGGGCAACCCGCCCACGGAACTGACGCAGTC

GCAGATGCTGCATATAGCCCAGCAGATCGCCGCGGGCATGGTCTACCTGG

CGTCCCAGCACTTCGTGCACCGCGATTTGGCCACCAGGAACTGCCTGGTC

GGGGAGAACTTGCTGGTGAAAATCGGGGACTTTGGGATGTCCCGGGACGT

GTACAGCACTGACTACTACAGGGTCGGTGGCCACACAATGCTGCCCATTC

GCTGGATGCCTCCAGAGAGCATCATGTACAGGAAATTCACGACGGAAAGC

GACGTCTGGAGCCTGGGGGTCGTGTTGTGGGAGATTTTCACCTATGGCAA

ACAGCCCTGGTACCAGCTGTCAAACAATGAGGTGATAGAGTGTATCACTC

AGGGCCGAGTCCTGCAGCGACCCCGCACGTGCCCCCAGGAGGTGTATGAG

CTGATGCTGGGGTGCTGGCAGCGAGAGCCCCACATGAGGAAGAACATCAA

GGGCATCCATACCCTCCTTCAGAACTTGGCCAAGGCATCTCCGGTCTACC

TGGACATTCTAGGC
```

The inventors have spent considerable inventive endeavour in studying the sequence of the TrkB receptor and have realised that TrkB comprises five tyrosine residues (at position 516, 701, 705, 706 and 816 of SEQ ID No: 9), which are normally phosphorylated following dimerization and autophosphorylation in the presence of a BDNF dimer. A problem with phosphorylation of these five tyrosine residues is that the receptor can be readily deactivated by a phosphatase, such as the Shp-2 phosphatase. Accordingly, in order to prevent phosphorylation and resultant deactivation of the receptor in vivo, preferably one or more of these key tyrosines is mutated (more preferably, to glutamic acid) in order to mimic the resultant phosphotyrosine and produce a receptor which remains active in the presence of BDNF, and which cannot be deactivated by a phosphatise, such as the Shp-2 phosphatase. Such mutant forms of TrkB are aimed at producing TrkB receptor activity which remains active for longer periods, or until the receptor is internalised.

The DNA and amino acid sequences provided below illustrate the positions of these five tyrosine (Y) residues which have been mutated into five glutamic acid (E) residues. It will be appreciated that 1, 2, 3, 4 or 5 of these residues may be mutated to glutamic acid in embodiments of the invention. Various combinations of these mutations is also envisaged, e.g. positions 516 and 701 only, or positions 705, 706 and 816 only, and so on.

Accordingly, in another preferred embodiment, the first coding sequence comprises a nucleotide sequence encoding a mutant form of TrkB receptor, wherein one or more tyrosine residue at position 516, 701, 705, 706 and/or 816 of SEQ ID No: 9 is modified or mutated. Preferably, at least two, three or four tyrosine residues at position 516, 701, 705, 706 and/or 816 of SEQ ID No: 9 are modified. Most preferably, all five tyrosine residues at position 516, 701, 705, 706 and/or 816 of SEQ ID No: 9 are modified.

Preferably, the or each tyrosine residue is modified to a different amino acid residue, more preferably a glutamic acid. Thus, preferably the mutant form of the TrkB receptor comprises Y516E, Y701E, Y705E, Y706E and/or Y816E.

Preferably, the modified form of the TrkB receptor comprises an amino acid sequence referred to herein as SEQ ID NO. 13, or a fragment or variant thereof, as set out below:

```
                                                [SEQ ID No: 13]
MSSWIRWHGPAMARLWGFCWLVVGFWRAAFACPTSCKCSASRIWCSDPSP

GIVAFPRLEPNSVDPENITEIFIANQKRLEIINEDDVEAYVGLRNLTIVD

SGLKFVAHKAFLKNSNLQHINFTRNKLTSLSRKHFRHLDLSELILVGNPF

TCSCDIMWIKTLQEAKSSPDTQDLYCLNESSKNIPLANLQIPNCGLPSAN

LAAPNLTVEEGKSITLSCSVAGDPVPNMYWDVGNLVSKHMNETSHTQGSL

RITNISSDDSGKQISCVAENLVGEDQDSVNLTVHFAPTITFLESPTSDHH

WCIPFTVKGNPKPALQWFYNGAILNESKYICTKIHVTNHTEYHGCLQLDN

PTHMNNGDYTLIAKNEYGKDEKQISAHFMGWPGIDDGANPNYPDVIYEDY

GTAANDIGDTTNRSNEIPSTDVTDKTGREHLSVYAVVVIASVVGFCLLVM

LFLLKLARHSKFGMKGPASVISNDDDSASPLHHISNGSNTPSSSEGGPDA

VIIGMTKIPVIENPQEFGITNSQLKPDTFVQHIKRHNIVLKRELGEGAFG

KVFLAECYNLCPEQDKILVAVKTLKDASDNARKDFHREAELLTNLQHEHI

VKFYGVCVEGDPLIMVFEYMKHGDLNKFLRAHGPDAVLMAEGNPPTELTQ

SQMLHIAQQIAAGMVYLASQHFVHRDLATRNCLVGENLLVKIGDFGMSRD

VESTDEERVGGHTMLPIRWMPPESIMYRKFTTESDVWSLGVVLWEIFTYG

KQPWYQLSNNEVIECITQGRVLQRPRTCPQEVYELMLGCWQREPHMRKNI

KGIHTLLQNLAKASPVELDILG
```

Preferably, in this embodiment, the first coding sequence comprises a nucleotide sequence referred to herein as SEQ ID NO. 14, or a fragment or variant thereof, as set out below:

```
                                                [SEQ ID No: 14]
ATGTCGTCCTGGATAAGGTGGCATGGACCCGCCATGGCGCGGCTCTGGGG

CTTCTGCTGGCTGGTTGTGGGCTTCTGGAGGGCCGCTTTCGCCTGTCCCA

CGTCCTGCAAATGCAGTGCCTCTCGGATCTGGTGCAGCGACCCTTCTCCT

GGCATCGTGGCATTTCCGAGATTGGAGCCTAACAGTGTAGATCCTGAGAA

CATCACCGAAATTTTCATCGCAAACCAGAAAAGGTTAGAAATCATCAACG

AAGATGATGTTGAAGCTTATGTGGGACTGAGAAATCTGACAATTGTGGAT

TCTGGATTAAAATTTGTGGCTCATAAAGCATTTCTGAAAAACAGCAACCT

GCAGCACATCAATTTTACCCGAAACAAACTGACGAGTTTGTCTAGGAAAC

ATTTCCGTCACCTTGACTTGTCTGAACTGATCCTGGTGGGCAATCCATTT

ACATGCTCCTGTGACATTATGTGGATCAAGACTCTCCAAGAGGCTAAATC

CAGTCCAGACACTCAGGATTTGTACTGCCTGAATGAAAGCAGCAAGAATA

TTCCCCTGGCAAACCTGCAGATACCCAATTGTGGTTTGCCATCTGCAAAT

CTGGCCGCACCTAACCTCACTGTGGAGGAAGGAAAGTCTATCACATTATC

CTGTAGTGTGGCAGGTGATCCGGTTCCTAATATGTATTGGGATGTTGGTA

ACCTGGTTTCCAAACATATGAATGAAACAAGCCACACACAGGGCTCCTTA

AGGATAACTAACATTTTCATCCGATGACAGTGGGAAGCAGATCTCTTGTGT

GGCGGAAAATCTTGTAGGAGAAGATCAAGATTCTGTCAACCTACTGTGC
```

-continued
```
ATTTTGCACCAACTATCACATTTCTCGAATCTCCAACCTCAGACCACCAC
TGGTGCATTCCATTCACTGTGAAAGGCAACCCCAAACCAGCGCTTCAGTG
GTTCTATAACGGGGCAATATTGAATGAGTCCAAATACATCTGTACTAAAA
TACATGTTACCAATCACACGGAGTACCACGGCTGCCTCCAGCTGGATAAT
CCCACTCACATGAACAATGGGGACTACACTCTAATAGCCAAGAATGAGTA
TGGGAAGGATGAGAAACAGATTTCTGCTCACTTCATGGGCTGGCCTGGAA
TTGACGATGGTGCAAACCCAAATTATCCTGATGTAATTTATGAAGATTAT
GGAACTGCAGCGAATGACATCGGGGACACCACGAACAGAAGTAATGAAAT
CCCTTCCACAGACGTCACTGATAAAACCGGTCGGGAACATCTCTCGGTCT
ATGCTGTGGTGGTGATTGCGTCTGTGGTGGGATTTTGCCTTTTGGTAATG
CTGTTTCTGCTTAAGTTGGCAAGACACTCCAAGTTTGGCATGAAAGGCCC
AGCCTCCGTTATCAGCAATGATGATGACTCTGCCAGCCCACTCCATCACA
TCTCCAATGGGAGTAACACTCCATCTTCTTCGGAAGGTGGCCCAGATGCT
GTCATTATTGGAATGACCAAGATCCCTGTCATTGAAAATCCCCAGGAATT
TGGCATCACCAACAGTCAGCTCAAGCCAGACACATTTGTTCAGCACATCA
AGCGACATAACATTGTTCTGAAAAGGGAGCTAGGCGAAGGAGCCTTTGGA
AAAGTGTTCCTAGCTGAATGCTATAACCTCTGTCCTGAGCAGGACAAGAT
CTTGGTGGCAGTGAAGACCCTGAAGGATGCCAGTGACAATGCACGCAAGG
ACTTCCACCGTGAGGCCGAGCTCCTGACCAACCTCCAGCATGAGCACATC
GTCAAGTTCTATGGCGTCTGCGTGGAGGGCGACCCCCTCATCATGGTCTT
TGAGTACATGAAGCATGGGGACCTCAACAAGTTCCTCAGGGCACACGGCC
CTGATGCCGTGCTGATGGCTGAGGGCAACCCGCCCACGGAACTGACGCAG
TCGCAGATGCTGCATATAGCCCAGCAGATCGCCGCGGGCATGGTCTACCT
GGCGTCCCAGCACTTCGTGCACCGCGATTTGGCCACCAGGAACTGCCTGG
TCGGGGAGAACTTGCTGGTGAAAATCGGGGACTTTGGGATGTCCCGGGAC
GTGGAAAGCACTGACGAAGAAAGGGTCGGTGGCCACACAATGCTGCCCAT
TCGCTGGATGCCTCCAGAGAGCATCATGTACAGGAAATTCACGACGGAAA
GCGACGTCTGGAGCCTGGGGGTCGTGTTGTGGGAGATTTTCACCTATGGC
AAACAGCCCTGGTACCAGCTGTCAAACAATGAGGTGATAGAGTGTATCAC
TCAGGGCCGAGTCCTGCAGCGACCCCGCACGTGCCCCAGGAGGTGTATG
AGCTGATGCTGGGGTGCTGGCAGCGAGAGCCCCACATGAGGAAGAACATC
AAGGGCATCCATACCCTCCTTCAGAACTTGGCCAAGGCATCTCCGGTCGA
ACTGGACATTCTAGGC
```

It will be appreciated that the second coding sequence encodes an agonist of the TrkB receptor, which is preferably a member of the neurotrophin family of trophic factors. Preferred agonists of the TrkB receptor may therefore be selected from a group of agonists consisting of: Brain-derived neurotrophic factor (BDNF); nerve growth factor (NGF); neurotrophin-3 (NT-3); neurotrophin-4 (NT-4); and neurotrophin-5 (NT-5); or fragments thereof.

The nucleotide and amino acid sequences of each of these agonists will be known to the skilled person. However, by way of example, the amino acid sequence of one embodiment of Neurotrophin-4 (NT-4) is substantially as set out in SEQ ID NO. 49, as follows:

[SEQ ID No: 49]
```
MLPLPSCSLPILLLFLLPSVPIESQPPPSTLPPFLAPEWDLLSPRVVLSR
GAPAGPPLLFLLEAGAFRESAGAPANRSRRGVSETAPASRRGELAVCDAV
SGWVTDRRTAVDLRGREVEVLGEVPAAGGSPLRQYFFETRCKADNAEEGG
PGAGGGGCRGVDRRHWVSECKAKQSYVRALTADAQGRVGWRWIRIDTACV
CTLLSRTGRA
```

The nucleic acid coding sequence of this embodiment of Neurotrophin-4 (NT-4) is substantially as set out in SEQ ID NO. 50, as follows:

[SEQ ID No: 50]
```
ATGCTCCCTCTCCCCTCATGCTCCCTCCCCATCCTCCTCCTTTTCCTCCT
CCCCAGTGTGCCAATTGAGTCCCAACCCCCACCCTCAACATTGCCCCCTT
TTCTGGCCCCTGAGTGGGACCTTCTCTCCCCCCGAGTAGTCCTGTCTAGG
GGTGCCCCTGCTGGGCCCCCTCTGCTCTTCCTGCTGGAGGCTGGGGCCTT
TCGGGAGTCAGCAGGTGCCCCGGCCAACCGCAGCCGGCGTGGGGTGAGCG
AAACTGCACCAGCGAGTCGTCGGGGTGAGCTGGCTGTGTGCGATGCAGTC
AGTGGCTGGGTGACAGACCGCCGGACCGCTGTGGACTTGCGTGGGCGCGA
GGTGGAGGTGTTGGGCGAGGTGCCTGCAGCTGGCGGCAGTCCCCTCCGCC
AGTACTTCTTTGAAACCCGCTGCAAGGCTGATAACGCTGAGGAAGGTGGC
CCGGGGGCAGGTGGAGGGGGCTGCCGGGGAGTGGACAGGAGGCACTGGGT
ATCTGAGTGCAAGGCCAAGCAGTCCTATGTGCGGGCATTGACCGCTGATG
CCCAGGGCCGTGTGGGCTGGCGATGGATTCGAATTGACACTGCCTGCGTC
TGCACACTCCTCAGCCGGACTGGCCGGGCC
```

The amino acid sequence of the signal peptide for the NT-4 sequence is substantially as set out in SEQ ID NO. 51, as follows:

[SEQ ID No: 51]
```
MLPLPSCSLPILLLFLLPSVPIES
```

The nucleic acid sequence of this signal peptide is substantially as set out in SEQ ID NO. 52, as follows:

[SEQ ID No: 52]
```
ATGCTCCCTCTCCCCTCATGCTCCCTCCCCATCCTCCTCCTTTTCCTCCT
CCCCAGTGTGCCAATTGAGTCC
```

The amino acid sequence of the propeptide for this NT-4 sequence is substantially as set out in SEQ ID NO. 53, as follows:

[SEQ ID No: 53]
```
QPPPSTLPPFLAPEWDLLSPRVVLSRGAPAGPPLLFLLEAGAFRESAGAP
ANRSRR
```

The nucleic acid sequence of this propeptide is substantially as set out in SEQ ID NO. 54, as follows:

[SEQ ID No: 54]
CAACCCCCACCCTCAACATTGCCCCCTTTTCTGGCCCCTGAGTGGGACCT

TCTCTCCCCCCGAGTAGTCCTGTCTAGGGGTGCCCCTGCTGGGCCCCCTC

TGCTCTTCCTGCTGGAGGCTGGGGCCTTTCGGGAGTCAGCAGGTGCCCCG

GCCAACCGCAGCCGGCGT

The amino acid sequence of the mature protein sequence for this NT-4 sequence is substantially as set out in SEQ ID NO. 55, as follows:

[SEQ ID No: 55]
GVSETAPASRRGELAVCDAVSGWVTDRRTAVDLRGREVEVLGEVPAAGGS

PLRQYFFETRCKADNAEEGGPGAGGGGCRGVDRRHWVSECKAKQSYVRAL

TADAQGRVGWRWIRIDTACVCTLLSRTGRA

The nucleic acid coding sequence of this mature NT-4 protein is substantially as set out in SEQ ID NO. 56, as follows:

[SEQ ID No: 56]
GGGGTGAGCGAAACTGCACCAGCGAGTCGTCGGGGTGAGCTGGCTGTGTG

CGATGCAGTCAGTGGCTGGGTGACAGACCGCCGGACCGCTGTGGACTTGC

GTGGGCGCGAGGTGGAGGTGTTGGGCGAGGTGCCTGCAGCTGGCGGCAGT

CCCCTCCGCCAGTACTTCTTTGAAACCCGCTGCAAGGCTGATAACGCTGA

GGAAGGTGGCCCGGGGCAGGTGGAGGGGGCTGCCGGGGAGTGGACAGGA

GGCACTGGGTATCTGAGTGCAAGGCCAAGCAGTCCTATGTGCGGGCATTG

ACCGCTGATGCCCAGGGCCGTGTGGGCTGGCGATGGATTCGAATTGACAC

TGCCTGCGTCTGCACACTCCTCAGCCGGACTGGCCGGGCC

Accordingly, in one preferred embodiment, the second coding sequence encodes neurotrophin-4 (NT-4), which may comprise an amino acid sequence substantially as set out in SEQ ID NO: 49 or 55, or fragment or variant thereof. Thus, the second coding sequence may comprise a nucleotide sequence substantially as set out in SEQ ID No: 50 or 56, or a fragment or variant thereof.

Most preferred agonists of the TrkB receptor, however, include prepro-brain derived neurotrophic factor (pre-pro-BDNF), pro-BDNF or mature BDNF (mBDNF). BDNF is initially synthesised as the precursor protein, preproBDNF, by ribosomes found on endoplasmic reticulum. There are at least 17 known splice variants encoded by the human preproBDNF gene (ENSG00000176697). Once preproBDNF has entered into the rough endoplasmic reticulum, preproBDNF is converted into proBDNF by cleavage of the signal peptide (i.e. the "pre" sequence). proBDNF is converted into mBDNF by cleavage of an additional N-terminal peptide sequence that is present on proBDNF. Both proBDNF and mBDNF are then secreted into the extracellular space, where they bind to and activate receptors on various cells, including RGCs and cochlear cells.

proBDNF preferentially binds to and activates the receptor, $p75^{NTR}$, which, when activated, induces apoptosis in RGCs and cochlear cells. Thus, in one preferred embodiment, proBDNF is an agonist of the $p75^{NTR}$ receptor. In one embodiment, the proBDNF is canonical proBDNF. Preferably, canonical proBDNF comprises an amino acid sequence referred to herein as SEQ ID NO. 15, or a fragment or variant thereof, as set out below:

[SEQ ID No: 15]
APMKEANIRGQGGLAYPGVRTHGTLESVNGPKAGSRGLTSLADTFEHVIE

ELLDEDQKVRPNEENNKDADLYTSRVMLSSQVPLEPPLLFLLEEYKNYLD

AANMSMRVRRHSDPARRGELSVCDSISEWVTAADKKTAVDMSGGTVTVLE

KVPVSKGQLKQYFYETKCNPMGYTKEGCRGIDKRHWNSQCRTTQSYVRAL

TMDSKKRIGWRFIRIDTSCVCTLTIKRGR

Preferably, in this embodiment, the second coding sequence comprises a nucleotide sequence referred to herein as SEQ ID NO. 16, or a fragment or variant thereof, as set out below:

[SEQ ID No: 16]
GCCCCCATGAAAGAAGCAAACATCCGAGGACAAGGTGGCTTGGCCTACCC

AGGTGTGCGGACCCATGGGACTCTGGAGAGCGTGAATGGGCCCAAGGCAG

GTTCAAGAGGCTTGACATCATTGGCTGACACTTTCGAACACGTGATAGAA

GAGCTGTTGGATGAGGACCAGAAAGTTCGGCCCAATGAAGAAAACAATAA

GGACGCAGACTTGTACACGTCCAGGGTGATGCTCAGTAGTCAAGTGCCTT

TGGAGCCTCCTCTTCTCTTTCTGCTGGAGGAATACAAAAATTACCTAGAT

GCTGCAAACATGTCCATGAGGGTCCGGCGCCACTCTGACCCTGCCCGCCG

AGGGGAGCTGAGCGTGTGTGACAGTATTAGTGAGTGGGTAACGGCGGCAG

ACAAAAAGACTGCAGTGGACATGTCGGGCGGGACGGTCACAGTCCTTGAA

AAGGTCCCTGTATCAAAAGGCCAACTGAAGCAATACTTCTACGAGACCAA

GTGCAATCCCATGGGTTACACAAAAGAAGGCTGCAGGGGCATAGACAAAA

GGCATTGGAACTCCCAGTGCCGAACTACCCAGTCGTACGTGCGGGCCCTT

ACCATGGATAGCAAAAAGAGAATTGGCTGGCGATTCATAAGGATAGACAC

TTCTTGTGTATGTACATTGACCATTAAAAGGGGAAGATAG

In another embodiment, the proBDNF is isoform 2 of proBDNF, which preferably comprises a Valine to methionine mutation (amino acid underlined). Preferably, isoform 2 of proBDNF comprises an amino acid sequence referred to herein as SEQ ID NO. 17, or a fragment or variant thereof, as set out below:

[SEQ ID No: 17]
APMKEANIRGQGGLAYPGVRTHGTLESVNGPKAGSRGLTSLADTFEHMIE

ELLDEDQKVRPNEENNKDADLYTSRVMLSSQVPLEPPLLFLLEEYKNYLD

AANMSMRVRRHSDPARRGELSVCDSISEWVTAADKKTAVDMSGGTVTVLE

KVPVSKGQLKQYFYETKCNPMGYTKEGCRGIDKRHWNSQCRTTQSYVRAL

TMDSKKRIGWRFIRIDTSCVCTLTIKRGR

In one embodiment, however, the agonist is not proBDNF, or a fragment or variant thereof, but instead the second coding sequence preferably comprises a nucleotide sequence which encodes mature BDNF. Mature BDNF (mBDNF) preferentially binds to, and activates, TrkB, which, when activated, promotes survival of RGCs and/or cochlear cells. Thus, mature BDNF is a most preferred agonist of TrkB. The construct according to the first aspect is advantageous because, unlike other known genetic constructs, the construct is capable of producing mature BDNF protein, which has not been mis-folded.

Thus, in one preferred embodiment, the second coding sequence comprises a nucleotide sequence which encodes mature BDNF. mBDNF is common to all 17 isoforms encoded by the gene. There 7 protein different sequences, five of which have extended signal sequences to the canonical form, and one has a canonical signal sequence, but a Valine to Methionine mutation (which is common to isoforms 2, 4, 7, 8, 9, 10, 11, 12, 13, 14 and 16). It is believed that the valine to methionine mutation reduces release of BDNF from the cell.

Preferably, mature BDNF comprises an amino acid sequence referred to herein as SEQ ID NO. 18, or a fragment or variant thereof, as set out below:

```
                                              [SEQ ID No: 18]
HSDPARRGELSVCDSISEWVTAADKKTAVDMSGGTVTVLEKVPVSKGQLK

QYFYETKCNPMGYTKEGCRGIDKRHWNSQCRTTQSYVRALTMDSKKRIGW

RFIRIDTSCVCTLTIKRGR
```

Preferably, this embodiment of the second coding sequence comprises a nucleotide sequence referred to herein as SEQ ID NO. 19, or a fragment or variant thereof, as set out below:

```
                                              [SEQ ID No: 19]
ATGACCATCCTTTTCCTTACTATGGTTATTTCATACTTTGGTTGCATGAA

GGCTGCCCCCATGAAAGAAGCAAACATCCGAGGACAAGGTGGCTTGGCCT

ACCCAGGTGTGCGGACCCATGGGACTCTGGAGAGCGTGAATGGGCCCAAG

GCAGGTTCAAGAGGCTTGACATCATTGGCTGACACTTTCGAACACGTGAT

AGAAGAGCTGTTGGATGAGGACCAGAAAGTTCGGCCCAATGAAGAAAACA

ATAAGGACGCAGACTTGTACACGTCCAGGGTGATGCTCAGTAGTCAAGTG

CCTTTGGAGCCTCCTCTTCTCTTTCTGCTGGAGGAATACAAAAATTACCT

AGATGCTGCAAACATGTCCATGAGGGTCCGGCGCCACTCTGACCCTGCCC

GCCGAGGGGAGCTGAGCGTGTGTGACAGTATTAGTGAGTGGGTAACGGCG

GCAGACAAAAAGACTGCAGTGGACATGTCGGGCGGGACGGTCACAGTCCT

TGAAAAGGTCCCTGTATCAAAAGGCCAACTGAAGCAATACTTCTACGAGA

CCAAGTGCAATCCCATGGGTTACACAAAAGAAGGCTGCAGGGGCATAGAC

AAAAGGCATTGGAACTCCCAGTGCCGAACTACCCAGTCGTACGTGCGGGC

CCTTACCATGGATAGCAAAAAGAGAATTGGCTGGCGATTCATAAGGATAG

ACACTTCTTGTGTATGTACATTGACCATTAAAAGGGGAAGATAG
```

In yet another preferred embodiment, the agonist is mBDNF with a signal peptide conjugated to its N-terminus. As discussed below, the signal peptide may be canonical signal peptide of preproBDNF, or the signal peptide of IL-2, or a de novo novel signal sequence created by the inventors.

Preferably, the second coding sequence comprises a nucleotide sequence encoding a signal peptide for the agonist of the TrkB receptor, most preferably a signal peptide for BDNF. In one preferred embodiment, the nucleotide sequence encodes the canonical signal peptide for BDNF. Preferably, this embodiment of the second coding sequence comprises a nucleotide sequence which encodes a signal peptide comprising an amino acid sequence referred to herein as SEQ ID NO. 20, or a fragment or variant thereof, as set out below:

```
                                              [SEQ ID No: 20]
MTILFLTMVISYFGCMKA
```

Preferably, this embodiment of the second coding sequence comprises a nucleotide sequence referred to herein as SEQ ID NO. 21, or a fragment or variant thereof, as set out below:

```
                                              [SEQ ID No: 21]
ATGACCATCCTTTTCCTTACTATGGTTATTTCATACTTCGGTTGCATGAA

GGCG
```

The inventors have created a series of extended signal peptides. In preferred embodiments, the nucleotide sequence encoding an isoform signal peptide for BDNF is selected from the group consisting of: isoform 2, 3, 6, 5 and 4. The nucleic acid and amino acid sequences for each of these extended signal peptides are set out below.

Isoform 2
```
                                              [SEQ ID No: 22]
MFHQVRRVMTILFLTMVISYFGCMKA

[SEQ ID No: 23]
ATGTTCCACCAGGTGAGAAGAGTGATGACCATCCTTTTCCTTACTATGGT

TATTTCATACTTCGGTTGCATGAAGGCG
```

Isoform 3 and 6
```
                                              [SEQ ID No: 24]
MQSREEEWFHQVRRVMTILFLTMVISYFGCMKA

[SEQ ID No: 25]
ATGCAGAGCCGGGAAGAGGAATGGTTCCACCAGGTGAGAAGAGTGATGAC

CATCCTTTTCCTTACTATGGTTATTTCATACTTCGGTTGCATGAAGGCG
```

Isoform 5
```
                                              [SEQ ID No: 26]
MLCAISLCARVRKLRSAGRCGKFHQVRRVMTILFLTMVISYFGCMKA

[SEQ ID No: 27]
ATGCTCTGTGCGATTTCATTGTGTGCTCGCGTTCGCAAGCTCCGTAGTGC

AGGAAGGTGCGGGAAGTTCCACCAGGTGAGAAGAGTGATGACCATCCTTT

TCCTTACTATGGTTATTTCATACTTCGGTTGCATGAAGGCG
```

Isoform 4
```
                                              [SEQ ID No: 28]
MCGATSFLHECTRLILVTTQNAEFLQKGLQVHTCFGVYPHASVWHDCASQ

KKGCAVYLHVSVEFNKLIPENGFIKFHQVRRVMTILFLTMVISYFGCMKA

[SEQ ID No: 29]
ATGTGTGGAGCCACCAGTTTTCTCCATGAGTGCACAAGGTTAATCCTTGT

TACTACTCAGAATGCTGAGTTTCTACAGAAAGGGTTGCAGGTCCACACAT

GTTTTGGCGTCTACCCACACGCTTCTGTATGGCATGACTGTGCATCCCAG

AAGAAGGGCTGTGCTGTGTACCTCCACGTTTCAGTGGAATTTAACAAACT

GATCCCTGAAAATGGTTTCATAAAGTTCCACCAGGTGAGAAGAGTGATGA

CCATCCTTTTCCTTACTATGGTTATTTCATACTTCGGTTGCATGAAGGCG
```

Accordingly, in preferred embodiments, the second coding sequence comprises a nucleotide sequence encoding a signal sequence peptide referred to herein as any one of SEQ ID NO. 23, 25, 27 or 29. Preferably, the signal peptide comprises an amino acid sequence referred to herein as any one of SEQ ID NO. 22, 24, 26 or 28.

The inventors have also created various embodiments of novel signal peptides for the agonist, preferably BDNF.

These signal peptides increase the level of basicity of the N-terminal section (with added lysine (K) and arginine (R) residues) and the proceeding hydrophobic region (with additions of leucine (L) residues), which increase secretion of BDNF compared to levels observed with the wild-type canonical signal sequence.

a) QTA003P (IL-2 signal)
[SEQ ID No: 30]
MYRMQLLSCIALSLALVTNS

[SEQ ID No: 31]
ATGTACAGGATGCAACTCCTGTCTTGCATTGCACTAAGTCTTGCACTTGT

CACAAACAGT b) QTA004P
[SEQ ID No: 32]
MKRRVMIILFLTMVISYFGCMK

[SEQ ID No: 33]
ATGAAAAGAAGAGTGATGATCATCCTTTTCCTTACTATGGTTATTTCATA

CTTCGGTTGCATGAAGAGCG c) QTA009P (modified IL-2)
[SEQ ID No: 34]
MRRMQLLLLIALSLALVTNS

[SEQ ID No: 35]
ATGAGGAGGATGCAACTCCTGCTCCTGATTGCACTAAGTCTTGCACTTGT

CACAAACAGT d) QTA010P
[SEQ ID No: 36]
MRRMQLLLLTMVISYFGCMKA

[SEQ ID No: 37]
ATGAGGAGGATGCAACTCCTGCTCCTGACTATGGTTATTTCATACTTCGG

TTGCATGAAGGCG e) QTA0012P
[SEQ ID No: 38]
MRILLLTMVISYFGCMKA

[SEQ ID No: 39]
ATGAGAATCCTTCTTCTTACTATGGTTATTTCATACTTCGGTTGCATGAA

GGCG f) QTA0013P
[SEQ ID No: 40]
MRRILFLTMVISYFGCMKA

[SEQ ID No: 41]
ATGAGAAGAATCCTTTTCCTTACTATGGTTATTTCATACTTCGGTTGCAT

GAAGGCG g) QTA0014P
[SEQ ID No: 42]
MRRFLFLLVISYFGCMKA

[SEQ ID No: 43]
ATGAGGAGGTTCCTTTTCCTTCTTGTATTTCATACTTCGGTTGCATGAA

GGCG i) QTA0015P
[SEQ ID No: 44]
MRRFLFLLYFGCMKA

[SEQ ID No: 45]
ATGAGGAGGTTCCTTTTCCTTCTTTACTTCGGTTGCATGAAGGCG

FIG. 6 shows nucleotide and amino acid sequences for further preferred embodiments of signal peptide used in the construct of the invention to boost secretion of the agonist, preferably BDNF. The second residue in the signal peptide is threonine (T) which is preferably replaced by one or more basic residue, such as lysine (K) or arginine (R). The next stretch of residues in the signal peptide including isoleucine (I), leucine (L), phenylalanine (F) and Leucine (L) is preferably replaced by one or more hydrophobic residues.

Accordingly, in preferred embodiments, the second coding sequence comprises a nucleotide sequence encoding a signal sequence peptide referred to herein as any one of SEQ ID NO. 31, 33, 35, 37, 39, 41, 43, 45, 61, 63, 65, 67, 69, 71, 73, 75, 77, 79, 81, 83, 85, 87, 89, 91, 93, 95, 97, 99, lot or 103. Preferably, the signal peptide comprises an amino acid sequence referred to herein as any one of SEQ ID NO. 30, 32, 34, 36, 38, 40, 42, 44, 60, 62, 64, 66, 68, 70, 72, 74, 76, 78, 80, 82, 84, 86, 88, 90, 92, 94, 96, 98, 100 or 102.

Accordingly, it will be appreciated that the inventors have modified the BDNF gene sequence by removal of the pro-sequence, which also has never been achieved before, with the result of generated properly folded mature BDNF, combined with the introduction of completely novel signal peptides, which significantly boost BDNF production and release above that ever achieved with the endogenous sequence.

Preferably, the genetic construct comprises left and/or right Inverted Terminal Repeat sequences (ITRs). Preferably, each ITR is disposed at the 5' and/or 3' end of the construct. An ITR can be specific to a virus (e.g. AAV or lentivirus) serotype, and can be any sequence, so long as it forms a hairpin loop in its secondary structure.

The DNA sequence of one embodiment (left ITR from a commercially available AAV plasmid) of the ITR is represented herein as SEQ ID No: 46, as follows:

[SEQ ID NO: 46]
CCTGCAGGCAGCTGCGCGCTCGCTCGCTCACTGAGGCCGCCCGGGCGTCG

GGCGACCTTTGGTCGCCCGGCCTCAGTGAGCGAGCGAGCGCGCAGAGAGG

GAGTGGCCAACTCCATCACTAGGGGTTCCT

The DNA sequence of another embodiment (right ITR from a commercially available AAV plasmid) of the ITR is represented herein as SEQ ID No: 47, as follows:

[SEQ ID NO: 47]
AGGAACCCCTAGTGATGGAGTTGGCCACTCCCTCTCTGCGCGCTCGCTCG

CTCACTGAGGCCGGGCGACCAAAGGTCGCCCGACGCCCGGGCTTTGCCCG

GGCGGCCTCAGTGAGCGAGCGAGCGCGCAGCTGCCTGCAGG

From the foregoing, the skilled person will appreciate the nucleotide sequence of an embodiment of the construct of the first aspect, as well as the amino acid sequence of the encoded transgene. However, for the avoidance of doubt, the coding sequence of codon optimised 2940 bp sequence for murine TrkB receptor-viral-2A peptide-mBDNF contained within the plasmid QTA020P (and the vector QTA020V), is referred to here as SEQ ID No: 107, as follows:

[SEQ ID No: 107]
ATGAGCCCATGGCTGAAGTGGCACGGACCAGCAATGGCAAGACTGTGGGG

CCTGTGCCTGCTGGTGCTGGGCTTCTGGAGAGCCAGCCTGGCCTGTCCAA

CCTCCTGCAAGTGTAGCTCCGCCAGGATCTGGTGCACAGAGCCTTCTCCA

GGCATCGTGGCCTTTCCCCGCCTGGAGCCTAACAGCGTGGATCCCGAGAA
TATCACCGAGATCCTGATCGCCAACCAGAAGCGGCTGGAGATCATCAATG
AGGACGATGTGGAGGCCTACGTGGGCCTGAGAAACCTGACAATCGTGGAC
TCCGGCCTGAAGTTCGTGGCCTATAAGGCCTTTCTGAAGAACTCTAATCT
GAGGCACATCAACTTCACCCGCAATAAGCTGACATCTCTGAGCCGGAGAC
ACTTTCGGCACCTGGATCTGTCCGACCTGATCCTGACCGGCAATCCATTC
ACATGCTCTTGTGACATCATGTGGCTGAAGACCCTGCAGGAGACAAAGTC
TAGCCCCGATACCCAGGACCTGTACTGTCTGAACGAGTCCTCTAAGAATA
TGCCTCTGGCCAACCTGCAGATCCCTAATTGTGGACTGCCAAGCGCCCGG
CTGGCCGCACCTAACCTGACAGTGGAGGAGGGCAAGTCCGTGACACTGTC
CTGTTCTGTGGGCGGCGATCCCCTGCCTACCCTGTATTGGGACGTGGGCA
ACCTGGTGTCTAAGCACATGAATGAGACCTCCCACACACAGGGCTCTCTG
AGAATCACAAATATCAGCTCCGACGATAGCGGCAAGCAGATCTCTTGCGT
GGCAGAGAACCTGGTGGGAGAGGATCAGGACAGCGTGAATCTGACCGTGC
ACTTCGCCCCCACCATCACATTTCTGGAGTCTCCTACCAGCGATCACCAC
TGGTGCATCCCCTTCACAGTGCGGGAAACCCAAAGCCCGCCCTGCAGTG
GTTTTACAACGGCGCCATCCTGAATGAGTCCAAGTATATCTGTACCAAGA
TCCACGTGACCAACCACACAGAGTACCACGGCTGCCTGCAGCTGGATAAT
CCCACCCACATGAACAATGGCGACTACACACTGATGGCCAAGAACGAGTA
TGGCAAGGACGAGAGGCAGATCAGCGCCCACTTCATGGGCCGCCCTGGAG
TGGATTATGAGACCAACCCTAATTACCCAGAGGTGCTGTATGAGGACTGG
ACCACACCTACCGATATCGGCGACACCACAAACAAGTCTAATGAGATCCC
AAGCACAGATGTGGCCGACCAGTCTAACAGGGAGCACCTGAGCGTGTACG
CAGTGGTGGTCATCGCCTCCGTGGTGGGCTTCTGCCTGCTGGTCATGCTG
CTGCTGCTGAAGCTGGCCCGCCACTCTAAGTTTGGCATGAAGGGCCCAGC
CTCCGTGATCTCTAATGACGATGACAGCGCCAGCCCCCTGCACCACATCA
GCAACGGCTCCAATACCCCTTCTAGCTCCGAGGGCGGCCCAGATGCCGTG
ATCATCGGCATGACAAAGATCCCCGTGATCGAGAACCCTCAGTACTTCGG
CATCACCAATTCCCAGCTGAAGCCTGACACATTTGTGCAGCACATCAAGC
GGCACAACATCGTGCTGAAGAGGGAACTGGGAGAGGGAGCCTTCGGCAAG
GTGTTTCTGGCCGAGTGCTATAACCTGTGCCCAGAGCAGGATAAGATCCT
GGTGGCCGTGAAGACCCTGAAGGATGCCAGCGACAACGCCCGGAAGGACT
TCCACAGAGAGGCCGAGCTGCTGACAAATCTGCAGCACGAGCACATCGTG
AAGTTTTACGGCGTGTGCGTGGAGGGCGACCCTCTGATCATGGTGTTCGA
GTATATGAAGCACGGCGATCTGAACAAGTTTCTGAGAGCACACGGACCAG
ATGCCGTGCTGATGGCAGAGGGAAATCCCCCTACCGAGCTGACACAGTCT
CAGATGCTGCACATTGCACAGCAGATTGCAGCAGGAATGGTGTACCTGGC
CAGCCAGCACTTCGTGCACAGGGATCTGGCAACCAGAAACTGCCTGGTGG
GAGAGAATCTGCTGGTGAAGATCGGCGACTTTGGCATGTCCCGGGACGTG
TACTCTACCGACTACTATAGAGTGGGCGGCCACACAATGCTGCCCATCAG
GTGGATGCCACCCGAGAGCATCATGTATCGCAAGTTCACCACAGAGTCTG

ACGTGTGGAGCCTGGGCGTGGTGCTGTGGGAGATCTTTACCTACGGCAAG
CAGCCTTGGTATCAGCTGTCCAACAATGAAGTGATCGAGTGTATTACACA
GGGACGCGTGCTGCAGAGGCCACGCACATGCCCCCAGGAGGTGTACGAGC
TGATGCTGGGCTGTTGGCAGCGGGAGCCACACACCAGAAAGAACATCAAG
AGCATCCACACACTGCTGCAGAATCTGGCCAAGGCCTCCCCCGTGTATCT
GGACATCCTGGGCAGCGGAGCTACTAACTTCAGCCTGCTGAAGCAGGCTG
GAGACGTGGAGGAGAACCCTGGACCTATGAGAATCCTTCTTCTTACTATG
GTTATTTCATACTTCGGTTGCATGAAGGCGCACTCCGACCCTGCCCGCCG
TGGGGAGCTGAGCGTGTGTGACAGTATTAGCGAGTGGGTCACAGCGGCAG
ATAAAAAGACTGCAGTGGACATGTCTGGCGGGACGGTCACAGTCCTAGAG
AAAGTCCCGGTATCCAAAGGCCAACTGAAGCAGTATTTCTACGAGACCAA
GTGTAATCCCATGGGTTACACCAAGGAAGGCTGCAGGGGCATAGACAAAA
GGCACTGGAACTCGCAATGCCGAACTACCCAATCGTATGTTCGGGCCCTT
ACTATGGATAGCAAAAAGAGAATTGGCTGGCGATTCATAAGGATAGACAC
TTCCTGTGTATGTACACTGACCATTAAAAGGGGAAGATAG

The coding sequence of codon optimised 2943 bp sequence for human TrkB receptor-viral-2A peptide-mBDNF contained within the plasmid QTA029P (and the vector QTA029V), is referred to here as SEQ ID No: 108, as follows:

[SEQ ID No: 108]
ATGTCATCTTGGATCCGCTGGCACGGGCCAGCGATGGCCCGATTGTGGGG
CTTCTGCTGGCTTGTTGTAGGCTTCTGGCGCGCGGCGTTCGCGTGTCCGA
CCTCTTGCAAATGCTCAGCAAGCCGAATTTGGTGCTCAGACCCTAGTCCA
GGAATTGTTGCATTCCCCCGACTGGAACCAAACTCCGTCGACCCGGAGAA
TATAACTGAGATATTTATTGCAAATCAAAAACGCCTTGAAATCATTAACG
AGGATGACGTGGAGGCCTACGTTGGTTTGAGAAATCTTACTATTGTCGAC
TCCGGACTTAAATTTGTAGCTCATAAAGCCTTCCTGAAGAACTCTAATCT
GCAGCACATTAATTTCACGAGAAATAAGCTGACCAGCTTGTCCCGGAAGC
ATTTCCGCCATCTCGACCTGAGCGAGCTCATACTGGTCGGAAACCCATTT
ACGTGCTCCTGTGACATCATGTGGATCAAAACTCTGCAAGAGGCGAAAAG
TAGTCCGGATACCCAAGACCTTTACTGTCTTAATGAAAGCTCAAAAAATA
TCCCGCTGGCCAACCTGCAGATACCGAACTGCGGACTTCCTAGTGCGAAT
TTGGCTGCCCCAAATCTTACCGTCGAAGAAGGCAAATCAATCACGCTTTC
TTGTTCTGTAGCTGGAGATCCAGTGCCTAATATGTATTGGGACGTGGGTA
ACCTCGTCTCAAAACATATGAACGAAACGAGCCACACCCAGGGCTCTTTG
CGGATAACAAACATCTCCTCTGATGATTCTGGAAAGCAAATCAGTTGCGT
AGCTGAAAATCTGGTTGGCGAAGATCAAGATTCAGTCAATCTGACAGTCC
ATTTCGCCCCAACGATCACCTTTCTGGAGAGCCCAACTAGCGATCACCAC
TGGTGTATTCCGTTTACGGTAAAAGGAAATCCAAAACCTGCACTCCAATG
GTTTTATAATGGAGCCATCTTGAATGAAAGCAAATATATCTGTACTAAAA
TCCATGTGACGAATCACACCGAGTATCACGGGTGTCTTCAATTGGATAAT

-continued
```
CCAACCCATATGAATAATGGTGATTATACTTTGATAGCGAAGAACGAATA
CGGCAAAGACGAAAAGCAAATATCCGCACATTTCATGGGTTGGCCTGGCA
TCGACGACGGTGCGAACCCGAACTACCCAGATGTTATTTACGAGGATTAT
GGGACTGCGGCAAACGACATTGGCGACACCACAAACCGAAGCAACGAGAT
ACCAAGTACTGACGTCACTGACAAAACGGGTCGAGAGCATTTGTCTGTTT
ACGCCGTTGTTGTTATCGCCTCAGTTGTCGGATTTTGCCTGTTGGTCATG
CTTTTCCTCCTGAAGCTCGCGCGACATTCCAAGTTTGGCATGAAGGGGCC
AGCAAGTGTTATATCCAATGATGATGATAGCGCTTCTCCATTGCACCACA
TAAGTAACGGCTCAAACACGCCGTCATCTAGTGAAGGTGGACCAGACGCG
GTCATTATAGGGATGACTAAAATTCCCGTAATCGAAAACCCTCAGTACTT
CGGCATAACCAACAGTCAGCTTAAACCCGATACTTTCGTGCAGCACATCA
AAAGGCACAACATAGTCCTCAAGCGCGAACTCGGGGAGGGAGCCTTCGGA
AAGGTCTTTCTTGCTGAGTGCTATAATTTGTGTCCTGAGCAGGATAAAAT
TCTTGTGGCTGTAAAAACTCTCAAAGATGCTTCCGACAACGCACGGAAGG
ATTTTCATCGGGAGGCCGAACTGTTGACGAATTTGCAGCACGAGCATATA
GTAAAGTTCTACGGGGTATGTGTTGAGGGGGACCCGTTGATTATGGTCTT
CGAGTATATGAAGCACGGGGACCTGAACAAATTTTTGCGCGCCCATGGGC
CTGATGCCGTCCTTATGGCAGAAGGGAACCCTCCAACAGAACTCACCCAG
AGTCAGATGTTGCACATAGCGCAACAGATCGCGGCCGGCATGGTTTACCT
GGCCAGTCAACACTTCGTGCATAGAGATCTTGCCACTCGCAACTGTTTGG
TCGGGGAGAACCTTCTGGTTAAGATTGGTGACTTTGGTATGTCACGAGAT
GTGTATTCCACTGACTATTACAGAGTTGGGGGTCATACAATGCTTCCTAT
TCGGTGGATGCCCCCCGAATCCATCATGTACAGAAAGTTCACGACAGAGA
GTGATGTTTGGAGTCTCGGCGTGGTGCTCTGGGAAATTTTCACATACGGA
AAGCAGCCGTGGTATCAACTTAGCAACAATGAGGTGATAGAGTGTATTAC
ACAGGGTCGGGTGTTGCAGCGCCCTCGAACGTGCCCACAAGAAGTATATG
AACTTATGCTCGGGTGCTGGCAAAGAGAACCACATATGAGAAAAAATATC
AAGGGGATACATACATTGCTTCAGAACTTGGCCAAGGCATCACCCGTCTA
CCTCGATATACTGGGCAGCGGAGCTACTAACTTCAGCCTGCTGAAGCAGG
CTGGAGACGTGGAGGAGAACCCTGGACCTATGAGAATCCTTCTTCTTACT
ATGGTTATTTCATACTTCGGTTGCATGAAGGCGCACTCCGACCCTGCCCG
CCGTGGGGAGCTGAGCGTGTGTGACAGTATTAGCGAGTGGGTCACAGCGG
CAGATAAAAAGACTGCAGTGGACATGTCTGGCGGACGGTCACAGTCCTA
GAGAAAGTCCCGGTATCCAAAGGCCAACTGAAGCAGTATTTCTACGAGAC
CAAGTGTAATCCCATGGGTTACACCAAGGAAGGCTGCAGGGGCATAGACA
AAAGGCACTGGAACTCGCAATGCCGAACTACCCAATCGTATGTTCGGGCC
CTTACTATGGATAGCAAAAAGAGAATTGGCTGGCGATTCATAAGGATAGA
CACTTCCTGTGTATGTACACTGACCATTAAAAGGGGAAGATAG
```

Hence, in a most preferred embodiment, the construct comprises a nucleotide sequence substantially as set out in SEQ ID No: 107 or 108, or a fragment or variant thereof.

The inventors have created a series of recombinant expression vectors comprising the construct of the invention.

Thus, according to a second aspect, there is provided a recombinant vector comprising the genetic construct according to the first aspect.

The recombinant vector may be a recombinant AAV (rAAV) vector. The rAAV may be a naturally occurring vector or a vector with a hybrid AAV serotype. The rAAV may be AAV-1, AAV-2, AAV-3A, AAV-3B, AAV-4, AAV-5, AAV-6, AAV-7, AAV-8, AAV-9, AAV-10, and AAV-11. Preferably, the rAAV is rAAV serotype-2.

Advantageously, recombinant AAV2 evokes a minimal immune response in host organisms and mediates long-term transgene expression that can persist in the retina for at least one year after vector administration.

The term "recombinant AAV (rAAV) vector" as used herein means a recombinant AAV-derived nucleic acid containing at least one terminal repeat sequence.

Preferred embodiments of the vector are shown in FIGS. 2-5.

The constructs and expression vectors described herein can be used to treat optic nerve disorders and a cochlear disorders, and more generally to promote nerve regeneration and survival.

Hence, according to a third aspect, there is provided the genetic construct according to the first aspect, or the recombinant vector according to the second aspect, for use as a medicament or in therapy.

According to a fourth aspect, there is provided the genetic construct according to the first aspect, or the recombinant vector according to the second aspect, for use in treating, preventing or ameliorating an optic nerve disorder or a cochlear disorder, or for promoting nerve regeneration and/or survival.

According to a fifth aspect, there is provided a method of treating, preventing or ameliorating an optic nerve disorder or a cochlear disorder in a subject, or for promoting nerve regeneration and/or survival in a subject, the method comprising administering, to a subject in need of such treatment, a therapeutically effective amount of the genetic construct according to the first aspect, or the recombinant vector according to the second aspect.

Preferably, the genetic construct or the recombinant vector according to invention are used in a gene therapy technique. The agonist encoded by the construct or vector activate the TrkB also encoded by the construct/vector to thereby promote survival of retinal ganglion cells (RGCs) or cochlear cells.

In one embodiment, the optic nerve disorder that is treated may be glaucoma, or any other pathophysiological condition which may result in loss of RGCs, such as trauma to the head or face or vascular insults, for example partial or complete loss in blood supply to the ocular structures or regions of the brain which receive input from the optic nerve.

In addition, the construct may also be used to support replacement of RGCs through introduction of untransformed or transformed stem cell into the eye or regions associated with vision in patients.

In one embodiment, the cochlear disorder which is treated may be hearing loss or deafness. The constructs and vectors of the invention significantly enhance cochlear cell sensitivity to TrkB receptor agonists due to a localised increase in both the TrkB receptor and the agonist of the receptor. The cochlear cells may be hair cells or neuronal spiral ganglion cells which send auditory signals via their axons from the ear to the brainstem. The hair cells may be inner ear hair cells or outer ear hair cells [42, 43, 44].

In another embodiment, the constructs and vectors may be used to promote nerve regeneration and/or survival.

It will be appreciated that the genetic construct according to the first aspect, or the recombinant vector according to the second aspect may be used in a medicament, which may be used as a monotherapy (i.e. use of the genetic construct according to the first aspect or the vector according to the second aspect of the invention), for treating, ameliorating, or preventing an optic nerve disorder or a cochlear disorder, or for promoting nerve regeneration and/or survival. Alternatively, the genetic construct or the recombinant vector according to the invention may be used as an adjunct to, or in combination with, known therapies for treating, ameliorating, or preventing an optic nerve disorder or a cochlear disorder, or for promoting nerve regeneration and/or survival.

The genetic construct according or the recombinant vector according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

The genetic construct or the recombinant vector according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with the genetic construct or the recombinant vector is required and which would normally require frequent administration (e.g. at least daily injection).

In a preferred embodiment, medicaments according to the invention may be administered to a subject by injection into the blood stream, a nerve or directly into a site requiring treatment. For example, the medicament may be injected at least adjacent the retina or ear. Injections may be intravenous (bolus or infusion) or subcutaneous (bolus or infusion), or intradermal (bolus or infusion).

It will be appreciated that the amount of the genetic construct or the recombinant vector that is required is determined by its biological activity and bioavailability, which in turn depends on the mode of administration, the physiochemical properties of the genetic construct or the recombinant vector and whether it is being used as a monotherapy or in a combined therapy. The frequency of administration will also be influenced by the half-life of the cyclic polypeptide within the subject being treated. Optimal dosages to be administered may be determined by those skilled in the art, and will vary with the particular genetic construct or the recombinant vector in use, the strength of the pharmaceutical composition, the mode of administration, and the advancement of the optic nerve disorder or the cochlear disorder. Additional factors depending on the particular subject being treated will result in a need to adjust dosages, including subject age, weight, gender, diet, and time of administration.

Generally, a daily dose of between 0.001 µg/kg of body weight and 10 mg/kg of body weight, or between 0.01 µg/kg of body weight and 1 mg/kg of body weight, of the cyclic polypeptide according to the invention may be used for treating, ameliorating, or preventing an optic nerve disorder or a cochlear disorder, depending upon the genetic construct or recombinant vector used.

The genetic construct or the recombinant vector may be administered before, during or after onset of the optic nerve or cochlear disorder. Daily doses may be given as a single administration (e.g. a single daily injection or inhalation of a nasal spray).

Alternatively, the genetic construct or the recombinant vector may require administration twice or more times during a day. As an example, the genetic construct or the recombinant vector may be administered as two (or more depending upon the severity of the optic nerve or cochlear disorder being treated) daily doses of between 0.07 µg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of the genetic construct or the recombinant vector according to the invention to a patient without the need to administer repeated doses.

Known procedures, such as those conventionally employed by the pharmaceutical industry (e.g. in vivo experimentation, clinical trials, etc.), may be used to form specific formulations of the genetic construct or the recombinant vector according to the invention and precise therapeutic regimes (such as daily doses of the agents and the frequency of administration). The inventors believe that they are the first to suggest a genetic construct encoding promoter operably linked to coding sequences of a TrkB receptor and a TrkB receptor agonist.

According to a sixth aspect, there is provided a pharmaceutical composition comprising the genetic construct according to the first aspect, or the recombinant vector according to the second aspect, and a pharmaceutically acceptable vehicle.

According to a seventh aspect, there is provided a method of preparing the pharmaceutical composition according to the sixth aspect, the method comprising contacting the genetic construct according to the first aspect, or the recombinant vector according to the second aspect, with a pharmaceutically acceptable vehicle.

A "subject" may be a vertebrate, mammal, or domestic animal. Hence, compositions and medicaments according to the invention may be used to treat any mammal, for example livestock (e.g. a horse), pets, or may be used in other veterinary applications. Most preferably, however, the subject is a human being.

A "therapeutically effective amount" of the genetic construct, the recombinant vector or the pharmaceutical composition is any amount which, when administered to a subject, is the amount of the aforementioned that is needed to treat glaucoma, deafness or produce the desired effect, such as promoting nerve regeneration and/or survival.

For example, the therapeutically effective amount of the genetic construct, the recombinant vector or the pharmaceutical composition used may be from about 0.01 mg to about 800 mg, and preferably from about 0.01 mg to about 500 mg. It is preferred that the amount of the genetic construct, the recombinant vector or the pharmaceutical composition is an amount from about 0.1 mg to about 250 mg, and most preferably from about 0.1 mg to about 20 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent (e.g. the genetic construct or recombinant vector according to the invention) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The genetic construct or the recombinant vector according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The genetic construct or the recombinant vector may be prepared as a sterile solid composition that may be dissolved or suspended at the time of administration using sterile water, saline, or other appropriate sterile injectable medium.

The genetic construct, the recombinant vector and the pharmaceutical composition of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The genetic construct, the recombinant vector or the pharmaceutical composition according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the sequence identified as SEQ ID No:1-108, and so on.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments:

Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity=(N/T)*100.

Alternative methods for identifying similar sequences will be known to those skilled in the art. For example, a substantially similar nucleotide sequence will be encoded by a sequence which hybridizes to DNA sequences or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in, for example, SEQ ID Nos: 3 and 5.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

According to another aspect, there is provided a genetic construct comprising a promoter operably linked to a first coding sequence, which encodes the tyrosine kinase receptor B (TrkB), and a second coding sequence, which encodes an agonist of the TrkB receptor for activating TrkB to thereby promote survival of retinal ganglion cells (RGCs), nerve cells or cochlear cells.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figure, in which:—

Figure 7:
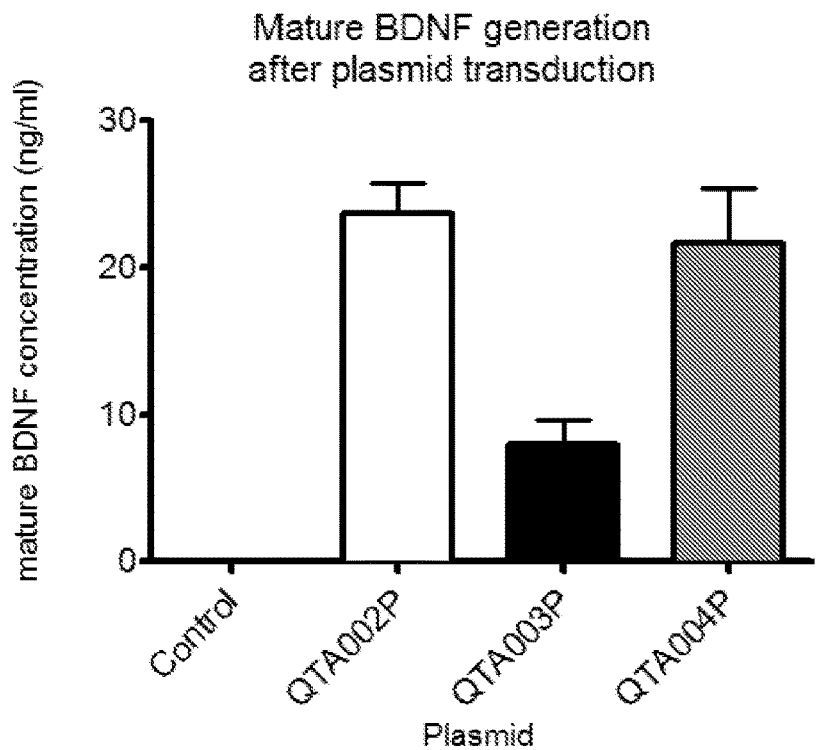
Figure 8:
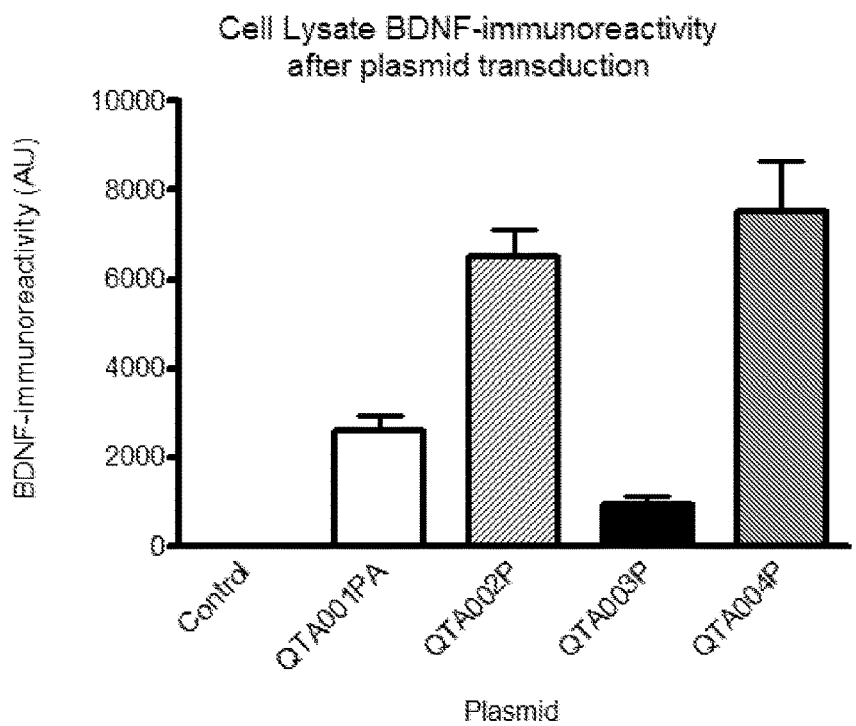
Figure 9:
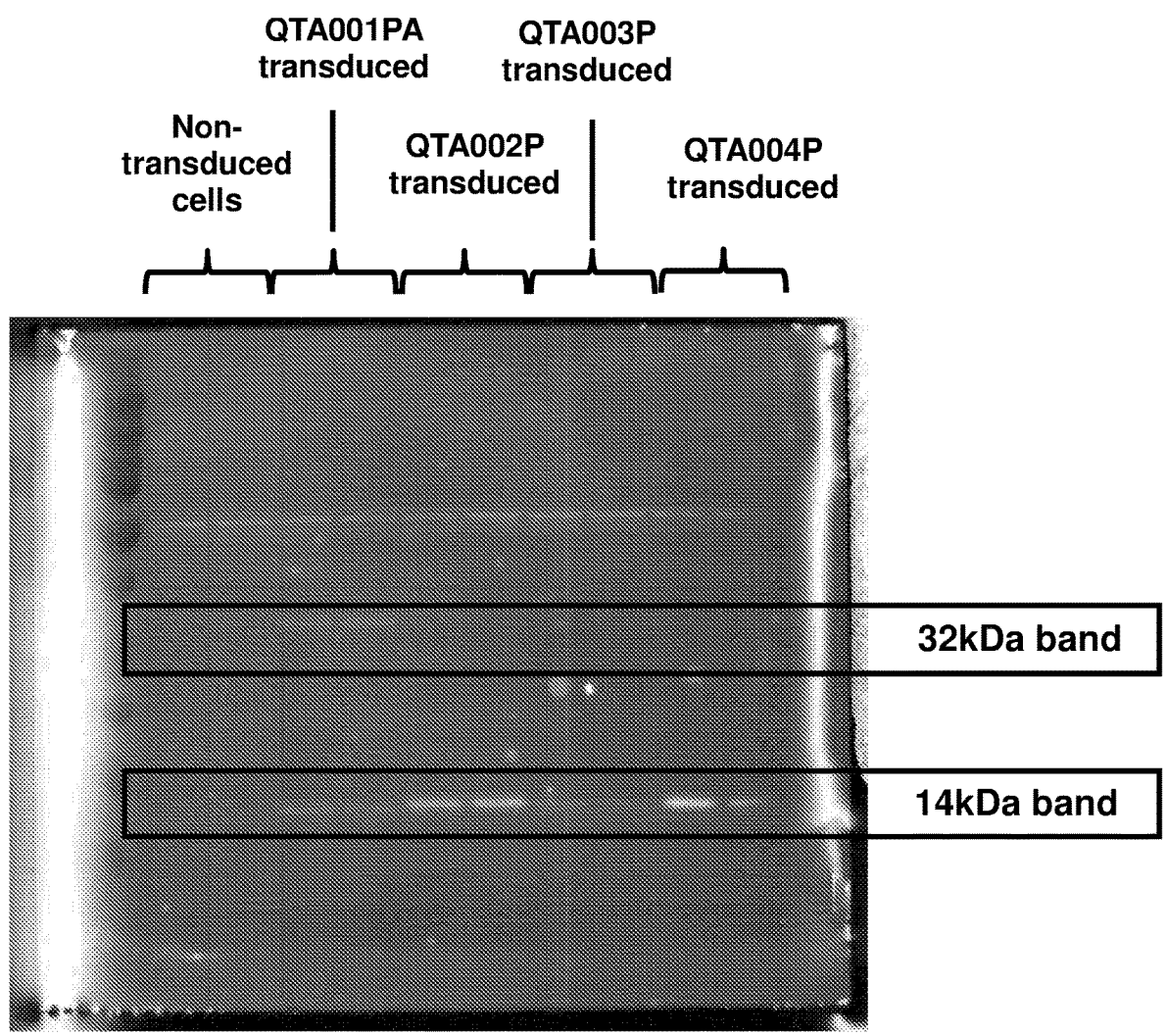
Figure 10:
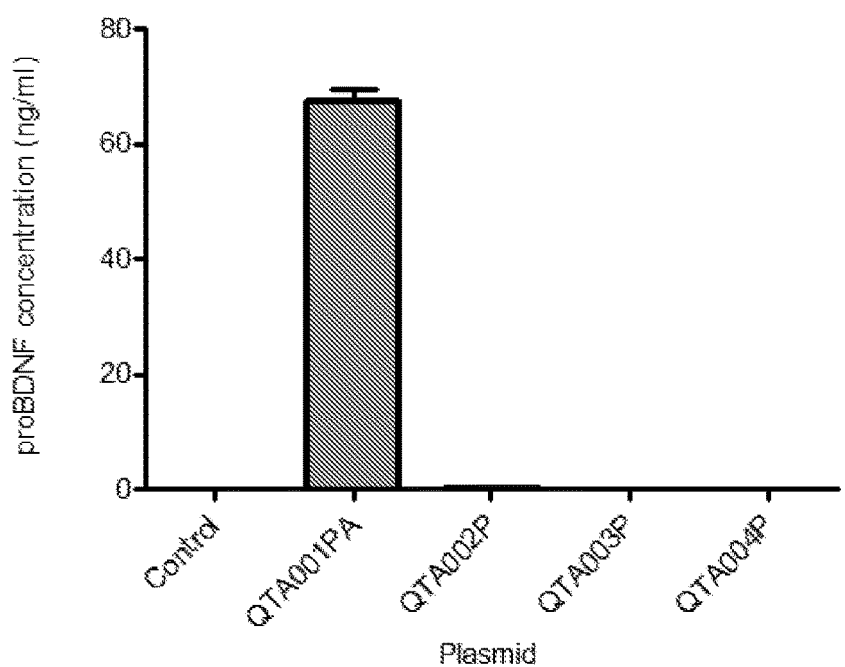
Figure 11:
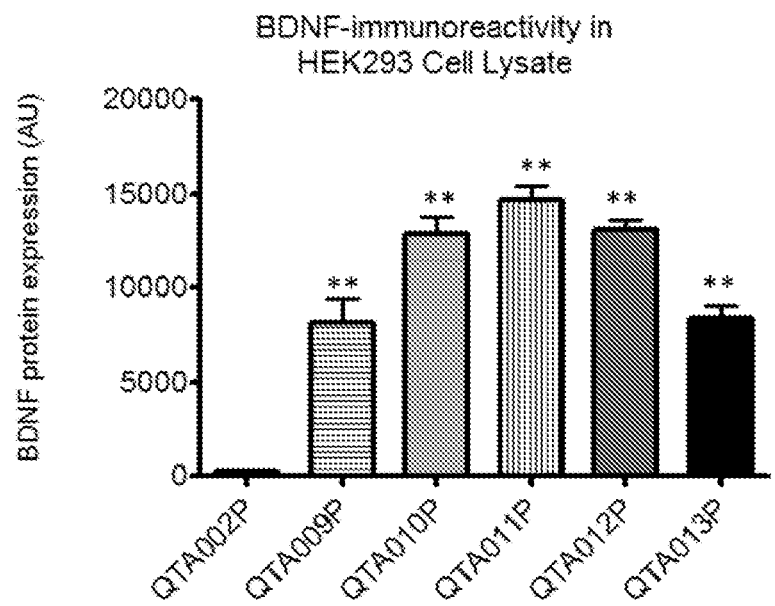
Figure 12:
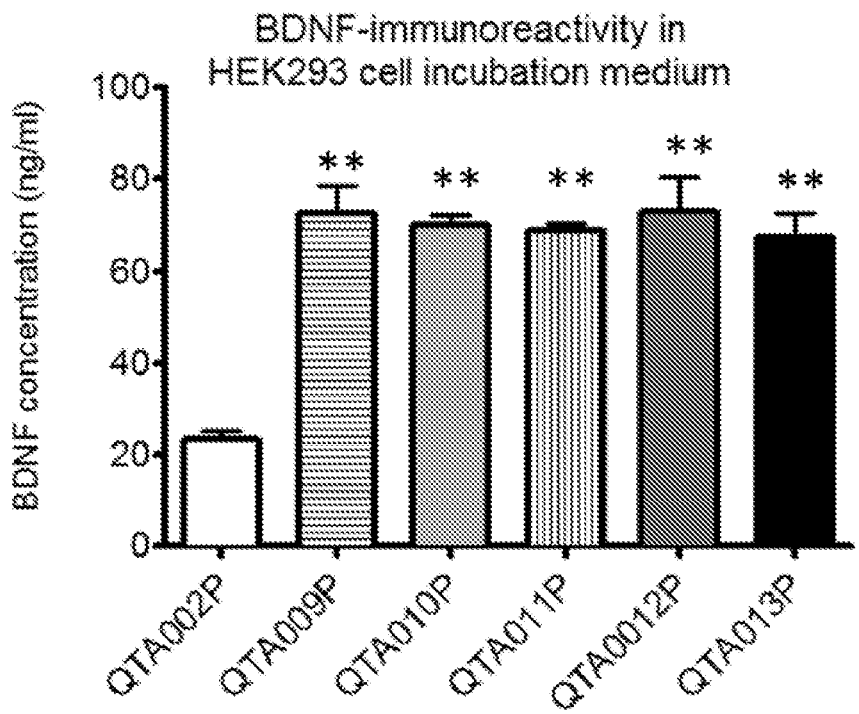
Figure 13:
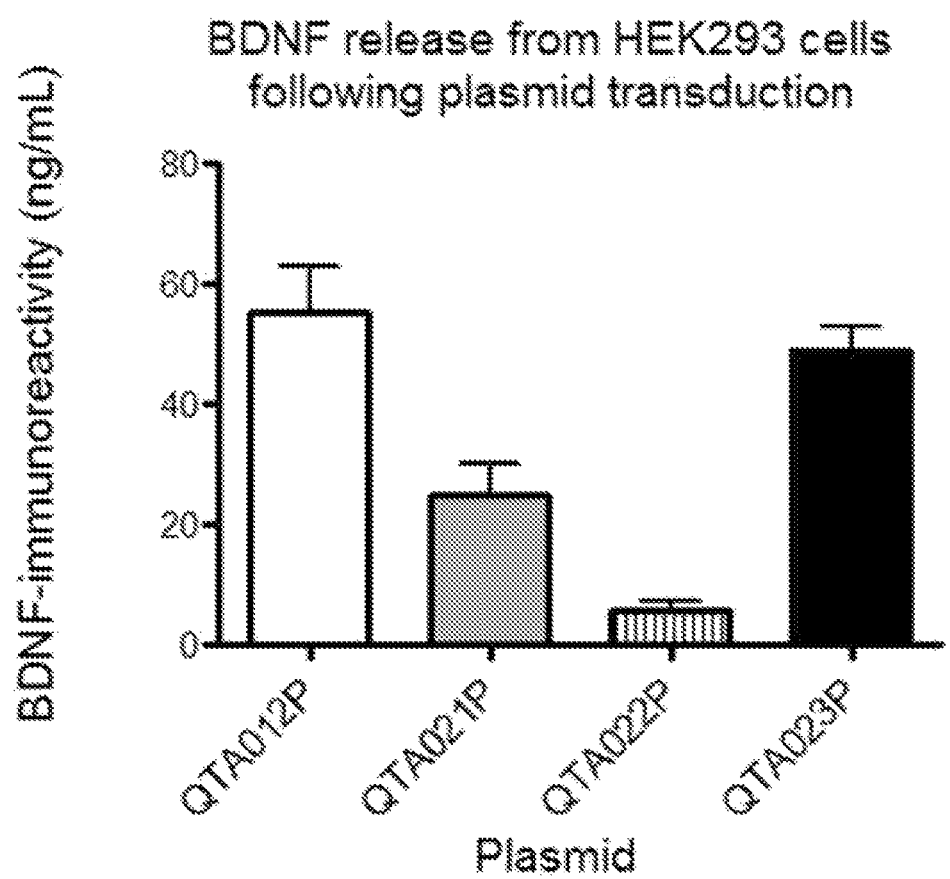
Figure 14:
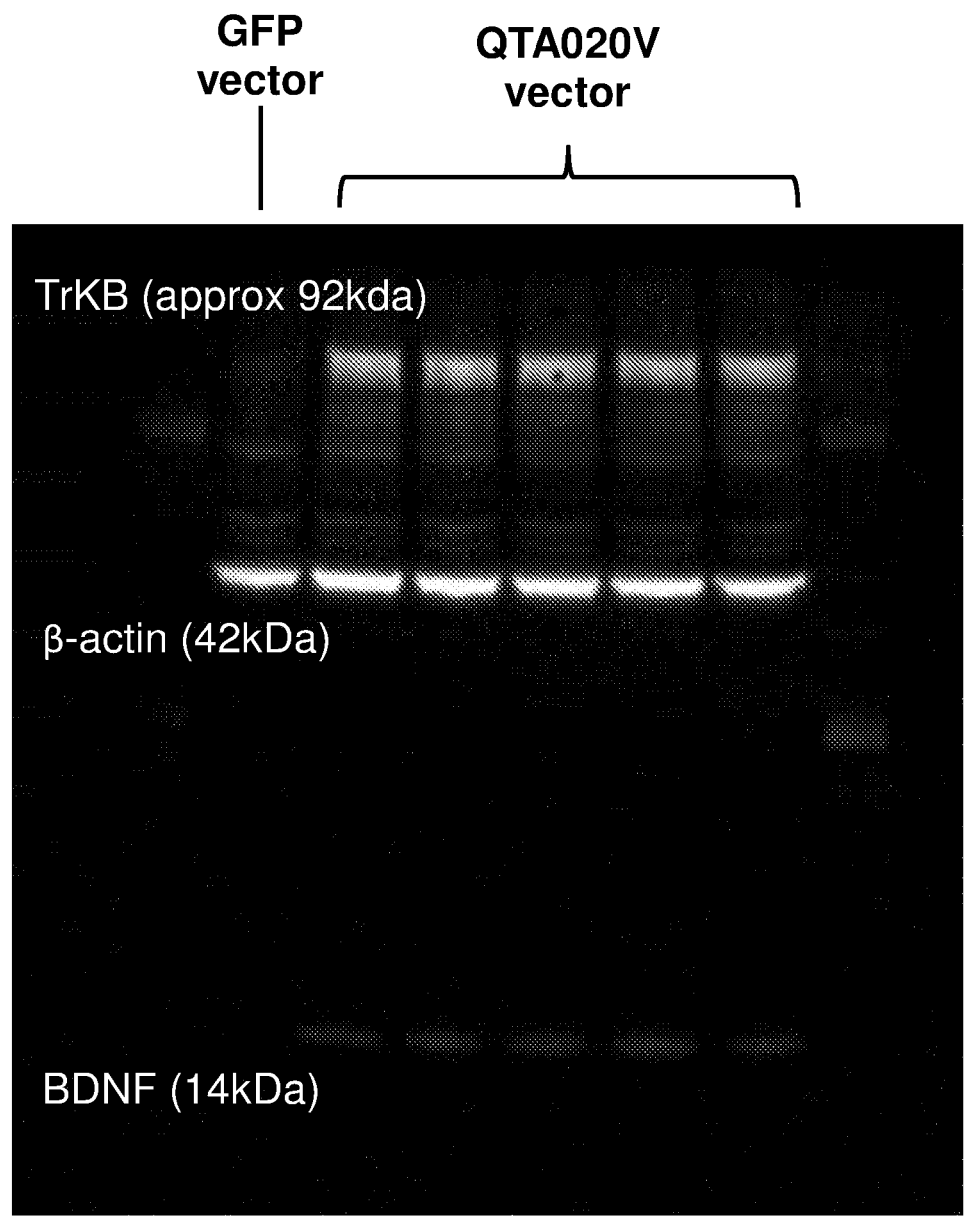
Figure 17:
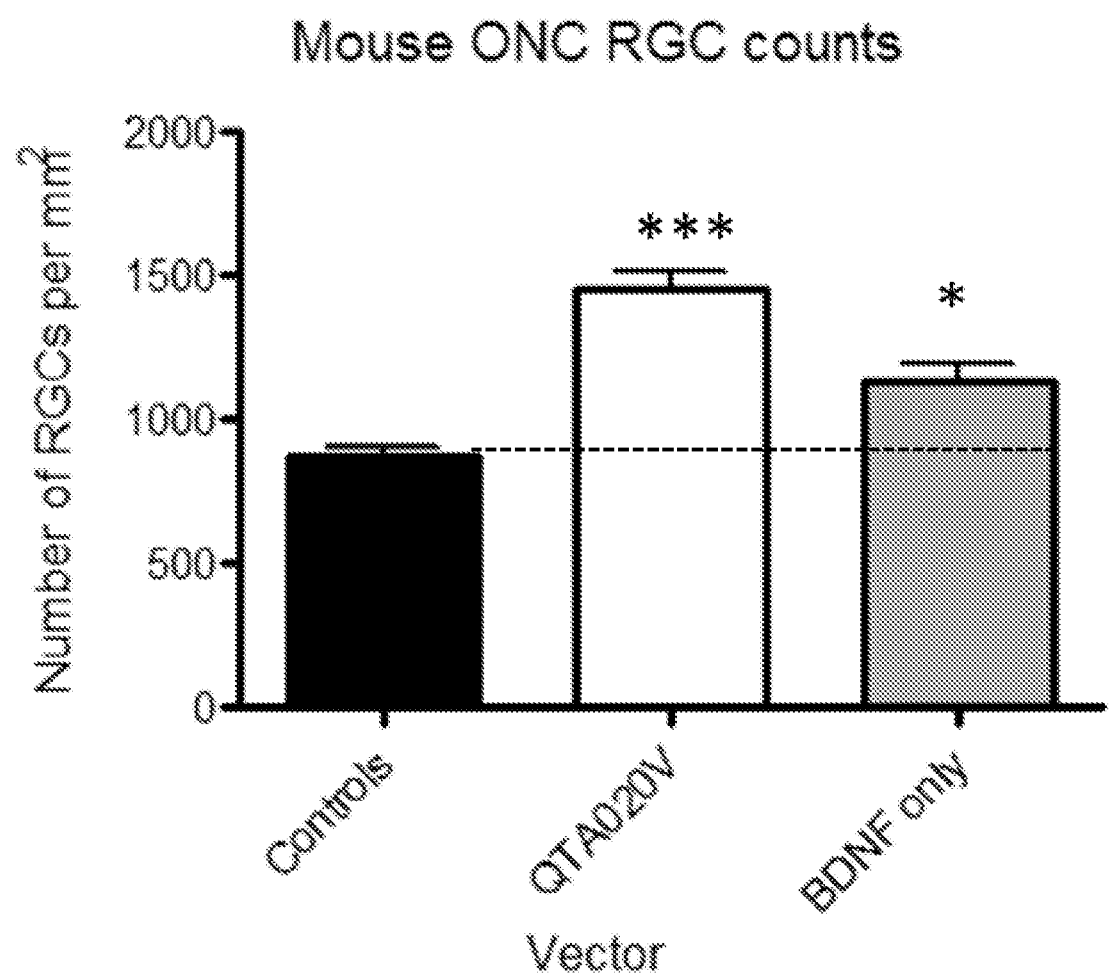

FIG. 6 shows nucleotide and amino acid sequences for different embodiments of signal peptide used in the construct of the invention. The second residue is threonine (t) which can be replaced by one or more basic residue, such as lysine (K) or arginine (R). The next stretch of residues including isoleucine (I), leucine (L), phenylalanine (F) and Leucine (L) can be replaced by one or more hydrophobic residues;

FIG. 7 shows release of BDNF from HEK293 cells using a specific ELISA at 24 hours following transduction of a plasmid (4 µg DNA/well) containing genes coding for mBDNF with differing signal peptide sequences and without the coding sequence for the extended proBDNF component (Data shown as mean±SEM for n=4);

FIG. 8 shows Western blotting results of cellular concentrations of BDNF-immunoreactive material (arbitrary units) in HEK293 cell lysates 24 hours after plasmid transduction (Data shown as mean±SEM for n=4);

FIG. 9 shows BDNF-immunoreactivity in Western blots of cell lysates showing two molecular weight bands (32 kDa and 14 kDa) when cells were transduced with QTA001PA, versus only a single 14 kDa band with QTA002P, QTA003P and QTA004P transduction;

FIG. 10 shows proBDNF concentrations in the HEK293 incubation medium as measured using a specific ELISA 24 hours after plasmid transduction using a selective proBDNF ELISA (Data shown as mean±SEM for n=4);

FIG. 11 shows BDNF expression in HEK293 cell lysate by plasmids QTA002P (endogenous canonical signal peptide sequence), and QTA009P to QTA013P. Data is shown as mean+S.E.M. *** $P<0.01$ as compared to QTA002P;

FIG. 12 shows BDNF expression in HEK293 cell incubation medium by plasmids QTA002P (endogenous canonical signal peptide sequence), and QTA009P to QTA013P. Data is shown as mean+S.E.M. *** $P<0.01$ as compared to QTA002P;

FIG. 13 shows Western Blots from HEK293 cells 24 hours after they were transduced with plasmids QTA015P (expressing BDNF and eGFP separated by an IRES spacer), QTA021P (expressing BDNF followed by eGFP separated by a functional viral-2A peptide sequence), QTA022P (expressing BDNF followed by eGFP separated by a non-functional viral-2A peptide sequence) and QTA023P (expressing eGFP followed by coding for BDNF separated by a functional viral-2A peptide sequence). Data shown as BDNF-immunoreactivity (A), eGFP-immunoreactivity (B) and the amount of BDNF released from the HEK293 cells into the incubation medium (C). Data is shown as mean+ S.E.M of the density in the bands;

FIG. 14A shows Western blot of HEK293 cell homogenates 48 hours after transfection with the QTA020V vector and showing efficient processing of the large precursor coding region which includes the TrkB receptor and BDNF separated by the viral-2A peptide sequence. FIGS. 14B and 14C show that the transgene proteins produced after vial-2A peptide cleavage have been transported to the correct intracellular compartments in HEK293 cells after processing (TrkB receptors to the cell surface and BDNF to storage vesicles prior to release);

FIG. 15A shows TrkB receptor expression and FIG. 15B shows BDNF expression in mouse retinal homogenate for the rAAV2 vector, QTA020V. Data is shown as mean+S.E.M of the density in the Western blot of mouse retina homogenates. ** $P<0.01$ as compared to naïve (un-injected animals);

FIG. 16 shows expression of TrkB (A) and BDNF (B) transgenes in mouse retinal ganglion cell layer as shown by immunocytochemistry following injection of QTA020V, a rAAV2 vector containing the coding for the TrkB receptor and BDNF, separated by the viral-2A peptide sequence; and FIG. 17 shows retinal ganglion cell (RGC) survival following optic nerve crush (ONC) in the mouse versus control animals treated with rAAV2-CAG-eGFP vector. Data shown as mean+S.E.M. for average numbers of retinal ganglion cells throughout the retina per animal as counted by Brn3A-positive cells in retinal flat-mounts. ***$P<0.001$, *$P<0.05$ as compared to controls.

EXAMPLES

Methods and Materials

Molecular Cloning and Plasmid Constructs

Codon optimisation of DNA sequences was performed using the on-line tool (http://www.idtdna.com/CodonOpt) and DNA blocks were synthesised by Integrated DNA technologies, Inc. (IDT; 9180 N. McCormick Boulevard, Skokie, Ill. 60076-2920, USA) or GenScript (860 Centennial Ave, Piscataway, N.J. 08854, USA). Cloning to make the master plasmid QTA001PA and subsequent plasmids were performed using standard molecular biology and cloning techniques.

Plasmid Scale Up and Purification

DNA Plasmids were scaled up in SURE competent cells (Agilent Technologies; cat. #200238) overnight to provide 2.29 µg/µl plasmid following maxi-prep purification. The remaining plasmids were scaled up to 500 µg scale and transduction quality with minimal endotoxin presence.

HEK293 Culture and Cell Transduction with Plasmid DNA

HEK293 cells (400,000 cells) were cultured in poly-L-lysine (10 ug/mL, Sigma-Aldrich; cat. #P1274) coated 6 well plates in 1.5 mL Dulbecco's minimum essential medium (DMEM) containing 10% foetal bovine serum (FBS), 1% penicillin and 1% streptomycin (1% Pen/Strep) until 80% confluent. The medium was then exchanged for 2 mL DMEM (no additives). Two to three hours later, an additional 0.5 ml transfection medium containing 4 µg plasmid DNA plus 10 µL lipofectamine (4 µL/mL; Thermo Fisher Scientific; cat. #12566014) was added to each well resulting in an overall volume of 2.5 ml throughout the transfection period and for supernatant collection.

BDNF Measurement by ELISA

The amount of BDNF secreted from HEK293 cells was measured in cell culture medium 24 hours after transfection. Medium was centrifuged, to remove debris, and measured using a commercial Human BDNF ELISA kit (Sigma-Aldrich, product #RAB0026). BDNF concentration was determined by comparing samples to freshly made BDNF standards.

Western Blotting for BDNF and TrkB Receptors

The amount of BDNF and TrkB-immunoreactivity within the HEK293 cells was measured by removing the DMEM incubation medium, washing the cells in cold phosphate buffered saline and the addition of 350 µL freshly prepared lysis buffer to the wells (10 ml Lysis-M reagent+1 tablet of complete Mini Protease Inhibitor Cocktail, Roche; cat. #04719964001, +100 µl Halt phosphatase inhibitor cocktail (100×), Thermo Scientific; cat. #78428). After cell homogenisation, the protein suspension was quantified using the BCA assay (Pierce BCA protein assay kit, Thermo Scientific; cat. #23227). Between 6 µg and 15 µg HEK293 cell lysate protein/lane were run down a Bis-Tris gel (12% NuPAGE Novex; cat. #NP0342BOX, Thermo Scientific) and examined by Western blotting using the primary rabbit polyclonal anti-BDNF antibodies (Santa Cruz Biotechnology Inc; product #sc-546; at 1:500 dilution), rabbit polyclonal anti-TrkB antibodies (Abcam; cat. #ab33655, used at 1:2000 dilution) or eGFP antibodies (Abcam product #ab-290 used at 1:500) which were incubated overnight. Primary antibodies were visualised with HRP conjugated anti-rabbit antibodies (Vector Laboratories; cat. #PI-1000, at 1:8000) and signal detection using ECL Prime (Amersham, GE Healthcare, UK) and an Alliance Western blot imaging system (UVItec Ltd, Cambridge, UK). For Western blots of mouse retina, eyes from vector-treated animals were homogenized in 500 µL freshly prepared lysis buffer (10 ml Lysis-M reagent+1 tablet of cOmplete Mini Protease Inhibitor Cocktail, Roche product #04719964001+100 µl Halt phosphatase inhibitor cocktail (100×), Thermo Scientific product #78428). Tissue was disrupted for 1 minute (Qiagen, TissueRuptor product #9001273) and then kept on ice for an additional 15 minutes. The protein was then analysed by Western blotting as described above.

Immunocytochemistry

HEK293 cells (70,000) were seeded on 13 mm, poly-L-lysine coated coverslips within 4 well plates and incubated in DMEM containing 10% FBS and 1% Pen/Strep in 0.5 ml medium. Once the cells had grown to 80% confluence, the medium was exchanged for 0.4 ml DMEM (no additives) for 2-3 hours then an additional 0.1 mL transfection medium (0.8 µg plasmid DNA+2 µl lipofectamine) was added so that the final volume reached 0.5 ml. Coverslips were washed twice in PBS and fixed for 30 min in 4% paraformaldehyde in 1M phosphate buffered saline (PBS) at room temperature. After three more washes in PBS, cells were blocked and permeabilized by incubation in 5% normal goat serum (NGS), 3% bovine serum albumin (BSA) and 0.3% Triton X-100 in PBS for 60 minutes at room temperature. Cells were then incubated overnight at 4° C. with commercial rabbit polyclonal antibodies for BDNF (Santa Cruz Biotechnology Inc; product #sc-546; at 1:300 dilution) or TrkB (Abcam product #ab33655, diluted 1:500) diluted in blocking solution. Staining was revealed using secondary anti-rabbit antibodies conjugated to alexa fluor 647 (Invitrogen, product #A21248 at 1:1000) for 2 hours at room temperature. Cell nuclei were also counterstained with 1 µg/ml DAPI (Thermo Scientific, product #D1306 at 1:8000). Cells were further washed three times before being mounted with FluorSave™ reagent (Calbiochem/EMD Chemicals Inc., Gibbstown, N.J., USA) prior to imaging. Imaging was carried out using a 20× objective and a Leica DM6000 epifluorescence microscope (Leica Microsystems, Wetzlar, Germany) or a Leica SP5 confocal microscope (Leica Microsystems, Wetzlar, Germany) equipped with a 63× oil objective using a 3× digital zoom and 0.5-0.8 sequential scanning z-step interval.

For immunocytochemistry of retinal structures from control or vector treated animals, carefully dissected eyes were fixed in 4% paraformaldehyde/0.1% PBS (pH 7.4) overnight and dehydrated in 30% sucrose/0.1% PBS at 4° C. (24 hours). Eyes were then embedded in silicon moulds containing optimal cutting temperature compound (OCT) (Sakura Finetek, Zoeterwoude, Netherlands) and frozen on dry ice. 13 µm sections through the dorsal-ventral/superior-inferior axis of the retina were collected onto superfrost plus slides (VWR product #631-0108), using a Bright OTF 5000 cryostat (Bright Instruments, Huntingdon, UK). Slides were washed three times in PBS, and permeabilized in 5% normal goat serum (NGS), 3% bovine serum albumin (BSA) and 0.3% Triton X-100 in PBS for 60 minutes at room temperature. Slides were then incubated overnight at 4° C. with commercial rabbit polyclonal antibodies for BDNF (Santa Cruz Biotechnology Inc product #sc-546 1:300) or TrkB (Abcam product #ab33655 1:500), diluted in blocking solution. Staining was revealed using secondary anti-rabbit antibodies conjugated to alexa fluor 647 (Invitrogen, product #A21248 at 1:1000) for 2 hours at room temperature. Retinal cell nuclei were also counterstained with 1 µg/mL DAPI (Thermo Scientific, product #D1306 at 1:8000). Slides were further washed three times before being mounted with FluorSave™ reagent (Calbiochem/EMD Chemicals Inc., Gibbstown, N.J., USA) prior to imaging. Imaging was carried out using a 20× objective and a Leica DM6000 epifluorescence microscope (Leica Microsystems, Wetzlar, Germany) or a Leica SP5 confocal microscope (Leica Microsystems, Wetzlar, Germany) equipped with a 63× oil objective using a 3× digital zoom and 0.5-0.8 sequential scanning z-step interval.

Intravitreal Injections

Following a 7-10 day acclimatisation period, mice were randomised into various study groups. They were then anaesthetized with intraperitoneal injection of ketamine (50 mg/kg) and xylazine (5 g/kg). Topical 1% tetracaine eye drops were administered on Day 1 of the study. Pupillary dilation was achieved using 1% tropicamide eye drops. Using an operating microscope, a partial-thickness scleral pilot hole was made with a 30-gauge needle to facilitate penetration of the underlying sclera, choroid, and retina by a fine metal micropipette with a tip diameter of 30 µm and a tip length of 2.5 mm. The micropipette was then connected to a 10 µl glass syringe (Hamilton Co., Reno, Nev.) prior drawing up 2 µl of vector suspensions into the pipette depending on the group. Care was taken to avoid penetration of the lens or damage to the vortex veins during intravitreal injection. The injection site was aimed approximately 3 mm posterior to the supero-temporal limbus. Injections were given slowly over 1 minute to allow diffusion of vector suspension. The right eye was left untouched and served as an internal contralateral control.

Optic Nerve Crush (ONC)

Three weeks (21 days) after vector administration, the mice were subject to the ONC procedure, left untreated or sham-crushed. Under a binocular operating scope, a small incision was made with spring scissors in the conjunctiva beginning inferior to the globe and around the eye temporally. This exposed the posterior aspect of the globe, allowing visualization of the optic nerve. The exposed optic nerve was grasped approximately 1-3 mm from the globe with cross-action forceps (Dumont #N7 cat. #RS-5027; Roboz) for 10 s, with the only pressure from the self-clamping action to press on the nerve. After 10 s the optic nerve was released, the forceps are removed and the eye rotates back into place. 7 days after ONC, animals were culled. Both eyes from each group were fixed by placing the organ in 4% paraformaldehyde/0.1% PBS (pH 7.4) overnight. Retinal flat-mounts were then prepared following dissection of the posterior eye structure from the cornea and removal of the lens. The retinal flat-mounts were post fixed for 30 minutes in 4% paraformaldehyde/0.1% PBS and washed in 0.5% Triton X-100 in PBS. Retinas were frozen at −80° C. for 10 minutes to permeate the nuclear membrane and improve antibody permeation before blocking in 10% normal donkey serum (NDS), 2% bovine serum albumin (BSA) and 2% Triton X-100 in PBS for 60 minutes at room temperature. RGCs were counterstained with antibodies against Brn3A (1:200 Santa Cruz, #sc-31984) and visualised under fluorescence microscopy using a 20× objective and a Leica DM6000 epifluorescence microscope (Leica Microsystems, Wetzlar, Germany). Higher resolution images were be obtained using a Leica SP5 confocal microscope (Leica Microsystems) equipped with a 40× oil objective using a 1.5× digital zoom and 0.5-0.8 sequential scanning z-step interval. RGC cell counts were measured by ImageJ using the image-based tool for counting nuclei plugin (ITCN) and expressed as density of RGCs/mm$^2$.

Constructs and Vectors

Figure 1:
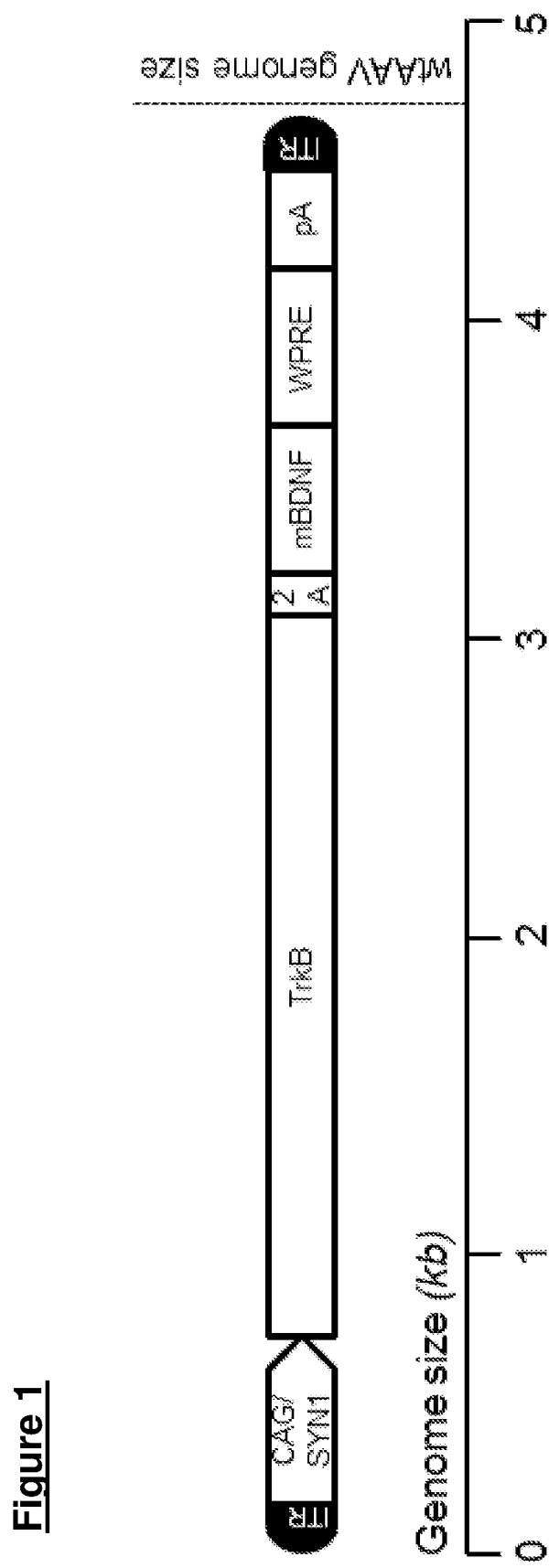
FIG. 1 is schematic of one embodiment of a genetic construct according to the invention.

The inventors have generated a genetic construct, as shown in FIG. 1, which may be used to treat a subject afflicted with an optic nerve pathology, such as glaucoma, or a cochlear pathology, or for promoting nerve regeneration and/or survival. The construct has been designed to maintain or increase the density of TrkB receptors on the cell surface of RGCs and maintain or increase signaling through the TrkB receptor pathway by concomitant production and local release of mBDNF.

The construct comprises transgenes encoding the TrkB receptor and its agonist, mature brain-derived neurotrophic factor. These transgenes are operably-linked to a single promoter, which is either the human synapsin I (SYN I) promoter or the CAG promoter. Advantageously, the construct of FIG. 1 can be placed in a rAAV2 vector without being hindered by the size of the transgenes that it encodes. This is because the construct is orientated such that the first transgene, TrkB, is linked to the viral 2A peptide sequence followed by the BDNF signal peptide and then the mature protein. This orientation also minimises immunogenicity risks because the short N-terminal amino acid sequence of the viral 2A peptide remains attached to the intracellular portion of the TrkB receptor and the residual proline amino acid from the C-terminal viral 2A sequence remains attached to the N-terminal BDNF signal peptide and is ultimately removed from the mBDNF protein following cleavage. The vector may be placed in a pharmacologically acceptable buffered solution, which may be administered to a subject.

Figure 2:
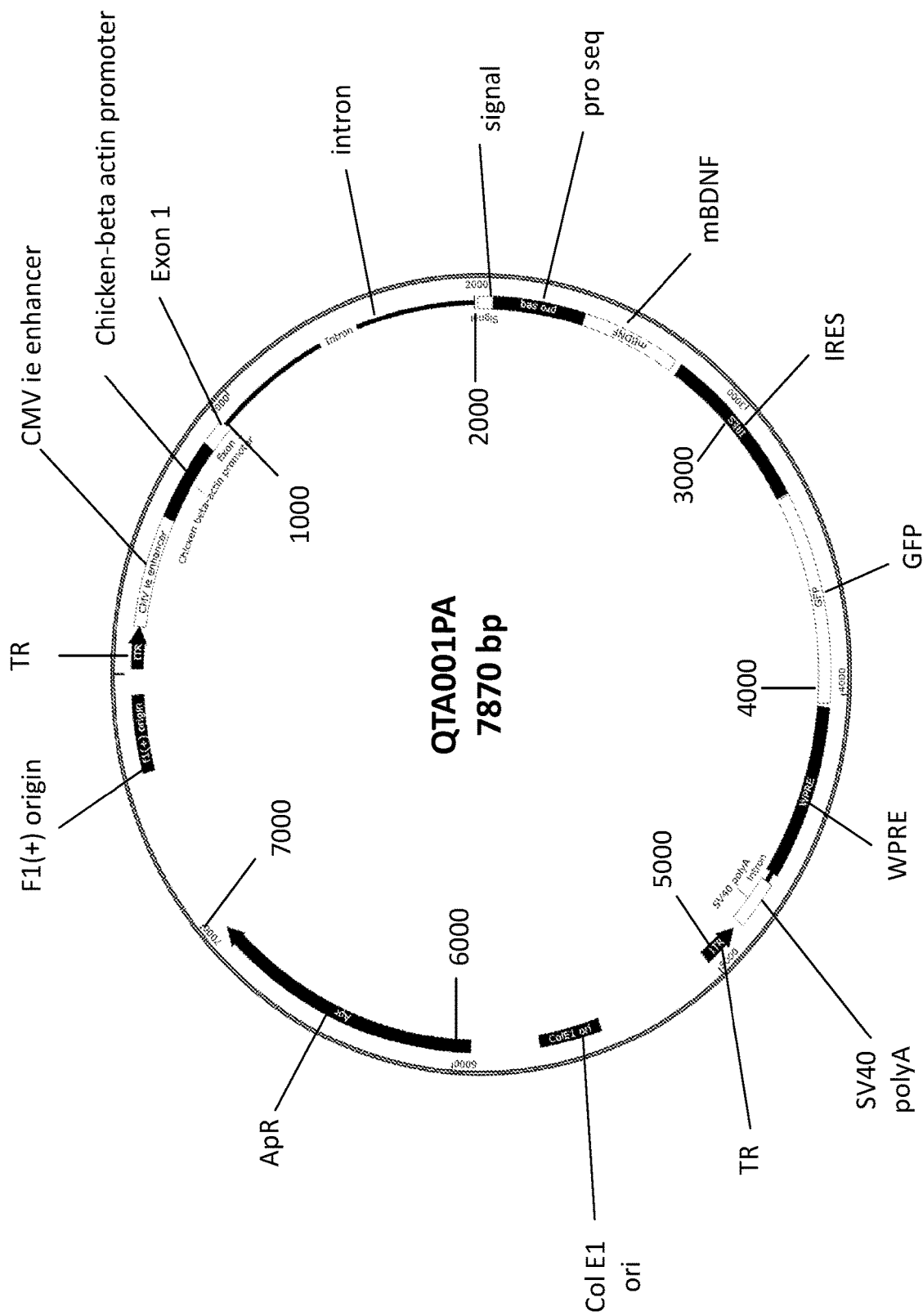
FIG. 2 is a schematic drawing of a first embodiment of a recombinant vector according to the invention known as "Plasmid QTA001PA" containing canonical signal sequence (blue) plus proBDNF (red) and mBDNF (black). It also includes an -IRES-GFP- sequence (cyan and purple)
Figure 3:
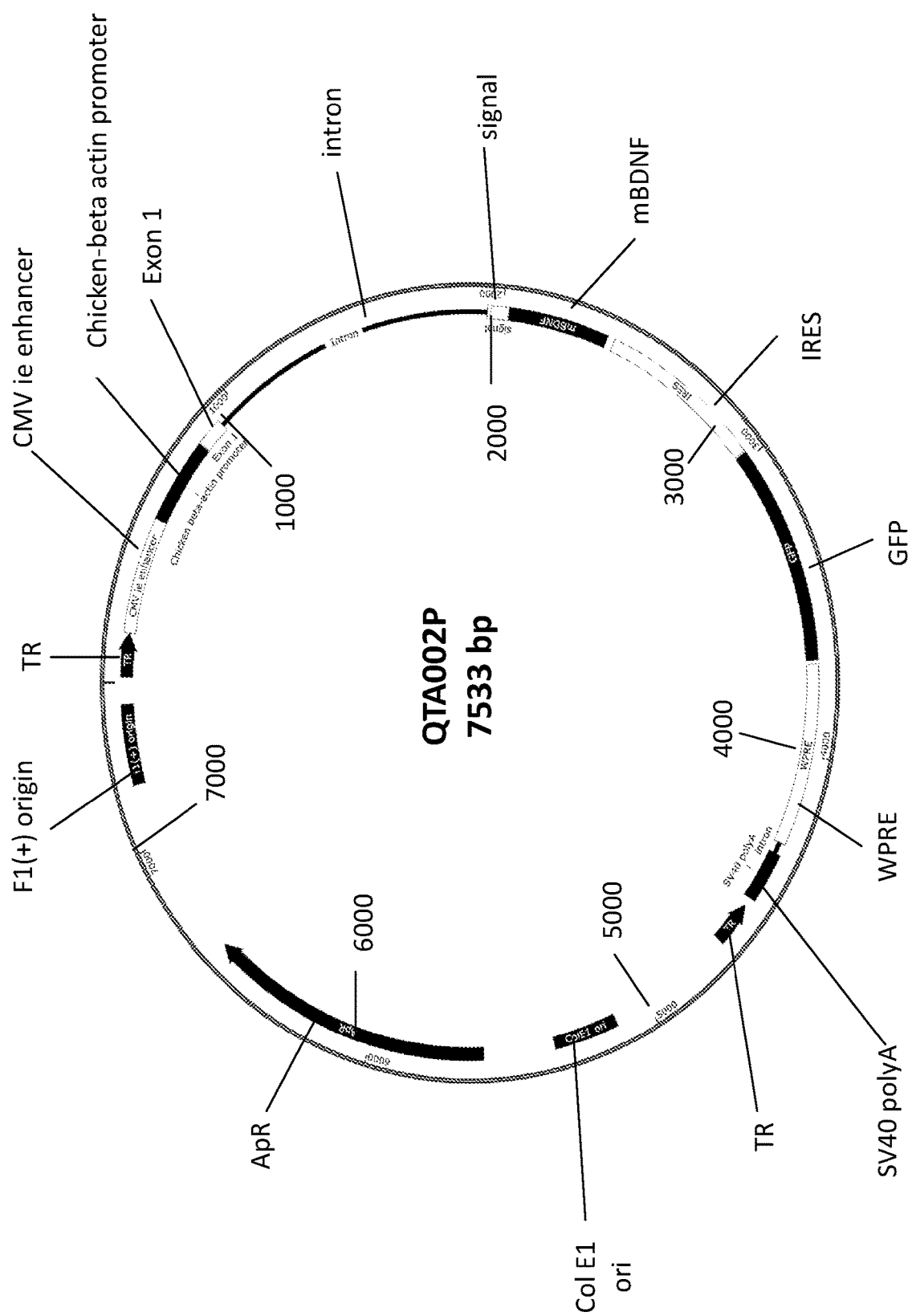
FIG. 3 is a schematic drawing of a second embodiment of the recombinant vector according to the invention known as "Plasmid QTA002P" with no proBDNF (but produces only mBDNF) and same signal sequence (blue) as QTA001PA. It also includes an -IRES-GFP- sequence (cyan and purple)
Figure 4:
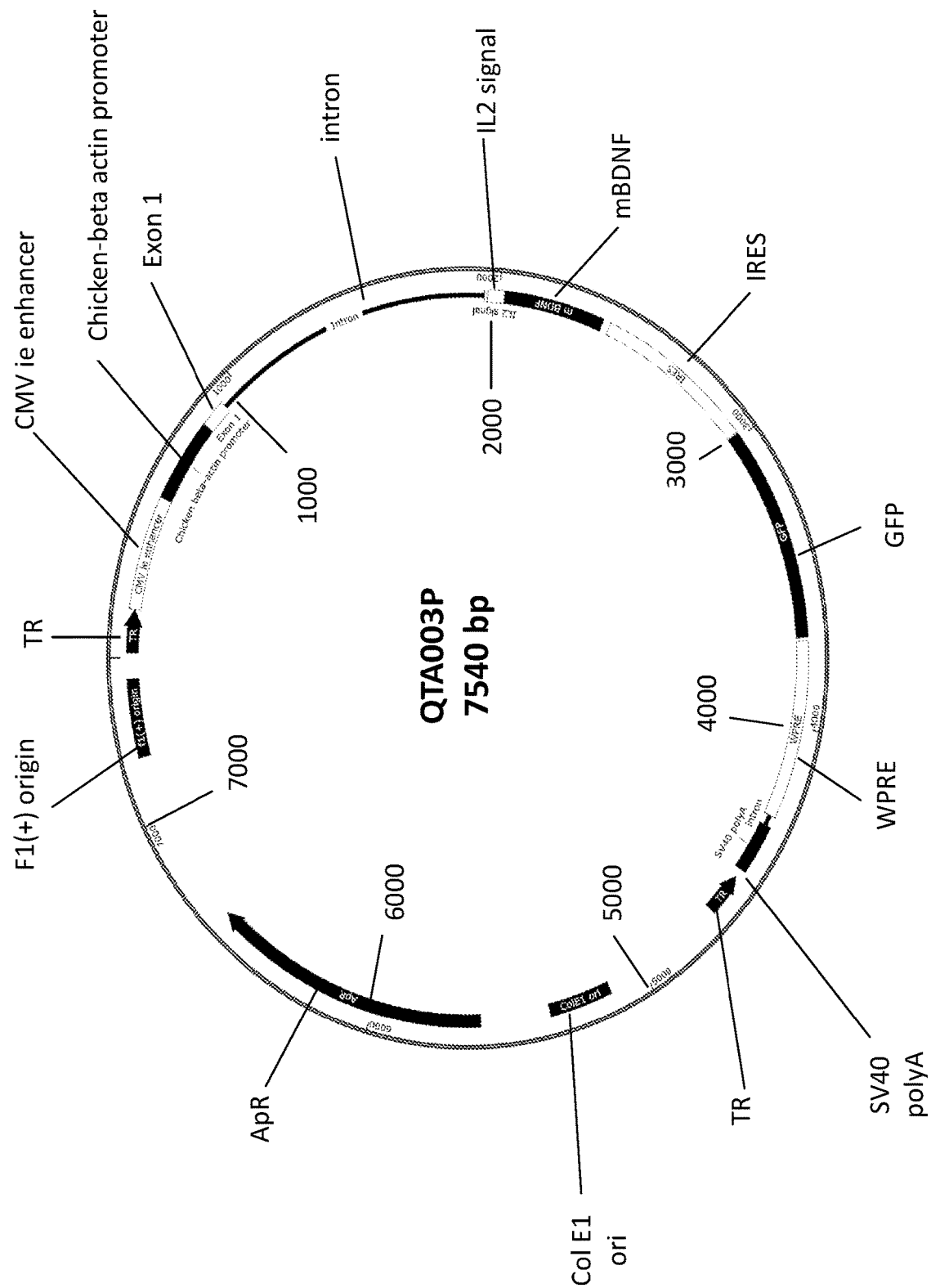
FIG. 4 is a schematic drawing of a third embodiment of the recombinant vector according to the invention known as of "Plasmid QTA003P" with no proBDNF (but produces only mBDNF) and IL-2 signal sequence (blue). It also includes an -IRES-GFP- sequence (cyan and purple)
Figure 5:
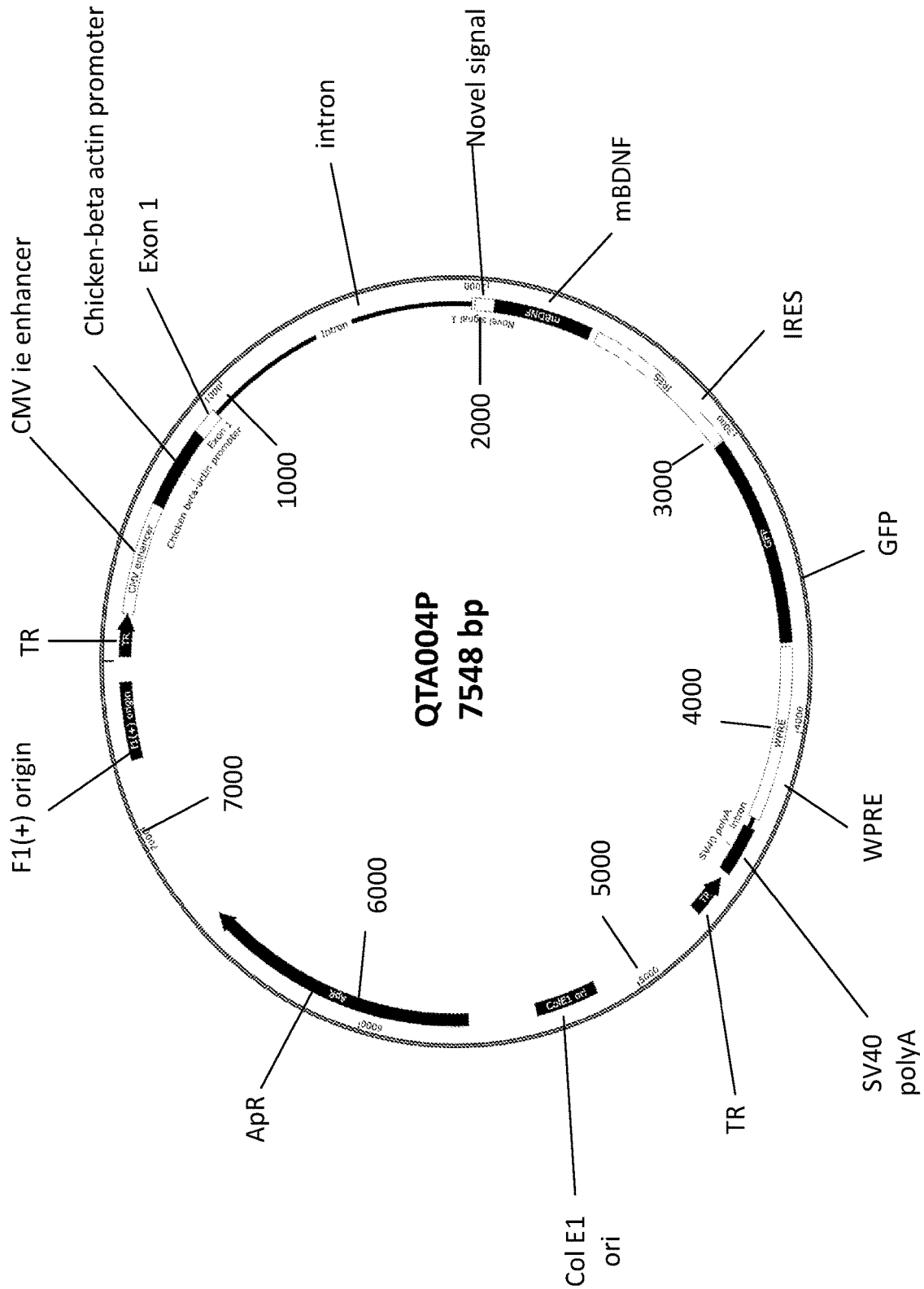
FIG. 5 is a schematic drawing of a fourth embodiment of a recombinant vector according to the invention known as "Plasmid QTA004P" with no proBDNF (but produces only mBDNF) and a novel signal sequence (blue). It also includes an -IRES-GFP- sequence (cyan and purple)

FIGS. 2-5 show various embodiments of expression vectors. FIG. 2 shows the vector known as "Plasmid QTA001PA" containing canonical signal sequence (blue) (i.e. MTILFLTMVISYFGCMKA [SEQ ID NO:20]) plus proBDNF (red) and mBDNF (black). FIG. 3 shows the vector known as "Plasmid QTA002P". It does not encode proBDNF but produces only mBDNF, and encodes the same signal sequence (blue) as QTA001PA. FIG. 4 shows the vector known as "Plasmid QTA003P" which also does not encode proBDNF but produces only mBDNF. Instead of the canonical signal sequence for mBDNF, it comprises an IL-2 signal sequence (blue). Finally, FIG. 5 shows the vector known as "Plasmid QTA004P". It does not encode proBDNF but instead produces only mBDNF. It also encodes a novel signal sequence (blue), [SEQ ID NO: 32].

The inventors have produced and investigated the construct and vector relating to the glaucoma gene therapy concept starting with the mature BDNF (mBDNF) element. They have clearly demonstrated production and release of mBDNF from HEK293 cells following lipofectamine transduction with a plasmid which contains the BDNF sequence without the proBDNF coding region (QTA002P, see FIG. 3) (see FIG. 7). The mBDNF released from the cells is the predicted 14 kDa monomer (measured using Western blotting and a commercially available antibody for BDNF) and there is no evidence for protein aggregates, as has been reported by several groups attempting to generate commercial amounts of mBDNF using yeast and other cell-based manufacturing approaches[1]. The mBDNF is therefore released in a form which can allow the protein molecules to form non-covalent dimers in order to activate TrkB receptors.

Using an ELISA for BDNF (which does not differentiate between mBDNF and the larger extended proBDNF protein), the inventors have also demonstrated that it is possible to substitute the DNA sequence coding for the endogenous canonical 18-amino acid signal peptide sequence (MTIL-FLTMVISYFGCMKA) with a novel peptide sequence (QTA004P—see FIG. 5) and release equivalent levels of BDNF into the HEK293 incubation medium following lipofectamine transduction of the cells with plasmids containing the BDNF gene (see FIG. 7).

Substitution of the endogenous signal peptide with the sequence coding for the interleukin-2 signal peptide (QTA003P—see FIG. 4) was less effective in releasing BDNF from the medium. Levels of BDNF released into the medium are currently around 1-2 nM and concentrations of this agonist are sufficient to maximally activate the specific TrkB receptors (IC50 of around 0.9 nM). Levels of BDNF release are approximately 35-fold higher (876±87 ng/mL BDNF) with the plasmid QTA001PA (see FIG. 2) which contains the combined proBDNF and mBDNF sequences and which also includes the 18-amino acid canonical signal peptide as compared to the plasmids QTA002P (see FIG. 3) and QTA004P (see FIG. 5).

Measurements of BDNF remaining in the cell by quantitative Western blotting 24 hours after lipofectamine plasmid transduction revealed lower BDNF remaining concentrations with QTA001PA than those with QTA002P and QTA004P (see FIG. 8).

Moreover, around half of the BDNF immunoreactivity in the cell lysates transduced by QTA001PA was in the form of the proBDNF (molecular weight band at 32 kDa) whereas the proBDNF band was absent in the lysates of cells transduced with QTA002P, QTA003P and QTA004P (see FIG. 9), probably because these plasmids do not contain a proBDNF extended coding sequence.

Using an ELISA specific for the proBDNF, the inventors were able to demonstrate that around 70 ng/mL (2.2 nM or 3.5%) of released BDNF-immunoreactivity from cells transduced by QTA001PA is in the form of proBDNF whilst the majority (96.5% or 876 ng/mL/63 nM) is released as mBDNF (see FIG. 10). There was no proBDNF-immunoreactivity detected from cells transduced by QTA002P, QTA003P or QTA004P which do not contain the coding sequence for the extended proBDNF.

Accordingly, it is clear that all of the plasmids are capable of producing the 14 kDa mBDNF protein, but that the amounts of mBDNF released from the HEK293 cells are largely dependent on efficiency in protein storage and packaging into secretory vesicles. The extended form of the protein, containing the combined proBDNF and mBDNF sequences, as produced with plasmid QTA001PA (FIG. 2) is therefore packaged into secretory vesicles and released into the incubation medium much more efficiently than with the smaller mBDNF sequences which appear to accumulate within the cell.

Referring to FIG. 11, it shows that substitution of the coding for the endogenous canonical signal peptide sequence, as represented in plasmid QTA002P, with novel sequences included in plasmids QTA009P to QTA013P increases the concentration of BDNF in HEK293 cells 24 hours after transduction with plasmids. FIG. 12 demonstrates that substitution of the endogenous canonical signal peptide coding sequence included in plasmid QTA002P with novel sequences (plasmids QTA009P to QTA013P) increases release of BDNF (as measured by ELISA) from HEK293 cells, as measured 24 hours after transduction with plasmids.

As shown in FIG. 13, the addition of the viral-2A peptide sequence results in efficient processing of the coding sequence for the large precursor protein into two transgenes, eGFP and BDNF. The Western blots show HEK293 cells 24 hours after they were transduced with plasmids: (i) QTA015P (expressing BDNF and eGFP separated by an IRES spacer), (ii) QTA021P (expressing BDNF followed by eGFP separated by a functional viral-2A peptide sequence), (iii) QTA022P (expressing BDNF followed by eGFP separated by a non-functional viral-2A peptide sequence) and (iv) QTA023P (expressing eGFP followed by coding for BDNF separated by a functional viral-2A peptide sequence).

The coding sequence of QTA021P (plasmid containing codon optimised sequence for mBDNF-viral-2A peptide-eGFP) is referred to here as SEQ ID No: 104, as follows:

[SEQ ID No: 104]
ATGACTATCCTGTTTCTGACAATGGTTATTAGCTATTTCGGTTGCATGAA

GGCTCACAGTGATCCCGCACGCCGCGGAGAACTTAGCGTGTGCGACAGCA

TCAGCGAGTGGGTCACCGCCGCCGATAAGAAGACCGCTGTGGATATGTCC

GGCGGGACCGTCACTGTACTCGAAAAAGTTCCAGTGAGCAAAGGCCAACT

GAAACAATATTTCTATGAAACTAAGTGCAACCCCATGGGGTACACCAAGG

AGGGCTGCCGGGGAATCGACAAGAGACACTGGAATTCCCAGTGCCGGACC

ACTCAGAGCTACGTCCGCGCCTTGACGATGGATTCAAAGAAGCGCATCGG

ATGGCGGTTCATAAGAATCGACACCAGTTGTGTGTGCACGCTGACGATAA

AACGGGGGCGGGCCCCCGTGAAGCAGACCCTGAACTTTGATTTGCTCAAG

TTGGCGGGGATGTGGAAAGCAATCCCGGGCCAATGGTGAGCAAGGGCGA

GGAGCTGTTCACCGGCGTTGTGCCAATACTGGTTGAGTTGGATGGCGATG

-continued
TCAACGGACACAAATTTAGCGTAAGCGGGGAGGGAGAGGGCGACGCCACA

TATGGCAAGCTGACCCTGAAGTTCATTTGCACGACCGGCAAATTGCCCGT

CCCTTGGCCCACACTTGTGACGACCCTGACTTATGGCGTACAGTGCTTCA

GCAGGTACCCTGATCATATGAAGCAACACGACTTCTTTAAGAGTGCCATG

CCAGAGGGATACGTCCAGGAAAGAACCATATTCTTCAAAGATGATGGAAA

TTACAAAACCCGGGCAGAGGTCAAGTTTGAAGGCGACACCCTGGTGAACA

GGATCGAACTCAAAGGCATCGATTTCAAAGAGGACGGAAACATCCTCGGA

CACAAACTGGAATACAATTACAACAGCCACAACGTCTACATCATGGCAGA

TAAACAAAAGAACGGTATTAAAGTGAACTTCAAGATCCGGCACAACATCG

AAGACGGCTCCGTCCAGCTTGCCGACCACTACCAGCAAAATACCCCGATC

GGCGACGGCCCCGTTCTCCTCCCCGATAATCACTACCTGAGTACACAGTC

AGCCTTGAGCAAAGACCCTAATGAAAAGCGGGACCACATGGTTTTGCTGG

AGTTCGTTACCGCAGCGGGTATTACGCTGGGTATGGACGAGCTTTACAAG

TAA

The coding sequence of QTA022P (plasmid containing codon optimised sequence for mBDNF-non-functional viral-2A peptide-eGFP) is referred to here as SEQ ID No: 105, as follows:

[SEQ ID No: 105]
ATGACTATCCTGTTTCTGACAATGGTTATTAGCTATTTCGGTTGCATGAA

GGCTCACAGTGATCCCGCACGCCGCGGAGAACTTAGCGTGTGCGACAGCA

TCAGCGAGTGGGTCACCGCCGCCGATAAGAAGACCGCTGTGGATATGTCC

GGCGGGACCGTCACTGTACTCGAAAAAGTTCCAGTGAGCAAAGGCCAACT

GAAACAATATTTCTATGAAACTAAGTGCAACCCCATGGGGTACACCAAGG

AGGGCTGCCGGGGAATCGACAAGAGACACTGGAATTCCCAGTGCCGGACC

ACTCAGAGCTACGTCCGCGCCTTGACGATGGATTCAAAGAAGCGCATCGG

ATGGCGGTTCATAAGAATCGACACCAGTTGTGTGTGCACGCTGACGATAA

AACGGGGCGGGCCCCTGTCAAACAAACCCTCAATTTTGACTTGCTGAAG

CTTGCTGGGGATGTCGAGTCCGCTGCCGCGGCTATGGTGAGCAAGGGCGA

GGAGCTGTTCACCGGCGTTGTGCCAATACTGGTTGAGTTGGATGGCGATG

TCAACGGACACAAATTTAGCGTAAGCGGGGAGGGAGAGGGCGACGCCACA

TATGGCAAGCTGACCCTGAAGTTCATTTGCACGACCGGCAAATTGCCCGT

CCCTTGGCCCACACTTGTGACGACCCTGACTTATGGCGTACAGTGCTTCA

GCAGGTACCCTGATCATATGAAGCAACACGACTTCTTTAAGAGTGCCATG

CCAGAGGGATACGTCCAGGAAAGAACCATATTCTTCAAAGATGATGGAAA

TTACAAAACCCGGGCAGAGGTCAAGTTTGAAGGCGACACCCTGGTGAACA

GGATCGAACTCAAAGGCATCGATTTCAAAGAGGACGGAAACATCCTCGGA

CACAAACTGGAATACAATTACAACAGCCACAACGTCTACATCATGGCAGA

TAAACAAAAGAACGGTATTAAAGTGAACTTCAAGATCCGGCACAACATCG

AAGACGGCTCCGTCCAGCTTGCCGACCACTACCAGCAAAATACCCCGATC

GGCGACGGCCCCGTTCTCCTCCCCGATAATCACTACCTGAGTACACAGTC

AGCCTTGAGCAAAGACCCTAATGAAAAGCGGGACCACATGGTTTTGCTGG

-continued
AGTTCGTTACCGCAGCGGGTATTACGCTGGGTATGGACGAGCTTTACAAG

TAA

The coding sequence of QTA023P (plasmid containing codon optimised sequence for eGFP-viral-2A peptide-mBDNF) is referred to here as SEQ ID No: 106, as follows:

[SEQ ID No: 106]
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTA

CGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAGGACCCCAACGAGAAGCGCGA

TCACATGGTCCTGCTGGAGTTCGTGACCGCCGCCGGGATCACTCTCGGCA

TGGACGAGCTGTACAAGGCTCCCGTTAAACAAACTCTGAACTTCGACCTG

CTGAAGCTGGCTGGAGACGTGGAGTCCAACCCTGGACCTATGACCATCCT

TTTCCTTACTATGGTTATTTCATACTTCGGTTGCATGAAGGCGCACTCCG

ACCCTGCCCGCCGTGGGGAGCTGAGCGTGTGTGACAGTATTAGCGAGTGG

GTCACAGCGGCAGATAAAAAGACTGCAGTGGACATGTCTGGCGGGACGGT

CACAGTCCTAGAGAAAGTCCCGGTATCCAAAGGCCAACTGAAGCAGTATT

TCTACGAGACCAAGTGTAATCCCATGGGTTACACCAAGGAAGGCTGCAGG

GGCATAGACAAAAGGCACTGGAACTCGCAATGCCGAACTACCCAATCGTA

TGTTCGGGCCCTTACTATGGATAGCAAAAAGAGAATTGGCTGGCGATTCA

TAAGGATAGACACTTCCTGTGTATGTACACTGACCATTAAAAGGGGAAGA

TAG

Referring to FIG. 14A, there is shown a Western blot of HEK293 cell homogenates 48 hours after transfection with the QTA020V vector. It shows efficient processing of the large precursor coding region which includes the TrkB receptor and BDNF separated by the viral-2A peptide sequence. The two TrkB and mBDNF-immunoreactive transgenes are within in the predicted correct molecular weight sizes. A lack of staining of large precursor protein above the TrkB receptor band should be noted, indicating almost complete or complete processing of the precursor protein in five repeats. FIGS. 14B and 14C show that the transgene proteins produced after vial-2A peptide cleavage have been transported to the correct intracellular compartments in HEK293 cells after processing (TrkB receptors to the cell surface and BDNF to storage vesicles prior to release).

FIG. 15 shows that addition of the viral-2A peptide sequence separating the two coding regions for the TrkB receptor and BDNF results in efficient processing into the two transgenes in mouse retina following intravitreal injection of the rAAV2 vector, QTA020V.

FIG. 16 shows the expression of transgenes in mouse retinal ganglion cell layer as shown by immunocytochemistry following injection of QTA020V, a rAAV2 vector containing the coding for the TrkB receptor and BDNF, separated by the viral-2A peptide sequence. Target retinal ganglion cell bodies are stained red with anti-Brn3A antibodies and cell nuclei are counter-stained blue with DAPI to distinguish the retinal layers.

Referring to FIG. 17, there is shown pre-treatment of QTA020V (containing coding for TrkB receptor and BDNF, separated by the viral-2A peptide sequence) via intravitreal injection (2 µl of $9 \times 10^{12}$ vector particles/ml) imparts significant neuroprotective efficacy on retinal ganglion cell survival following optic nerve crush in the mouse versus control animals treated with rAAV2-CAG-eGFP vector. The level of neuroprotection by the QTA020V vector was also greater than that provided by a vector expressing only BDNF. All three groups of animals were subjected to optic nerve crush procedure and the number of retinal ganglion cells measured 7 days after the insult. Retinal ganglion cells were reduced by 71% in controls (black bars) versus animals subject to sham crush (data not shown).

REFERENCES

1. Quigley H A, Number of people with glaucoma worldwide. Brit J. Ophthalmol. 1996, vol. 80, PP: 389-393.
2. www.preventblindness.org
3. Goldberg I, Relationship between intraocular pressure and preservation of visual field in glaucoma. Surv. Ophthalmol. 2003 vol. 48 Suppl. 1, PP: S3-S7.
4. Glaucoma, Merck Manual of Diagnosis and Therapy, 1999, Merck Research Laboratories; Whitehouse Station, N.J., PP: 733-738.
5. Alward W L, Medical Management of Glaucoma. New Eng. J. Med., 1998; vol. 339, PP: 1298-1307
6. Coleman A L, Glaucoma. Lancet, 1999; vol. 354, PP: 1803-1810.
7. Medeiros F A, and Weinreb R N, Medical Backgrounders: glaucoma. Drugs of Today 2002, vol. 38, PP: 563-570.
8. Bakalash S, Kipnis J, Yoles E, and Schwartz M, Resistance of retinal ganglion cells to an increase in intraocular pressure is immune-dependent. Invest. Ophthalmol. Vis. Sci., 2002, vol. 43, PP: 2648-2653.
9. Kipnis J, Yoles E, Porat Z, Cohen A, Mor F, Sela M, Cohen I R, and Schwartz M, T cell immunity to copolymer 1 confers neuroprotection on the damaged optic nerve: Possible therapy for optic neuropathies. Proc. Natl. Acad. Sci. 2000, vol. 97, PP: 7446-7451.
10. Quigley H A, Nickells R W, Kerrigan L A, Pease M E, Thibault D J, and Zack D J, Retinal ganglion cell death in experimental glaucoma and after axotomy occurs by apoptosis. Invest. Ophthalmol. Vis. Sci. 1995 vol. 36, PP: 774-786.
11. Weinreb R N, and Levin L A, Is neuroprotection a viable therapy for glaucoma? Arch. Ophthalmol. 1999, vol. 117, PP: 1540-1544.
12. Chao M V. Neurotrophins and their receptors: A convergence point for many signalling pathways. Nature Rev. Neurosci. 2003, vol. 4, PP: 299-309.
13. Dawbarn D, and Allen S J, Neurotrophins and neurodegeneration. Neuropathol. Appl. Neurobiol. 2003, vol. 29, PP: 211-230.
14. Barde Y-A, Leibrock J, Lottspeich F, Edgar D, Yancopoulos G, and Thoenen H, Brain-derived neurotrophic factor 1993, U.S. patent Ser. No. 05/229,500.
15. Mey J, and Thanos S, Intravitreal injections of neurotrophic factors support the survival of axotomized retinal ganglion cells in adult rats in vivo. Brain Res. 1993, 602: 304-317.
16. Mansour-Rabaey S, Clarke D B, Wang Y-C, Bray G M, and Aguayo A J, Effects of ocular injury and administration of brain-derived neurotrophic factor on survival and regrowth of axotomized retinal ganglion cells. Proc. Natl. Acad. Sci. USA. 1994, vol. 91, PP: 1632-1636.
17. Peinado-Ramon P, Salvador M, Viṽegas-Perez M P, and Vidal-Sanz M, Effects of axotomy and intraocular administration of NT-4, NT-3 and brain-derived neurotrophic factor on the survival of adult rat retinal ganglion cells. A quantitative in vivo study. Invest Ophthalmol. Vis. Sci. 1996, vol. 37, PP: 489-500.
18. Di Polo A, Aigner L J, Dunn R J, Bray G M, and Aguayo A J, Prolonged delivery of brain-derived neurotrophic factor by adenovirus-infected Müller cells temporarily rescues injured retinal ganglion cells. Proc. Natl. Acad. Sci. USA. 1998, vol. 95, PP: 3978-3983.
19. Klocker N, Kermer P, Weishaupt J H, Labes M, Ankerhold R, and Bahr M, Brain-derived neurotrophic factor-mediated neuroprotection of adult rat retinal ganglion cells in vivo does not exclusively depend on phosphatidyl-inositol-3'-kinase/protein kinase B signaling. J. Neurosci. 2000, vol. 20, PP: 6962-6967.
20. Ko M L, Hu D N, Ritch R, Sharma S C, and Chen C F, Patterns of retinal ganglion cell survival after brain-derived neurotrophic factor administration in hypertensive eyes of rats. Neurosci. Lett. 2001, vol. 305, PP: 139-142.
21. Chen H, and Weber A J, BDNF enhances retinal ganglion cell survival in cats with optic nerve damage. Invest Opthamol. Vis. Sci. 2001, vol. 42, PP: 966-974.
22. Pórez M T R, and Caminos E, Expression of brain-derived neurotrophic factor and its functional receptor in neonatal and adult rat retina. Neurosci. Lett. 1995, vol. 183, PP: 96-99.
23. Vecino E, Ugarte M, Nash M S, and Osborne N N. NMDA induces BDNF expression in the albino rat retina in vivo. Neuroreport. 1999 vol. 10, PP: 1103-1106.
24. Mowla S J, Farhadi H F, Pareek S, Atwal J K, Morris S J, Seidah N G, and Murphy R A. Biosynthesis and post-translational processing of the precursor to brain-derived neurotrophic factor. J. Biol. Chem. 2001 vol 276, PP: 12660-12666.
25. Gupta V K, You Y, Gupta V B, Klistorner A, and Graham S L. TrkB receptor signalling: Implications in neurodegenerative, psychiatric and proliferative disorders. Int. J. Mol. Sci. 2013, vol. 14, PP: 10122-10142
26. Teng, H. K., Teng, K. K., Lee, R., Wright, S., Tevar, S., Almeida, R. D., Kermani, P., Torkin, R., Chen, Z. Y., Lee, F. S., Kraemer, R. T., Nykjaer, A. and Hempstead, B. L. ProBDNF induces neuronal apoptosis via activation of a receptor complex of p75NTR and sortilin. J. Neurosci. 2005, vol. 25, PP: 5455-5463.
27. Wei Y, Zhang F, Zao J, Jiang X, Lu Q, Gao E and Wand N. Enhanced protein expression of proBDNF and proNGF in elevated intraocular pressure-induced rat retinal ischemia. Chin. Med. J. 2012, vol. 125, PP: 3875-3879.
28. Woo N H, Teng H K, Siao C-J, Chiaruttini C, Pang P T, Milner T A, Hempstead B L and Lu B. Activation of 29. Lebrun-Julien F, Bertrand M J, De Backer O, Stellwagen D, Morales C R, Di Polo A, and Barker P A. ProNGF induces TNFalpha-dependent death of retinal ganglion cells through a p75NTR non-cell-autonomous signaling pathway. Proc. Natl. Acad. Sci. USA. 2010 vol. 107, PP: 3817-3822.
30. Quigley H A, McKinnon S J, Zack D J, Pease M E, Kerrigan-Baumrind L A, Kerrigan D F, and Mitchell R S, Retrograde axonal transport of BDNF in retinal ganglion cells is blocked by acute IOP elevation in rats. Invest. Ophthalmol. Vis. Sci., 2000 vol. 41, PP: 3460-3466.
31. Pease M E McKinnon S J, Quigley H A, Kerrigan-Baumrind L A, and Zack D J, Obstructed axonal transport of BDNF and its receptor TRKB in experimental glaucoma. Invest. Ophthalmol. Vis. Sci. 2000, vol. 41, PP: 764-774.
32. Wei Y, Wang N, Lu Q, Zhang N, Zheng D, and Li J. Enhanced protein expressions of sortilin and p75NTR in retina of rat following elevated intraocular pressure-induced retinal ischemia. Neurosci. Lett. 2007, vol. 429, PP: 169-174.
33. Martin K R G, Quigley H A, Zack D J, Levkovitch-Verbin H, Kielczewski J, Valenta D, Baumrind L, Pease M E, Klein R L, and Hauswirth W W, Gene therapy with brain-derived neurotrophic factor as a protection: Retinal ganglion cells in a rat glaucoma model. Invest. Ophthalmol. Vis. Sci., 2003, vol. 44, PP: 4357-4365.
34. Ren R, Li Y, Liu Z, Liu K, and He S, Long-term rescue of rat retinal ganglion cells and visual function by AAV-mediated BDNF expression after acute elevation of intraocular pressure. Invest. Ophthamol. Vis. Sci., 2012, vol. 53, PP: 1003-1011.
35. Cheng L, Sapieha P, Kittlerova P, Hauswirth W W, Di Polo A, TrkB gene transfer protects retinal ganglion cells from axotomy-induced death in vivo. J. Neurosci., 2002, vol. 22, PP: 3977-3986.
36. Bai Y, Xu J, Brahimi F, Zhuo Y, Sarunic M V, and Saragovi H U, An agonistic TrkB mAb causes sustained TrkB activation, delays RGC death, and protects the retinal structure in optic nerve axotomy and in glaucoma. Invest. Ophthalmol. Vis. Sci. 2012, vol. 51, PP: 4722-4731.
37. Jelsma T N, Hyman Friedman H, Berkelaar M, Bra. G M, and Aguayo A J, Different forms of the neurotrophin receptor trkB mRNA predominate in rat retina and optic nerve. J. Neurobiol. 1993, vol. 24, PP: 1207-1214.
38. Gomes J R, Costa J T, Melo C V, Felizzi F, Monteiro P, Pinto M J, Inácio A R, Wieloch T, Almeida R D, Grãos M, and Duarte C B, Excitotoxicity down regulates TrkB.Fl signaling and up regulates the neuroprotective truncated TrkB receptors in cultured hippocampal and striatal neurons J. Neurosci. 2012, vol. 32, PP: 4610-4622.
39. Gupta V K, You Y, Klistorner A, and Graham S L. Shp-2 regulates the TrkB receptor activity in the retinal ganglion cells under glaucomatous stress. Biochimica et Biophysica Acta 2012, vol. 1822, PP: 1643-1649.
40. Khalin I, Alyautdin R, Kocherga G, Bakar M A, Targeted delivery of brain-derived neurotrophic factor for the treatment of blindness and deafness. Int. J. Nanomedicine. 2015, vol. 10, PP: 3245-3267.
41. Budenz C L, Wong H T, Swiderski D L, Shibata S B, Pfingst B E, Raphael Y, Differential effects of AAV.BDNF and AAV.Ntf3 in the deafened adult guinea pig ear. Sci. Rep. 2015, vol. 5 PP: 8619.
42. Havenith S, Versnel H, Klis S F, Grolman W, Local delivery of brain-derived neurotrophic factor on the perforated round window membrane in Guinea pigs: a possible clinical application. Otol Neurotol. 2015, vol. 36, PP: 705-711
43. Jian-Yi Zhang J-Y, Luo X-G, Xian C J, Liu Z-H, Zhou X-F (2008) Endogenous BDNF is required for myelination and regeneration of injured sciatic nerve in rodents. Eur. J. Neurosci. Vol. 12, PP: 4171-4180.
44. Lindsey R M (1988) Nerve growth factors (NGF, BDNF) enhance axonal regeneration but are not required for survival of adult sensory neurons. J. Neurosci. vol. 8, PP: 2394-2405.
45. Martinez-Salas E. Internal ribosome entry site biology and its use in expression vectors. Curr. Opin. Biotechnol. 1999, vol. 10, PP: 458-464.
46. Harries M et al. Comparison of bicistronic retroviral vectors containing internal ribosome entry sites (IRES) using expression of human interleukin-12 (IL-12) as a readout. J. Gene Med. 200 vol. 2, PP: 243-249.
47. Furler S, Paterna J-C, Weibel M and Bueler H Recombinant AAV vectors containing the foot and mouth disease virus 2A sequence confer efficient bicistronic gene expression in cultured cells and rat substantia nigra neurons Gene Ther. 2001, vol. 8, PP: 864-873.

SEQUENCE LISTING

<160> NUMBER OF SEQ ID NOS: 108

<210> SEQ ID NO 1
<211> LENGTH: 469
<212> TYPE: DNA
<213> ORGANISM: Homo sapiens
<220> FEATURE:
<221> NAME/KEY: Promoter
<222> LOCATION: (1)..(469)
<223> OTHER INFORMATION: Human synapsin I (SYN I) promoter

<400> SEQUENCE: 1

```
ctgcagaggg ccctgcgtat gagtgcaagt gggttttagg accaggatga ggcggggtgg      60
gggtgcctac ctgacgaccg accccgaccc actggacaag cacccaaccc ccattcccca     120
aattgcgcat cccctatcag agaggggag gggaaacagg atgcggcgag gcgcgtgcgc     180
actgccagct tcagcaccgc ggacagtgcc ttcgccccg cctggcggcg cgcgccaccg     240
```

```
ccgcctcagc actgaaggcg cgctgacgtc actcgccggt cccccgcaaa ctcccttcc    300 cggccacctt ggtcgcgtcc gcgccgccgc cggcccagcc ggaccgcacc acgcgaggcg    360
cgagataggg gggcacgggc gcgaccatct gcgctgcggc gccggcgact cagcgctgcc    420
tcagtctgcg gtgggcagcg gaggagtcgt gtcgtgcctg agagcgcag                469
```

<210> SEQ ID NO 2
<211> LENGTH: 1733
<212> TYPE: DNA
<213> ORGANISM: Artificial Sequence
<220> FEATURE:
<223> OTHER INFORMATION: synthetic sequence
<220> FEATURE:
<221> NAME/KEY: Promoter
<222> LOCATION: (1)..(1733)
<223> OTHER INFORMATION: It is the CAG promoter which comprises the
      following: (C) the cytomegalovirus (CMV) early enhancer element,
      (A) the promoter, the first exon and the first intron of chicken
      beta-actin gene.

<400> SEQUENCE: 2

```
ctcgacattg attattgact agttattaat agtaatcaat tacggggtca ttagttcata    60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtcgagg tgagccccac gttctgcttc actctcccca    420 tctcccccc ctccccaccc caatttttgt atttatttat ttttaatta ttttgtgcag    480 cgatggggc ggggggggg gggggcgcg cgccaggcgg ggcggggcgg ggcgaggggc    540 ggggcgggc gaggcggaga ggtgcggcgg cagccaatca gagcggcgcg ctccgaaagt    600 ttcctttat ggcgaggcgg cggcggcggc ggccctataa aaagcgaagc gcgcggcggg    660
cgggagtcgc tgcgcgctgc cttcgccccg tgccccgctc cgccgccgcc tcgcgccgcc    720
cgccccggct ctgactgacc gcgttactcc cacaggtgag cgggcgggac ggcccttctc    780
ctccgggctg taattagcgc ttggtttaat gacggcttgt ttcttttctg tggctgcgtg    840
aaagccttga ggggctccgg gagggccctt tgtgcggggg gagcggctcg ggggtgcgt    900 gcgtgtgtgt gtgcgtgggg agcgccgcgt gcggctccgc gctgcccggc ggctgtgagc    960
gctgcgggcg cggcgcgggg ctttgtgcgc tccgcagtgt gcgcgagggg agcgcggccg    1020
ggggcggtgc cccgcggtgc gggggggggct gcgaggggaa caaaggctgc gtgcggggtg    1080
tgtgcgtggg ggggtgagca ggggggtgtgg gcgcgtcggt cgggctgcaa cccccctgc    1140 accccctcc ccgagttgct gagcacggcc cggcttcggg tgcggggctc cgtacggggc    1200
gtggcgcggg gctcgccgtg ccgggcgggg ggtggcggca ggtggggtg ccgggcgggg    1260 cggggccgcc tcgggccggg gagggctcgg gggaggggcg cggcggcccc cggagcgccg    1320
gcggctgtcg aggcgcggcg agccgcagcc attgcctttt atggtaatcg tgcgagaggg    1380
cgcagggact ccctttgtcc caaatctgtg cggagccgaa atctgggagg cgccgccgca    1440 cccctctag cggcgcgggg gcgaagcggt gcggcgccgg caggaaggaa atgggcgggg    1500
agggccttcg tgcgtcgccg cgccgccgtc cccttctccc tctccagcct cggggctgtc    1560
cgcgggggga cggctgcctt cggggggggac ggggcagggc ggggttcggc ttctggcgtg    1620
```

```
tgaccggcgg ctctagagcc tctgctaacc atgttcatgc cttcttcttt ttcctacagc    1680
tcctgggcaa cgtgctggtt attgtgctgt ctcatcattt tggcaaagaa ttg           1733
```

```
<210> SEQ ID NO 3
<211> LENGTH: 664
<212> TYPE: DNA
<213> ORGANISM: Artificial Sequence
<220> FEATURE:
<223> OTHER INFORMATION: synthetic sequence
<220> FEATURE:
<221> NAME/KEY: Promoter
<222> LOCATION: (1)..(664)
<223> OTHER INFORMATION: Truncated CAG nucleotide promoter sequence.

<400> SEQUENCE: 3
ctagatctga attcggtacc ctagttatta atagtaatca attacggggt cattagttca     60
tagcccatat atggagttcc gcgttacata acttacggta atggcccgc ctggctgacc    120 gcccaacgac ccccgcccat tgacgtcaat aatgacgtat gttcccatag taacgccaat   180
agggactttc cattgacgtc aatgggtgga ctatttacgg taaactgccc acttggcagt    240
acatcaagtg tatcatatgc caagtacgcc ccctattgac gtcaatgacg gtaaatggcc    300
cgcctggcat tatgcccagt acatgacctt atgggacttt cctacttggc agtacatcta    360
cgtattagtc atcgctatta ccatggtcga ggtgagcccc acgttctgct tcactctccc    420
catctccccc ccctccccac ccccaatttt gtatttattt attttttaat tattttgtgc   480
agcgatgggg gcggggggggg ggggggggcg cgcgccaggc ggggcggggc ggggcgaggg    540
gcggggcggg gcgaggcgga gaggtgcggc ggcagccaat cagagcggcg cgctccgaaa    600
gtttcctttt atggcgaggc ggcggcggcg gcggccctat aaaaagcgaa gcgcgcggcg    660
ggcg                                                                  664

<210> SEQ ID NO 4
<211> LENGTH: 11
<212> TYPE: PRT
<213> ORGANISM: Artificial Sequence
<220> FEATURE:
<223> OTHER INFORMATION: Peptide sequence of spacer C-terminue

<400> SEQUENCE: 4

Gln Ala Gly Asp Val Glu Glu Asn Pro Gly Pro
1               5                   10

<210> SEQ ID NO 5
<211> LENGTH: 63
<212> TYPE: DNA
<213> ORGANISM: Artificial Sequence
<220> FEATURE:
<223> OTHER INFORMATION: First embodiment of a spacer nucleotide
      sequence

<400> SEQUENCE: 5
ggaagcggag ctactaactt cagcctgctg aaggctggag acgtggagga gaaccctgga     60
cct                                                                   63

<210> SEQ ID NO 6
<211> LENGTH: 21
<212> TYPE: PRT
<213> ORGANISM: Artificial Sequence
<220> FEATURE:
<223> OTHER INFORMATION: First embodiment of a spacer peptide sequence
```

<400> SEQUENCE: 6

Gly Ser Gly Ala Thr Asn Phe Ser Leu Leu Gln Ala Gly Asp Val Glu
1               5                   10                  15

Glu Asn Pro Gly Pro
            20

<210> SEQ ID NO 7
<211> LENGTH: 63
<212> TYPE: DNA
<213> ORGANISM: Artificial Sequence
<220> FEATURE:
<223> OTHER INFORMATION: Second embodiment of the spacer nucleotide
      sequence

<400> SEQUENCE: 7
agcggagcta ctaacttcag cctgctgaag caggctggag acgtggagga gaaccctgga    60
cct                                                                 63

<210> SEQ ID NO 8
<211> LENGTH: 21
<212> TYPE: PRT
<213> ORGANISM: Artificial Sequence
<220> FEATURE:
<223> OTHER INFORMATION: Second embodiment of the spacer peptide
      sequence

<400> SEQUENCE: 8

Ser Gly Ala Thr Asn Phe Ser Leu Leu Lys Gln Ala Gly Asp Val Glu
1               5                   10                  15

Glu Asn Pro Gly Pro
            20

<210> SEQ ID NO 9
<211> LENGTH: 822
<212> TYPE: PRT
<213> ORGANISM: Homo sapiens

<400> SEQUENCE: 9

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
                20                  25                  30

Pro Thr Ser Cys Lys Cys Ser Ala Ser Arg Ile Trp Cys Ser Asp Pro
            35                  40                  45

Ser Pro Gly Ile Val Ala Phe Pro Arg Leu Glu Pro Asn Ser Val Asp
        50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys

```
            165                 170                 175
Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
            195                 200                 205

Glu Glu Gly Lys Ser Ile Thr Leu Ser Cys Ser Val Ala Gly Asp Pro
210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
            275                 280                 285

Ile Thr Phe Leu Glu Ser Pro Thr Ser Asp His His Trp Cys Ile Pro
        290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
                355                 360                 365

Lys Asp Glu Lys Gln Ile Ser Ala His Phe Met Gly Trp Pro Gly Ile
        370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
        435                 440                 445

Val Met Leu Phe Leu Leu Lys Leu Ala Arg His Ser Lys Phe Gly Met
450                 455                 460

Lys Gly Pro Ala Ser Val Ile Ser Asn Asp Asp Ser Ala Ser Pro
465                 470                 475                 480

Leu His His Ile Ser Asn Gly Ser Asn Thr Pro Ser Ser Glu Gly
                485                 490                 495

Gly Pro Asp Ala Val Ile Ile Gly Met Thr Lys Ile Pro Val Ile Glu
            500                 505                 510

Asn Pro Gln Tyr Phe Gly Ile Thr Asn Ser Gln Leu Lys Pro Asp Thr
            515                 520                 525

Phe Val Gln His Ile Lys Arg His Asn Ile Val Leu Lys Arg Glu Leu
        530                 535                 540

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
                565                 570                 575

Ala Ser Asp Asn Ala Arg Lys Asp Phe His Arg Glu Ala Glu Leu Leu
            580                 585                 590
```

```
Thr Asn Leu Gln His Glu His Ile Val Lys Phe Tyr Gly Val Cys Val
        595                 600                 605

Glu Gly Asp Pro Leu Ile Met Val Phe Glu Tyr Met Lys His Gly Asp
610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
                645                 650                 655

Ala Gln Gln Ile Ala Ala Gly Met Val Tyr Leu Ala Ser Gln His Phe
            660                 665                 670

Val His Arg Asp Leu Ala Thr Arg Asn Cys Leu Val Gly Glu Asn Leu
        675                 680                 685

Leu Val Lys Ile Gly Asp Phe Gly Met Ser Arg Asp Val Tyr Ser Thr
    690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
            740                 745                 750

Pro Trp Tyr Gln Leu Ser Asn Asn Glu Val Ile Glu Cys Ile Thr Gln
        755                 760                 765

Gly Arg Val Leu Gln Arg Pro Arg Thr Cys Pro Gln Glu Val Tyr Glu
    770                 775                 780

Leu Met Leu Gly Cys Trp Gln Arg Glu Pro His Met Arg Lys Asn Ile
785                 790                 795                 800

Lys Gly Ile His Thr Leu Leu Gln Asn Leu Ala Lys Ala Ser Pro Val
                805                 810                 815

Tyr Leu Asp Ile Leu Gly
            820

<210> SEQ ID NO 10
<211> LENGTH: 2466
<212> TYPE: DNA
<213> ORGANISM: Homo sapiens

<400> SEQUENCE: 10
atgtcgtcct ggataaggtg gcatggaccc gccatggcgc ggctctgggg cttctgctgg      60
ctggttgtgg gcttctggag gccgctttc gcctgtccca cgtcctgcaa atgcagtgcc     120
tctcggatct ggtgcagcga cccttctcct ggcatcgtgg catttccgag attggagcct     180
aacagtgtag atcctgagaa catcaccgaa attttcatcg caaaccagaa aggttagaa     240 atcatcaacg aagatgatgt tgaagcttat gtgggactga gaaatctgac aattgtggat     300
tctggattaa aatttgtggc tcataaagca tttctgaaaa acagcaacct gcagcacatc     360
aattttaccc gaaacaaact gacgagtttg tctaggaaac atttccgtca ccttgacttg     420
tctgaactga tcctggtggg caatccattt acatgctcct gtgacattat gtggatcaag     480
actctccaag aggctaaatc cagtccagac actcaggatt gtactgcct gaatgaaagc     540 agcaagaata ttcccctggc aaacctgcag atacccaatt gtggtttgcc atctgcaaat     600
ctggccgcac ctaacctcac tgtggaggaa ggaaagtcta tcacattatc ctgtagtgtg     660
gcaggtgatc cggttcctaa tatgtattgg gatgttggta acctgggttc caaacatatg     720
aatgaaacaa gccacacaca gggctcctta aggataacta catttcatc cgatgacagt     780
```

-continued

```
gggaagcaga tctcttgtgt ggcggaaaat cttgtaggag aagatcaaga ttctgtcaac    840
ctcactgtgc attttgcacc aactatcaca tttctcgaat ctccaacctc agaccaccac    900
tggtgcattc cattcactgt gaaaggcaac cccaaaccag cgcttcagtg gttctataac    960
ggggcaatat tgaatgagtc caaatacatc tgtactaaaa tacatgttac caatcacacg   1020
gagtaccacg gctgcctcca gctggataat cccactcaca tgaacaatgg ggactacact   1080
ctaatagcca agaatgagta tgggaaggat gagaaacaga tttctgctca cttcatgggc   1140
tggcctggaa ttgacgatgg tgcaaaccca aattatcctg atgtaattta tgaagattat   1200
ggaactgcag cgaatgacat cggggacacc acgaacagaa gtaatgaaat cccttccaca   1260
gacgtcactg ataaaaccgg tcgggaacat ctctcggtct atgctgtggt ggtgattgcg   1320
tctgtggtgg attttgcct tttggtaatg ctgtttctgc ttaagttggc aagcactcc    1380
aagtttggca tgaaaggccc agcctccgtt atcagcaatg atgatgactc tgccagccca   1440
ctccatcaca tctccaatgg gagtaacact ccatcttctt cggaaggtgg cccagatgct   1500
gtcattattg gaatgaccaa gatccctgtc attgaaaatc cccagtactt tggcatcacc   1560
aacagtcagc tcaagccaga cacatttgtt cagcacatca agcgacataa cattgttctg   1620
aaaagggagc taggcgaagg agccttggga aaagtgttcc tagctgaatg ctataacctc   1680
tgtcctgagc aggacaagat cttggtggca gtgaagaccc tgaaggatgc cagtgacaat   1740
gcacgcaagg acttccaccg tgaggccgag ctcctgacca acctccagca tgagcacatc   1800
gtcaagttct atggcgtctg cgtggagggc gacccctca tcatggtctt tgagtacatg   1860
aagcatgggg acctcaacaa gttcctcagg gcacacggcc ctgatgccgt gctgatggct   1920
gagggcaacc cgcccacgga actgacgcag tcgcagatgc tgcatatagc ccagcagatc   1980
gccgcgggca tggtctacct ggcgtcccag cacttcgtgc accgcgattt ggccaccagg   2040
aactgcctgg tcggggagaa cttgctggtg aaaatcgggg actttgggat gtcccgggac   2100
gtgtacagca ctgactacta cagggtcggt ggccacacaa tgctgcccat cgctggatg    2160
cctccagaga gcatcatgta caggaaattc acgacgaaaa gcgacgtctg gagcctgggg   2220
gtcgtgttgt gggagatttt cacctatggc aaacagccct ggtaccagct gtcaaacaat   2280
gaggtgatag agtgtatcac tcagggccga gtcctgcagc gaccccgcac gtgccccag    2340
gaggtgtatg agctgatgct ggggtgctgg cagcgagagc ccacatgag gaagaacatc    2400
aagggcatcc ataccctcct tcagaacttg gccaaggcat ctccggtcta cctggacatt   2460
ctaggc                                                              2466
```

<210> SEQ ID NO 11
<211> LENGTH: 838
<212> TYPE: PRT
<213> ORGANISM: Homo sapiens

<400> SEQUENCE: 11

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

```
Pro Glu Asn Ile Thr Glu Ile Phe Ile Ala Asn Gln Lys Arg Leu Glu
 65                  70                  75                  80

Ile Ile Asn Glu Asp Asp Val Glu Ala Tyr Val Gly Leu Arg Asn Leu
                 85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
        435                 440                 445

Val Met Leu Phe Leu Leu Lys Leu Ala Arg His Ser Lys Phe Gly Met
450                 455                 460

Lys Asp Phe Ser Trp Phe Gly Phe Gly Lys Val Lys Ser Arg Gln Gly
465                 470                 475                 480

Val Gly Pro Ala Ser Val Ile Ser Asn Asp Asp Asp Ser Ala Ser Pro
```

```
                         485                 490                 495
Leu His His Ile Ser Asn Gly Ser Asn Thr Pro Ser Ser Ser Glu Gly
                 500                 505                 510

Gly Pro Asp Ala Val Ile Ile Gly Met Thr Lys Ile Pro Val Ile Glu
         515                 520                 525

Asn Pro Gln Tyr Phe Gly Ile Thr Asn Ser Gln Leu Lys Pro Asp Thr
     530                 535                 540

Phe Val Gln His Ile Lys Arg His Asn Ile Val Leu Lys Arg Glu Leu
545                 550                 555                 560

Gly Glu Gly Ala Phe Gly Lys Val Phe Leu Ala Glu Cys Tyr Asn Leu
                 565                 570                 575

Cys Pro Glu Gln Asp Lys Ile Leu Val Ala Val Lys Thr Leu Lys Asp
                 580                 585                 590

Ala Ser Asp Asn Ala Arg Lys Asp Phe His Arg Glu Ala Glu Leu Leu
             595                 600                 605

Thr Asn Leu Gln His Glu His Ile Val Lys Phe Tyr Gly Val Cys Val
610                 615                 620

Glu Gly Asp Pro Leu Ile Met Val Phe Glu Tyr Met Lys His Gly Asp
625                 630                 635                 640

Leu Asn Lys Phe Leu Arg Ala His Gly Pro Asp Ala Val Leu Met Ala
                 645                 650                 655

Glu Gly Asn Pro Pro Thr Glu Leu Thr Gln Ser Gln Met Leu His Ile
             660                 665                 670

Ala Gln Gln Ile Ala Ala Gly Met Val Tyr Leu Ala Ser Gln His Phe
             675                 680                 685

Val His Arg Asp Leu Ala Thr Arg Asn Cys Leu Val Gly Glu Asn Leu
690                 695                 700

Leu Val Lys Ile Gly Asp Phe Gly Met Ser Arg Asp Val Tyr Ser Thr
705                 710                 715                 720

Asp Tyr Tyr Arg Val Gly Gly His Thr Met Leu Pro Ile Arg Trp Met
                 725                 730                 735

Pro Pro Glu Ser Ile Met Tyr Arg Lys Phe Thr Thr Glu Ser Asp Val
             740                 745                 750

Trp Ser Leu Gly Val Val Leu Trp Glu Ile Phe Thr Tyr Gly Lys Gln
         755                 760                 765

Pro Trp Tyr Gln Leu Ser Asn Asn Glu Val Ile Glu Cys Ile Thr Gln
     770                 775                 780

Gly Arg Val Leu Gln Arg Pro Arg Thr Cys Pro Gln Glu Val Tyr Glu
785                 790                 795                 800

Leu Met Leu Gly Cys Trp Gln Arg Glu Pro His Met Arg Lys Asn Ile
                 805                 810                 815

Lys Gly Ile His Thr Leu Leu Gln Asn Leu Ala Lys Ala Ser Pro Val
             820                 825                 830

Tyr Leu Asp Ile Leu Gly
             835

<210> SEQ ID NO 12
<211> LENGTH: 2514
<212> TYPE: DNA
<213> ORGANISM: Homo sapiens

<400> SEQUENCE: 12
atgtcgtcct ggataaggtg gcatggaccc gccatggcgc ggctctgggg cttctgctgg      60
ctggttgtgg gcttctggag gccgcttttc gcctgtccca cgtcctgcaa atgcagtgcc     120
```

```
tctcggatct ggtgcagcga cccttctcct ggcatcgtgg catttccgag attggagcct      180
aacagtgtag atcctgagaa catcaccgaa attttcatcg caaaccagaa aaggttagaa      240
atcatcaacg aagatgatgt tgaagcttat gtgggactga aaatctgac aattgtggat       300 tctggattaa aatttgtggc tcataaagca tttctgaaaa acagcaacct gcagcacatc      360
aattttaccc gaaacaaact gacgagtttg tctaggaaac atttccgtca ccttgacttg      420
tctgaactga tcctggtggg caatccattt acatgctcct gtgacattat gtggatcaag      480
actctccaag aggctaaatc cagtccagac actcaggatt tgtactgcct gaatgaaagc      540
agcaagaata ttcccctggc aaacctgcag atacccaatt gtggtttgcc atctgcaaat      600
ctggccgcac ctaacctcac tgtggaggaa ggaaagtcta tcacattatc ctgtagtgtg      660
gcaggtgatc cggttcctaa tatgtattgg gatgttggta acctggtttc caaacatatg      720
aatgaaacaa gccacacaca gggctcctta aggataacta acatttcatc cgatgacagt      780
gggaagcaga tctcttgtgt ggcggaaaat cttgtaggag aagatcaaga ttctgtcaac      840
ctcactgtgc attttgcacc aactatcaca tttctcgaat ctccaacctc agaccaccac      900
tggtgcattc cattcactgt gaaaggcaac cccaaaccag cgcttcagtg gttctataac      960
ggggcaatat tgaatgagtc caaatacatc tgtactaaaa tacatgttac caatcacacg      1020
gagtaccacg gctgcctcca gctggataat cccactcaca tgaacaatgg ggactacact      1080
ctaatagcca agaatgagta tgggaaggat gagaaacaga tttctgctca cttcatgggc      1140
tggcctggaa ttgacgatgg tgcaaaccca aattatcctg atgtaattta tgaagattat      1200
ggaactgcag cgaatgacat cggggacacc acgaacagaa gtaatgaaat cccttccaca      1260
gacgtcactg ataaaaccgg tcgggaacat ctctcggtct atgctgtggt ggtgattgcg      1320
tctgtggtgg gattttgcct tttggtaatg ctgtttctgc ttaagttggc aagacactcc      1380
aagtttggca tgaaagattt ctcatggttt ggatttggga agtaaaaatc aagacaaggt      1440
gttggcccag cctccgttat cagcaatgat gatgactctg ccagcccact ccatcacatc      1500
tccaatggga gtaacactcc atcttcttcg gaaggtggcc cagatgctgt cattattgga      1560
atgaccaaga tccctgtcat tgaaaatccc cagtactttg gcatcaccaa cagtcagctc      1620
aagccagaca catttgttca gcacatcaag cgacataaca ttgttctgaa aagggagcta      1680
ggcgaaggag cctttggaaa agtgttccta gctgaatgct ataacctctg tcctgagcag      1740
gacaagatct tggtggcagt gaagacccta aaggatgcca gtgacaatgc acgcaaggac      1800
ttccaccgtg aggccgagct cctgaccaac ctccagcatg agcacatcgt caagttctat      1860
ggcgtctgcg tggagggcga cccctcatc atggtctttg agtacatgaa gcatggggac      1920
ctcaacaagt tcctcaggc acacggccct gatgccgtgc tgatggctga gggcaacccg      1980
cccacggaac tgacgcagtc gcagatgctg catatagccc agcagatcgc cgcgggcatg      2040
gtctacctgg cgtcccagca cttcgtgcac cgcgatttgg ccaccaggaa ctgcctggtc      2100
ggggagaact tgctggtgaa aatcggggac tttgggatgt cccgggacgt gtacagcact      2160
gactactaca gggtcggtgg ccacacaatg ctgcccattc gctggatgcc tccagagagc      2220
atcatgtaca ggaaattcac gacggaaagc gacgtctgga gcctgggggt cgtgttgtgg      2280
gagattttca cctatggcaa acagccctgg taccagctgt caaacaatga ggtgatagag      2340
tgtatcactc agggccgagt cctgcagcga ccccgcacgt gccccagga ggtgtatgag      2400 ctgatgctgg ggtgctggca gcgagagccc cacatgagga gaacatcaa gggcatccat      2460
```

```
acccrccttc agaacttggc caaggcatct ccggtctacc tggacattct aggc        2514
```

<210> SEQ ID NO 13
<211> LENGTH: 822
<212> TYPE: PRT
<213> ORGANISM: Homo sapiens

<400> SEQUENCE: 13

| | | | | | | | | | | | | | | | |
|---|---|---|---|---|---|---|---|---|---|---|---|---|---|---|---|
| Met | Ser | Ser | Trp | Ile | Arg | Trp | His | Gly | Pro | Ala | Met | Ala | Arg | Leu | Trp |
| 1 | | | | 5 | | | | | 10 | | | | | 15 | |
| Gly | Phe | Cys | Trp | Leu | Val | Val | Gly | Phe | Trp | Arg | Ala | Ala | Phe | Ala | Cys |
| | | | 20 | | | | | 25 | | | | | 30 | | |
| Pro | Thr | Ser | Cys | Lys | Cys | Ser | Ala | Ser | Arg | Ile | Trp | Cys | Ser | Asp | Pro |
| | | 35 | | | | | 40 | | | | | 45 | | | |
| Ser | Pro | Gly | Ile | Val | Ala | Phe | Pro | Arg | Leu | Glu | Pro | Asn | Ser | Val | Asp |
| | 50 | | | | | 55 | | | | | 60 | | | | |
| Pro | Glu | Asn | Ile | Thr | Glu | Ile | Phe | Ile | Ala | Asn | Gln | Lys | Arg | Leu | Glu |
| 65 | | | | | 70 | | | | | 75 | | | | | 80 |
| Ile | Ile | Asn | Glu | Asp | Asp | Val | Glu | Ala | Tyr | Val | Gly | Leu | Arg | Asn | Leu |
| | | | | 85 | | | | | 90 | | | | | 95 | |
| Thr | Ile | Val | Asp | Ser | Gly | Leu | Lys | Phe | Val | Ala | His | Lys | Ala | Phe | Leu |
| | | | 100 | | | | | 105 | | | | | 110 | | |
| Lys | Asn | Ser | Asn | Leu | Gln | His | Ile | Asn | Phe | Thr | Arg | Asn | Lys | Leu | Thr |
| | | 115 | | | | | 120 | | | | | 125 | | | |
| Ser | Leu | Ser | Arg | Lys | His | Phe | Arg | His | Leu | Asp | Leu | Ser | Glu | Leu | Ile |
| | 130 | | | | | 135 | | | | | 140 | | | | |
| Leu | Val | Gly | Asn | Pro | Phe | Thr | Cys | Ser | Cys | Asp | Ile | Met | Trp | Ile | Lys |
| 145 | | | | | 150 | | | | | 155 | | | | | 160 |
| Thr | Leu | Gln | Glu | Ala | Lys | Ser | Ser | Pro | Asp | Thr | Gln | Asp | Leu | Tyr | Cys |
| | | | | 165 | | | | | 170 | | | | | 175 | |
| Leu | Asn | Glu | Ser | Ser | Lys | Asn | Ile | Pro | Leu | Ala | Asn | Leu | Gln | Ile | Pro |
| | | | 180 | | | | | 185 | | | | | 190 | | |
| Asn | Cys | Gly | Leu | Pro | Ser | Ala | Asn | Leu | Ala | Ala | Pro | Asn | Leu | Thr | Val |
| | | 195 | | | | | 200 | | | | | 205 | | | |
| Glu | Glu | Gly | Lys | Ser | Ile | Thr | Leu | Ser | Cys | Ser | Val | Ala | Gly | Asp | Pro |
| | 210 | | | | | 215 | | | | | 220 | | | | |
| Val | Pro | Asn | Met | Tyr | Trp | Asp | Val | Gly | Asn | Leu | Val | Ser | Lys | His | Met |
| 225 | | | | | 230 | | | | | 235 | | | | | 240 |
| Asn | Glu | Thr | Ser | His | Thr | Gln | Gly | Ser | Leu | Arg | Ile | Thr | Asn | Ile | Ser |
| | | | | 245 | | | | | 250 | | | | | 255 | |
| Ser | Asp | Asp | Ser | Gly | Lys | Gln | Ile | Ser | Cys | Val | Ala | Glu | Asn | Leu | Val |
| | | | 260 | | | | | 265 | | | | | 270 | | |
| Gly | Glu | Asp | Gln | Asp | Ser | Val | Asn | Leu | Thr | Val | His | Phe | Ala | Pro | Thr |
| | | 275 | | | | | 280 | | | | | 285 | | | |
| Ile | Thr | Phe | Leu | Glu | Ser | Pro | Thr | Ser | Asp | His | His | Trp | Cys | Ile | Pro |
| | 290 | | | | | 295 | | | | | 300 | | | | |
| Phe | Thr | Val | Lys | Gly | Asn | Pro | Lys | Pro | Ala | Leu | Gln | Trp | Phe | Tyr | Asn |
| 305 | | | | | 310 | | | | | 315 | | | | | 320 |
| Gly | Ala | Ile | Leu | Asn | Glu | Ser | Lys | Tyr | Ile | Cys | Thr | Lys | Ile | His | Val |
| | | | | 325 | | | | | 330 | | | | | 335 | |
| Thr | Asn | His | Thr | Glu | Tyr | His | Gly | Cys | Leu | Gln | Leu | Asp | Asn | Pro | Thr |
| | | | 340 | | | | | 345 | | | | | 350 | | |
| His | Met | Asn | Asn | Gly | Asp | Tyr | Thr | Leu | Ile | Ala | Lys | Asn | Glu | Tyr | Gly |
| | | 355 | | | | | 360 | | | | | 365 | | | |

```
Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Ile Ala Ser Val Val Gly Phe Cys Leu Leu
            435                 440                 445

Val Met Leu Phe Leu Leu Lys Leu Ala Arg His Ser Lys Phe Gly Met
    450                 455                 460

Lys Gly Pro Ala Ser Val Ile Ser Asn Asp Asp Ser Ala Ser Pro
465                 470                 475                 480

Leu His His Ile Ser Asn Gly Ser Asn Thr Pro Ser Ser Glu Gly
                485                 490                 495

Gly Pro Asp Ala Val Ile Ile Gly Met Thr Lys Ile Pro Val Ile Glu
            500                 505                 510

Asn Pro Gln Glu Phe Gly Ile Thr Asn Ser Gln Leu Lys Pro Asp Thr
    515                 520                 525

Phe Val Gln His Ile Lys Arg His Asn Ile Val Leu Lys Arg Glu Leu
530                 535                 540

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
                565                 570                 575

Ala Ser Asp Asn Ala Arg Lys Asp Phe His Arg Glu Ala Glu Leu Leu
            580                 585                 590

Thr Asn Leu Gln His Glu His Ile Val Lys Phe Tyr Gly Val Cys Val
    595                 600                 605

Glu Gly Asp Pro Leu Ile Met Val Phe Glu Tyr Met Lys His Gly Asp
610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
                645                 650                 655

Ala Gln Gln Ile Ala Ala Gly Met Val Tyr Leu Ala Ser Gln His Phe
            660                 665                 670

Val His Arg Asp Leu Ala Thr Arg Asn Cys Leu Val Gly Glu Asn Leu
    675                 680                 685

Leu Val Lys Ile Gly Asp Phe Gly Met Ser Arg Asp Val Glu Ser Thr
690                 695                 700

Asp Glu Glu Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
            740                 745                 750

Pro Trp Tyr Gln Leu Ser Asn Asn Glu Val Ile Glu Cys Ile Thr Gln
    755                 760                 765

Gly Arg Val Leu Gln Arg Pro Arg Thr Cys Pro Gln Glu Val Tyr Glu
770                 775                 780

Leu Met Leu Gly Cys Trp Gln Arg Glu Pro His Met Arg Lys Asn Ile
```

```
                785                 790                 795                 800
Lys Gly Ile His Thr Leu Leu Gln Asn Leu Ala Lys Ala Ser Pro Val
                    805                 810                 815
Glu Leu Asp Ile Leu Gly
                820

<210> SEQ ID NO 14
<211> LENGTH: 2466
<212> TYPE: DNA
<213> ORGANISM: Homo sapiens

<400> SEQUENCE: 14
atgtcgtcct ggataaggtg gcatggaccc gccatggcgc ggctctgggg cttctgctgg      60
ctggttgtgg gcttctggag ggccgctttc gcctgtccca cgtcctgcaa atgcagtgcc     120
tctcggatct ggtgcagcga cccttctcct ggcatcgtgg catttccgag attggagcct     180
aacagtgtag atcctgagaa catcaccgaa attttcatcg caaaccagaa aaggttagaa     240
atcatcaacg aagatgatgt tgaagctat gtgggactga aaatctgac aattgtggat      300 tctggattaa aatttgtggc tcataaagca tttctgaaaa acagcaacct gcagcacatc     360
aattttaccc gaaacaaact gacgagtttg tctaggaaac atttccgtca ccttgacttg     420
tctgaactga tcctggtggg caatccattt acatgctcct gtgacattat gtggatcaag     480
actctccaag aggctaaatc cagtccagac actcaggatt gtactgcct gaatgaaagc      540 agcaagaata ttcccctggc aaacctgcag atacccaatt gtggtttgcc atctgcaaat     600
ctggccgcac ctaacctcac tgtggaggaa ggaaagtcta tcacattatc ctgtagtgtg     660
gcaggtgatc cggttcctaa tatgtattgg gatgttggta acctggtttc caacatatg      720 aatgaaacaa gccacacaca gggctcctta aggataacta acatttcatc cgatgacagt     780
gggaagcaga tctcttgtgt ggcggaaaat cttgtaggag aagatcaaga ttctgtcaac     840
ctcactgtgc attttgcacc aactatcaca tttctcgaat ctccaacctc agaccaccac     900
tggtgcattc cattcactgt gaaaggcaac ccaaaccag cgcttcagtg gttctataac      960
ggggcaatat tgaatgagtc caaatacatc tgtactaaaa tacatgttac caatcacacg    1020
gagtaccacg gctgcctcca gctggataat cccactcaca tgaacaatgg ggactacact    1080
ctaatagcca agaatgagta tgggaaggat gagaaacaga tttctgctca cttcatgggc    1140
tggcctggaa ttgacgatgg tgcaaaccca aattatcctg atgtaattta tgaagattat    1200
ggaactgcag cgaatgacat cggggacacc acgaacagaa gtaatgaaat ccctttccaca    1260 gacgtcactg ataaaaccgg tcgggaacat ctctcggtct atgctgtggt ggtgattgcg    1320
tctgtggtgg gattttgcct tttggtaatg ctgtttctgc ttaagttggc aagcactcc     1380 aagtttggca tgaaaggccc agcctccgtt atcagcaatg atgatgactc tgccagccca    1440
ctccatcaca tctccaatgg gagtaacact ccatcttctt cggaaggtgg cccagatgct    1500
gtcattattg gaatgaccaa gatccctgtc attgaaaatc cccaggaatt tggcatcacc    1560
aacagtcagc tcaagccaga cacatttgtt cagcacatca gcgacataa cattgttctg    1620 aaaagggagc taggcgaagg agcctttgga aaagtgttcc tagctgaatg ctataacctc    1680
tgtcctgagc aggacaagat cttggtggca gtgaagaccc tgaaggatgc cagtgacaat    1740
gcacgcaagg acttccaccg tgaggccgag ctcctgacca acctccagca tgagcacatc    1800
gtcaagttct atgcgtctg cgtggagggc gaccccctca tcatggtctt tgagtacatg    1860
aagcatgggg acctcaacaa gttcctcagg gcacacggcc ctgatgccgt gctgatggct    1920
```

```
gagggcaacc cgcccacgga actgacgcag tcgcagatgc tgcatatagc ccagcagatc   1980
gccgcgggca tggtctacct ggcgtcccag cacttcgtgc accgcgattt ggccaccagg   2040
aactgcctgg tcggggagaa cttgctggtg aaaatcgggg actttgggat gtcccgggac   2100
gtggaaagca ctgacgaaga aagggtcggt ggccacacaa tgctgcccat cgctggatg    2160 cctccagaga gcatcatgta caggaaattc acgacggaaa gcgacgtctg gagcctgggg   2220
gtcgtgttgt gggagatttt cacctatggc aaacagccct ggtaccagct gtcaaacaat   2280
gaggtgatag agtgtatcac tcagggccga gtcctgcagc accccgcac gtgccccag    2340 gaggtgtatg agctgatgct ggggtgctgg cagcgagagc ccacatgag gaagaacatc    2400 aagggcatcc ataccctcct tcagaacttg gccaaggcat ctccggtcga actggacatt   2460
ctaggc                                                             2466
```

<210> SEQ ID NO 15
<211> LENGTH: 229
<212> TYPE: PRT
<213> ORGANISM: Homo sapiens

<400> SEQUENCE: 15

```
Ala Pro Met Lys Glu Ala Asn Ile Arg Gly Gln Gly Gly Leu Ala Tyr
  1               5                  10                  15

Pro Gly Val Arg Thr His Gly Thr Leu Glu Ser Val Asn Gly Pro Lys
             20                  25                  30

Ala Gly Ser Arg Gly Leu Thr Ser Leu Ala Asp Thr Phe Glu His Val
         35                  40                  45

Ile Glu Glu Leu Leu Asp Glu Asp Gln Lys Val Arg Pro Asn Glu Glu
     50                  55                  60

Asn Asn Lys Asp Ala Asp Leu Tyr Thr Ser Arg Val Met Leu Ser Ser
 65                  70                  75                  80

Gln Val Pro Leu Glu Pro Pro Leu Leu Phe Leu Leu Glu Glu Tyr Lys
                 85                  90                  95

Asn Tyr Leu Asp Ala Ala Asn Met Ser Met Arg Val Arg Arg His Ser
            100                 105                 110

Asp Pro Ala Arg Arg Gly Glu Leu Ser Val Cys Asp Ser Ile Ser Glu
        115                 120                 125

Trp Val Thr Ala Ala Asp Lys Lys Thr Ala Val Asp Met Ser Gly Gly
    130                 135                 140

Thr Val Thr Val Leu Glu Lys Val Pro Val Ser Lys Gly Gln Leu Lys
145                 150                 155                 160

Gln Tyr Phe Tyr Glu Thr Lys Cys Asn Pro Met Gly Tyr Thr Lys Glu
                165                 170                 175

Gly Cys Arg Gly Ile Asp Lys Arg His Trp Asn Ser Gln Cys Arg Thr
            180                 185                 190

Thr Gln Ser Tyr Val Arg Ala Leu Thr Met Asp Ser Lys Lys Arg Ile
        195                 200                 205

Gly Trp Arg Phe Ile Arg Ile Asp Thr Ser Cys Val Cys Thr Leu Thr
    210                 215                 220

Ile Lys Arg Gly Arg
225
```

<210> SEQ ID NO 16
<211> LENGTH: 690
<212> TYPE: DNA
<213> ORGANISM: Homo sapiens

<400> SEQUENCE: 16

```
gcccccatga aagaagcaaa catccgagga caaggtggct tggcctaccc aggtgtgcgg    60
acccatggga ctctggagag cgtgaatggg cccaaggcag gttcaagagg cttgacatca   120
ttggctgaca ctttcgaaca cgtgatagaa gagctgttgg atgaggacca gaaagttcgg   180
cccaatgaag aaaacaataa ggacgcagac ttgtacacgt ccagggtgat gctcagtagt   240
caagtgcctt tggagcctcc tcttctcttt ctgctgaagg aatacaaaaa ttacctagat   300
gctgcaaaca tgtccatgag ggtccggcgc cactctgacc ctgcccgccg aggggagctg   360
agcgtgtgtg acagtattag tgagtgggta acggcggcag acaaaaagac tgcagtggac   420
atgtcgggcg ggacggtcac agtccttgaa aaggtccctg tatcaaaagg ccaactgaag   480
caatacttct acgagaccaa gtgcaatccc atgggttaca aaagaagg ctgcaggggc    540
atagacaaaa ggcattggaa ctcccagtgc cgaactaccc agtcgtacgt gcgggccctt   600
accatggata gcaaaagag aattggctgg cgattcataa ggatagacac ttcttgtgta   660
tgtacattga ccattaaaag gggaagatag                                   690
```

<210> SEQ ID NO 17
<211> LENGTH: 229
<212> TYPE: PRT
<213> ORGANISM: Homo sapiens

<400> SEQUENCE: 17

```
Ala Pro Met Lys Glu Ala Asn Ile Arg Gly Gln Gly Gly Leu Ala Tyr
1               5                   10                  15

Pro Gly Val Arg Thr His Gly Thr Leu Glu Ser Val Asn Gly Pro Lys
            20                  25                  30

Ala Gly Ser Arg Gly Leu Thr Ser Leu Ala Asp Thr Phe Glu His Met
        35                  40                  45

Ile Glu Glu Leu Leu Asp Glu Asp Gln Lys Val Arg Pro Asn Glu Glu
    50                  55                  60

Asn Asn Lys Asp Ala Asp Leu Tyr Thr Ser Arg Val Met Leu Ser Ser
65                  70                  75                  80

Gln Val Pro Leu Glu Pro Pro Leu Leu Phe Leu Leu Glu Glu Tyr Lys
                85                  90                  95

Asn Tyr Leu Asp Ala Ala Asn Met Ser Met Arg Val Arg Arg His Ser
            100                 105                 110

Asp Pro Ala Arg Arg Gly Glu Leu Ser Val Cys Asp Ser Ile Ser Glu
        115                 120                 125

Trp Val Thr Ala Ala Asp Lys Lys Thr Ala Val Asp Met Ser Gly Gly
    130                 135                 140

Thr Val Thr Val Leu Glu Lys Val Pro Val Ser Lys Gly Gln Leu Lys
145                 150                 155                 160

Gln Tyr Phe Tyr Glu Thr Lys Cys Asn Pro Met Gly Tyr Thr Lys Glu
                165                 170                 175

Gly Cys Arg Gly Ile Asp Lys Arg His Trp Asn Ser Gln Cys Arg Thr
            180                 185                 190

Thr Gln Ser Tyr Val Arg Ala Leu Thr Met Asp Ser Lys Lys Arg Ile
        195                 200                 205

Gly Trp Arg Phe Ile Arg Ile Asp Thr Ser Cys Val Cys Thr Leu Thr
    210                 215                 220

Ile Lys Arg Gly Arg
225
```

<210> SEQ ID NO 18
<211> LENGTH: 119
<212> TYPE: PRT
<213> ORGANISM: Homo sapiens

<400> SEQUENCE: 18

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

<210> SEQ ID NO 19
<211> LENGTH: 744
<212> TYPE: DNA
<213> ORGANISM: Homo sapiens

<400> SEQUENCE: 19
atgaccatcc ttttccttac tatggttatt tcatactttg gttgcatgaa ggctgccccc      60
atgaaagaag caaacatccg aggacaaggt ggcttggcct acccaggtgt gcggacccat     120
gggactctgg agagcgtgaa tgggcccaag gcaggttcaa gaggcttgac atcattggct     180
gacactttcg aacacgtgat agaagagctg ttggatgagg accagaaagt tcggcccaat     240
gaagaaaaca ataaggacgc agacttgtac acgtccaggg tgatgctcag tagtcaagtg     300
cctttggagc tcctcttct ctttctgctg gaggaataca aaattaccct agatgctgca     360
aacatgtcca tgggtccg cgccactct gaccctgccc gccagggga gctgagcgtg     420 tgtgacagta ttagtgagtg ggtaacggcg gcagacaaaa agactgcagt ggacatgtcg     480
ggcgggacgt tcagtcct tgaaaaggtc cctgtatcaa aaggccaact gaagcaatac     540
ttctacgaga ccaagtgcaa tcccatgggt tacacaaaag aaggctgcag gggcatagac     600
aaaaggcatt ggaactccca gtgccgaact acccagtcgt acgtgcgggc ccttaccatg     660
gatagcaaaa agagaattgg ctggcgattc ataaggatag acacttcttg tgtatgtaca     720
ttgaccatta aaggggaag atag                                             744

<210> SEQ ID NO 20
<211> LENGTH: 18
<212> TYPE: PRT
<213> ORGANISM: Homo sapiens

<400> SEQUENCE: 20

Met Thr Ile Leu Phe Leu Thr Met Val Ile Ser Tyr Phe Gly Cys Met
1               5                   10                  15

Lys Ala

```
<210> SEQ ID NO 21
<211> LENGTH: 54
<212> TYPE: PRT
<213> ORGANISM: Homo sapiens

<400> SEQUENCE: 21

Ala Thr Gly Ala Cys Cys Ala Thr Cys Cys Thr Thr Thr Cys Cys
1               5                   10                  15

Thr Thr Ala Cys Thr Ala Thr Gly Gly Thr Thr Ala Thr Thr Thr Cys
            20                  25                  30

Ala Thr Ala Cys Thr Thr Cys Gly Gly Thr Thr Gly Cys Ala Thr Gly
        35                  40                  45

Ala Ala Gly Gly Cys Gly
    50

<210> SEQ ID NO 22
<211> LENGTH: 26
<212> TYPE: PRT
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(26)
<223> OTHER INFORMATION: An amino acid sequence for isoform 2 of an
      extended signal peptide

<400> SEQUENCE: 22

Met Phe His Gln Val Arg Arg Val Met Thr Ile Leu Phe Leu Thr Met
1               5                   10                  15

Val Ile Ser Tyr Phe Gly Cys Met Lys Ala
            20                  25

<210> SEQ ID NO 23
<211> LENGTH: 78
<212> TYPE: DNA
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(78)
<223> OTHER INFORMATION: A nucleic acid sequence for isoform 2 of an
      extended signal peptide

<400> SEQUENCE: 23
atgttccacc aggtgagaag agtgatgacc atccttttcc ttactatggt tatttcatac    60
ttcggttgca tgaaggcg                                                  78

<210> SEQ ID NO 24
<211> LENGTH: 33
<212> TYPE: PRT
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(33)
<223> OTHER INFORMATION: An amino acid sequence for isoforms 3 and 6 of
      an extended signal peptide

<400> SEQUENCE: 24

Met Gln Ser Arg Glu Glu Glu Trp Phe His Gln Val Arg Arg Val Met
1               5                   10                  15
```

-continued

```
Thr Ile Leu Phe Leu Thr Met Val Ile Ser Tyr Phe Gly Cys Met Lys
            20                  25                  30
Ala
```

<210> SEQ ID NO 25
<211> LENGTH: 99
<212> TYPE: DNA
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(99)
<223> OTHER INFORMATION: A nucleic acid sequence for isoforms 3 and 6 of
      an extended signal peptide

<400> SEQUENCE: 25

```
atgcagagcc gggaagagga atggttccac caggtgagaa gagtgatgac catccttttc    60
cttactatgg ttatttcata cttcggttgc atgaaggcg                           99
```

<210> SEQ ID NO 26
<211> LENGTH: 47
<212> TYPE: PRT
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(47)
<223> OTHER INFORMATION: An amino acid sequence for isoform 5 of an
      extended signal peptide

<400> SEQUENCE: 26

```
Met Leu Cys Ala Ile Ser Leu Cys Ala Arg Val Arg Lys Leu Arg Ser
1               5                   10                  15

Ala Gly Arg Cys Gly Lys Phe His Gln Val Arg Arg Val Met Thr Ile
            20                  25                  30

Leu Phe Leu Thr Met Val Ile Ser Tyr Phe Gly Cys Met Lys Ala
        35                  40                  45
```

<210> SEQ ID NO 27
<211> LENGTH: 141
<212> TYPE: DNA
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(141)
<223> OTHER INFORMATION: A nucleic acid sequence for isoform 5 of an
      extended signal peptide

<400> SEQUENCE: 27

```
atgctctgtg cgatttcatt gtgtgctcgc gttcgcaagc tccgtagtgc aggaaggtgc    60
gggaagttcc accaggtgag aagagtgatg accatccttt tccttactat ggttatttca   120
tacttcggtt gcatgaaggc g                                             141
```

<210> SEQ ID NO 28
<211> LENGTH: 100
<212> TYPE: PRT
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(100)

<223> OTHER INFORMATION: An amino acid sequence for isoform 4 of an
      extended signal peptide

<400> SEQUENCE: 28

Met Cys Gly Ala Thr Ser Phe Leu His Glu Cys Thr Arg Leu Ile Leu
1               5                   10                  15

Val Thr Thr Gln Asn Ala Glu Phe Leu Gln Lys Gly Leu Gln Val His
            20                  25                  30

Thr Cys Phe Gly Val Tyr Pro His Ala Ser Val Trp His Asp Cys Ala
        35                  40                  45

Ser Gln Lys Lys Gly Cys Ala Val Tyr Leu His Val Ser Val Glu Phe
    50                  55                  60

Asn Lys Leu Ile Pro Glu Asn Gly Phe Ile Lys Phe His Gln Val Arg
65                  70                  75                  80

Arg Val Met Thr Ile Leu Phe Leu Thr Met Val Ile Ser Tyr Phe Gly
                85                  90                  95

Cys Met Lys Ala
            100

<210> SEQ ID NO 29
<211> LENGTH: 300
<212> TYPE: DNA
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(300)
<223> OTHER INFORMATION: A nucleic acid sequence for isoform 4 of an
      extended signal peptide

<400> SEQUENCE: 29
atgtgtggag ccaccagttt tctccatgag tgcacaaggt taatccttgt tactactcag      60
aatgctgagt ttctacagaa agggttgcag gtccacacat gttttggcgt ctacccacac     120
gcttctgtat ggcatgactg tgcatcccag aagaagggct gtgctgtgta cctccacgtt     180
tcagtggaat taacaaaact gatccctgaa aatggtttca taaagttcca ccaggtgaga     240
agagtgatga ccatcctttt ccttactatg gttatttcat acttcggttg catgaaggcg     300

<210> SEQ ID NO 30
<211> LENGTH: 20
<212> TYPE: PRT
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(20)
<223> OTHER INFORMATION: Amino acid sequence of the signal peptide for
      the agonist: QTA003P (IL-2 signal)

<400> SEQUENCE: 30

Met Tyr Arg Met Gln Leu Leu Ser Cys Ile Ala Leu Ser Leu Ala Leu
1               5                   10                  15

Val Thr Asn Ser
            20

<210> SEQ ID NO 31
<211> LENGTH: 60
<212> TYPE: DNA
<213> ORGANISM: Artificial Sequence
<220> FEATURE:
<223> OTHER INFORMATION: synthetic sequence

```
<220> FEATURE:
<221> NAME/KEY: Sig_peptide
<222> LOCATION: (1)..(60)
<223> OTHER INFORMATION: Nucleic acid sequence of the signal peptide for
      the agonist: QTA003P (IL-2 signal)

<400> SEQUENCE: 31
atgtacagga tgcaactcct gtcttgcatt gcactaagtc ttgcacttgt cacaaacagt     60

<210> SEQ ID NO 32
<211> LENGTH: 22
<212> TYPE: PRT
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(22)
<223> OTHER INFORMATION: Amino acid sequence of the signal peptide for
      the agonist: QTA004P

<400> SEQUENCE: 32

Met Lys Arg Arg Val Met Ile Ile Leu Phe Leu Thr Met Val Ile Ser
1               5                   10                  15

Tyr Phe Gly Cys Met Lys
            20

<210> SEQ ID NO 33
<211> LENGTH: 70
<212> TYPE: DNA
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(70)
<223> OTHER INFORMATION: Nucleic acid sequence of the signal peptide for
      the agonist: QTA004P

<400> SEQUENCE: 33
atgaaaagaa gagtgatgat catccttttc cttactatgg ttatttcata cttcggttgc     60
atgaagagcg                                                            70

<210> SEQ ID NO 34
<211> LENGTH: 20
<212> TYPE: PRT
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(20)
<223> OTHER INFORMATION: Amino acid sequence of the signal peptide for
      the agonist: QTA009P (modified IL-2)

<400> SEQUENCE: 34

Met Arg Arg Met Gln Leu Leu Leu Leu Ile Ala Leu Ser Leu Ala Leu
1               5                   10                  15

Val Thr Asn Ser
            20

<210> SEQ ID NO 35
<211> LENGTH: 60
<212> TYPE: DNA
<213> ORGANISM: Artificial Sequence
<220> FEATURE:
<223> OTHER INFORMATION: synthetic sequence
<220> FEATURE:
```

```
<221> NAME/KEY: Sig_peptide
<222> LOCATION: (1)..(60)
<223> OTHER INFORMATION: Nucleic acid sequence of the signal peptide for
      the agonist: QTA009P (modified IL-2)

<400> SEQUENCE: 35
atgaggagga tgcaactcct gctcctgatt gcactaagtc ttgcacttgt cacaaacagt    60

<210> SEQ ID NO 36
<211> LENGTH: 21
<212> TYPE: PRT
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(21)
<223> OTHER INFORMATION: Amino acid sequence of the signal peptide for
      the agonist: QTA010P

<400> SEQUENCE: 36

Met Arg Arg Met Gln Leu Leu Leu Leu Thr Met Val Ile Ser Tyr Phe
1               5                   10                  15

Gly Cys Met Lys Ala
            20

<210> SEQ ID NO 37
<211> LENGTH: 63
<212> TYPE: DNA
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(63)
<223> OTHER INFORMATION: Nucleic acid sequence of the signal peptide for
      the agonist: QTA010P

<400> SEQUENCE: 37
atgaggagga tgcaactcct gctcctgact atggttattt catacttcgg ttgcatgaag    60
gcg                                                                  63

<210> SEQ ID NO 38
<211> LENGTH: 18
<212> TYPE: PRT
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(18)
<223> OTHER INFORMATION: Amino acid sequence of the signal peptide for
      the agonist: QTA0012P

<400> SEQUENCE: 38

Met Arg Ile Leu Leu Leu Thr Met Val Ile Ser Tyr Phe Gly Cys Met
1               5                   10                  15

Lys Ala

<210> SEQ ID NO 39
<211> LENGTH: 54
<212> TYPE: DNA
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(54)
```

<223> OTHER INFORMATION: Nucleic acid sequence of the signal peptide for
      the agonist: QTA0012P

<400> SEQUENCE: 39
atgagaatcc ttcttcttac tatggttatt tcatacttcg gttgcatgaa ggcg                54

<210> SEQ ID NO 40
<211> LENGTH: 19
<212> TYPE: PRT
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(19)
<223> OTHER INFORMATION: Amino acid sequence of the signal peptide for
      the agonist: QTA0013P

<400> SEQUENCE: 40

Met Arg Arg Ile Leu Phe Leu Thr Met Val Ile Ser Tyr Phe Gly Cys
1               5                   10                  15

Met Lys Ala

<210> SEQ ID NO 41
<211> LENGTH: 57
<212> TYPE: DNA
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(57)
<223> OTHER INFORMATION: Nucleic acid sequence of the signal peptide for
      the agonist: QTA0013P

<400> SEQUENCE: 41
atgagaagaa tccttttcct tactatggtt atttcatact tcggttgcat gaaggcg           57

<210> SEQ ID NO 42
<211> LENGTH: 18
<212> TYPE: PRT
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(18)
<223> OTHER INFORMATION: Amino acid sequence of the signal peptide for
      the agonist: QTA0014P

<400> SEQUENCE: 42

Met Arg Arg Phe Leu Phe Leu Leu Val Ile Ser Tyr Phe Gly Cys Met
1               5                   10                  15

Lys Ala

<210> SEQ ID NO 43
<211> LENGTH: 54
<212> TYPE: DNA
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(54)
<223> OTHER INFORMATION: Nucleic acid sequence of the signal peptide for
      the agonist: QTA0014P

<400> SEQUENCE: 43

```
atgaggaggt ccttttcct tcttgttatt tcatacttcg gttgcatgaa ggcg        54
```

```
<210> SEQ ID NO 44
<211> LENGTH: 15
<212> TYPE: PRT
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(15)
<223> OTHER INFORMATION: Amino acid sequence of the signal peptide for
      the agonist: QTA0015P

<400> SEQUENCE: 44

Met Arg Arg Phe Leu Phe Leu Leu Tyr Phe Gly Cys Met Lys Ala
1               5                   10                  15
```

```
<210> SEQ ID NO 45
<211> LENGTH: 45
<212> TYPE: DNA
<213> ORGANISM: Artificial Sequence
<220> FEATURE:
<223> OTHER INFORMATION: synthetic sequence
<220> FEATURE:
<221> NAME/KEY: Sig_peptide
<222> LOCATION: (1)..(45)
<223> OTHER INFORMATION: Nucleic acid sequence of the signal peptide for
      the agonist: QTA0015P

<400> SEQUENCE: 45
atgaggaggt cctttttcct tctttacttc ggttgcatga aggcg                  45
```

```
<210> SEQ ID NO 46
<211> LENGTH: 130
<212> TYPE: DNA
<213> ORGANISM: Unknown
<220> FEATURE:
<223> OTHER INFORMATION: DNA sequence of a left ITR

<400> SEQUENCE: 46
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact  120
aggggttcct                                                         130
```

```
<210> SEQ ID NO 47
<211> LENGTH: 141
<212> TYPE: DNA
<213> ORGANISM: Unknown
<220> FEATURE:
<223> OTHER INFORMATION: DNA sequence of a right ITR

<400> SEQUENCE: 47
aggaacccct agtgatggag ttggccactc cctctctgcg cgctcgctcg ctcactgagg   60
ccgggcgacc aaaggtcgcc cgacgcccgg gctttgcccg gcggcctca gtgagcgagc   120 gagcgcgcag ctgcctgcag g                                            141
```

```
<210> SEQ ID NO 48
<211> LENGTH: 584
<212> TYPE: DNA
<213> ORGANISM: Artificial Sequence
<220> FEATURE:
<223> OTHER INFORMATION: synthetic sequence
<220> FEATURE:
<221> NAME/KEY: Promoter
<222> LOCATION: (1)..(584)
```

<223> OTHER INFORMATION: Truncated CAG nucleotide promoter sequence.

<400> SEQUENCE: 48

```
gcgttacata acttacggta atggcccgc ctggctgacc gcccaacgac ccccgcccat    60
tgacgtcaat aatgacgtat gttcccatag taacgccaat agggactttc cattgacgtc   120
aatgggtgga ctatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggtcga ggtgagcccc acgttctgct tcactctccc catctccccc ccctccccac   360
ccccaatttt gtatttattt atttttaat tattttgtgc agcgatgggg gcggggggg    420
gggggggcg cgcgccaggc ggggcgggc ggggcgaggg gcgggcggg gcgaggcgga    480
gaggtgcggc ggcagccaat cagagcggcg cgctccgaaa gtttccttt atggcgaggc    540
ggcggcggcg gcggccctat aaaaagcgaa gcgcgcggcg ggcg                    584
```

<210> SEQ ID NO 49
<211> LENGTH: 210
<212> TYPE: PRT
<213> ORGANISM: Homo sapiens

<400> SEQUENCE: 49

```
Met Leu Pro Leu Pro Ser Cys Ser Leu Pro Ile Leu Leu Phe Leu
1               5                   10                  15
Leu Pro Ser Val Pro Ile Glu Ser Gln Pro Pro Ser Thr Leu Pro
            20                  25                  30
Pro Phe Leu Ala Pro Glu Trp Asp Leu Leu Ser Pro Arg Val Val Leu
        35                  40                  45
Ser Arg Gly Ala Pro Ala Gly Pro Pro Leu Leu Phe Leu Leu Glu Ala
    50                  55                  60
Gly Ala Phe Arg Glu Ser Ala Gly Ala Pro Ala Asn Arg Ser Arg Arg
65                  70                  75                  80
Gly Val Ser Glu Thr Ala Pro Ala Ser Arg Arg Gly Glu Leu Ala Val
                85                  90                  95
Cys Asp Ala Val Ser Gly Trp Val Thr Asp Arg Arg Thr Ala Val Asp
                100                 105                 110
Leu Arg Gly Arg Glu Val Glu Val Leu Gly Glu Val Pro Ala Ala Gly
            115                 120                 125
Gly Ser Pro Leu Arg Gln Tyr Phe Phe Glu Thr Arg Cys Lys Ala Asp
        130                 135                 140
Asn Ala Glu Glu Gly Gly Pro Gly Ala Gly Gly Gly Cys Arg Gly
145                 150                 155                 160
Val Asp Arg Arg His Trp Val Ser Glu Cys Lys Ala Lys Gln Ser Tyr
                165                 170                 175
Val Arg Ala Leu Thr Ala Asp Ala Gln Gly Arg Val Gly Trp Arg Trp
            180                 185                 190
Ile Arg Ile Asp Thr Ala Cys Val Cys Thr Leu Leu Ser Arg Thr Gly
        195                 200                 205
Arg Ala
    210
```

<210> SEQ ID NO 50
<211> LENGTH: 630
<212> TYPE: DNA
<213> ORGANISM: Homo sapiens

<400> SEQUENCE: 50

```
atgctccctc tcccctcatg ctccctcccc atcctcctcc ttttcctcct ccccagtgtg    60
ccaattgagt cccaaccccc accctcaaca ttgccccctt ttctggcccc tgagtgggac   120
cttctctccc cccgagtagt cctgtctagg ggtgccccty ctgggccccc tctgctcttc   180
ctgctggagg ctggggcctt tcgggagtca gcaggtgccc cggccaaccg cagccggcgt   240
ggggtgagcg aaactgcacc agcgagtcgt cggggtgagc tggctgtgtg cgatgcagtc   300
agtggctggg tgacagaccg ccggaccgct gtggacttgc gtgggcgcga ggtggaggtg   360
ttgggcgagg tgcctgcagc tggcggcagt cccctccgcc agtacttctt tgaaacccgc   420
tgcaaggctg ataacgctga ggaaggtggc ccgggggcag gtggaggggg ctgccgggga   480
gtggacagga ggcactgggt atctgagtgc aaggccaagc agtcctatgt gcgggcattg   540
accgctgatg cccagggccg tgtgggctgg cgatggattc gaattgacac tgcctgcgtc   600
tgcacactcc tcagccggac tggccgggcc                                   630
```

<210> SEQ ID NO 51
<211> LENGTH: 24
<212> TYPE: PRT
<213> ORGANISM: Homo sapiens

<400> SEQUENCE: 51

```
Met Leu Pro Leu Pro Ser Cys Ser Leu Pro Ile Leu Leu Leu Phe Leu
1               5                   10                  15

Leu Pro Ser Val Pro Ile Glu Ser
            20
```

<210> SEQ ID NO 52
<211> LENGTH: 72
<212> TYPE: DNA
<213> ORGANISM: Homo sapiens

<400> SEQUENCE: 52

```
atgctccctc tcccctcatg ctccctcccc atcctcctcc ttttcctcct ccccagtgtg    60
ccaattgagt cc                                                       72
```

<210> SEQ ID NO 53
<211> LENGTH: 56
<212> TYPE: PRT
<213> ORGANISM: Homo sapiens

<400> SEQUENCE: 53

```
Gln Pro Pro Pro Ser Thr Leu Pro Pro Phe Leu Ala Pro Glu Trp Asp
1               5                   10                  15

Leu Leu Ser Pro Arg Val Val Leu Ser Arg Gly Ala Pro Ala Gly Pro
            20                  25                  30

Pro Leu Leu Phe Leu Leu Glu Ala Gly Ala Phe Arg Glu Ser Ala Gly
                35                  40                  45

Ala Pro Ala Asn Arg Ser Arg Arg
        50                  55
```

<210> SEQ ID NO 54
<211> LENGTH: 168
<212> TYPE: DNA
<213> ORGANISM: Homo sapiens

<400> SEQUENCE: 54

```
caaccccccac cctcaacatt gccccctttt ctggccccctg agtgggacct tctctccccc    60
cgagtagtcc tgtctagggg tgcccctgct gggcccccctc tgctcttcct gctggaggct   120
ggggcctttc gggagtcagc aggtgccccg gccaaccgca gccggcgt                 168
```

<210> SEQ ID NO 55
<211> LENGTH: 130
<212> TYPE: PRT
<213> ORGANISM: Homo sapiens

<400> SEQUENCE: 55

```
Gly Val Ser Glu Thr Ala Pro Ala Ser Arg Arg Gly Glu Leu Ala Val
  1               5                  10                  15

Cys Asp Ala Val Ser Gly Trp Val Thr Asp Arg Arg Thr Ala Val Asp
             20                  25                  30

Leu Arg Gly Arg Glu Val Glu Val Leu Gly Glu Val Pro Ala Ala Gly
         35                  40                  45

Gly Ser Pro Leu Arg Gln Tyr Phe Phe Glu Thr Arg Cys Lys Ala Asp
     50                  55                  60

Asn Ala Glu Glu Gly Gly Pro Gly Ala Gly Gly Gly Cys Arg Gly
 65                  70                  75                  80

Val Asp Arg Arg His Trp Val Ser Glu Cys Lys Ala Lys Gln Ser Tyr
                 85                  90                  95

Val Arg Ala Leu Thr Ala Asp Ala Gln Gly Arg Val Gly Trp Arg Trp
            100                 105                 110

Ile Arg Ile Asp Thr Ala Cys Val Cys Thr Leu Leu Ser Arg Thr Gly
        115                 120                 125

Arg Ala
    130
```

<210> SEQ ID NO 56
<211> LENGTH: 390
<212> TYPE: DNA
<213> ORGANISM: Homo sapiens

<400> SEQUENCE: 56

```
ggggtgagcg aaactgcacc agcgagtcgt cggggtgagc tggctgtgtg cgatgcagtc    60
agtggctggg tgacagaccg ccggaccgct gtggacttgc gtgggcgcga ggtggaggtg   120
ttgggcgagg tgcctgcagc tggcggcagt cccctccgcc agtacttctt tgaaacccgc   180
tgcaaggctg ataacgctga ggaaggtggc ccggggcag gtggagggggg ctgccgggga   240 gtggacagga ggcactgggt atctgagtgc aaggccaagc agtcctatgt gcgggcattg   300
accgctgatg cccagggccg tgtgggctgg cgatggattc gaattgacac tgcctgcgtc   360
tgcacactcc tcagccggac tggccgggcc                                    390
```

<210> SEQ ID NO 57
<211> LENGTH: 592
<212> TYPE: DNA
<213> ORGANISM: Marmota monax

<400> SEQUENCE: 57

```
aatcaacctc tggattacaa aatttgtgaa agattgactg gtattcttaa ctatgttgct    60
ccttttacgc tatgtggata cgctgcttta atgcctttgt atcatgctat gcttcccgt   120 atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240
```

```
ggttggggca ttgccaccac ctgtcagctc ctttccggga ctttcgcttt cccctccct      300 attgccacgg cggaactcat cgccgcctgc cttgcccgct gctggacagg ggctcggctg      360
ttgggcactg acaattccgt ggtgttgtcg gggaagctga cgtcctttcc atggctgctc      420
gcctgtgttg ccacctggat tctgcgcggg acgtccttct gctacgtccc ttcggccctc      480
aatccagcgg accttccttc ccgcggcctg ctgccggctc tgcggcctct ccgcgtctt       540 cgccttcgcc ctcagacgag tcggatctcc ctttgggccg cctccccgcc tg             592
```

```
<210> SEQ ID NO 58
<211> LENGTH: 247
<212> TYPE: DNA
<213> ORGANISM: Artificial Sequence
<220> FEATURE:
<223> OTHER INFORMATION: synthetic sequence
<220> FEATURE:
<221> NAME/KEY: Enhancer
<222> LOCATION: (1)..(247)
<223> OTHER INFORMATION: Truncated WHPE nucleotide sequence. Beta
      element has been deleted.

<400> SEQUENCE: 58
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttag ttcttgccac ggcggaactc     180
atcgccgcct gccttgcccg ctgctggaca ggggctcggc tgttgggcac tgacaattcc     240
gtggtgt                                                               247
```

```
<210> SEQ ID NO 59
<211> LENGTH: 224
<212> TYPE: DNA
<213> ORGANISM: Simian virus 40

<400> SEQUENCE: 59
agcagacatg ataagataca ttgatgagtt tggacaaacc acaactagaa tgcagtgaaa      60
aaaatgcttt atttgtgaaa tttgtgatgc tattgcttta tttgtaacca ttataagctg     120
caataaacaa gttaacaaca caattgcat tcattttatg tttcaggttc aggggggaggt    180 gtgggaggtt ttttaaagca agtaaaacct ctacaaatgt ggta                     224
```

```
<210> SEQ ID NO 60
<211> LENGTH: 18
<212> TYPE: PRT
<213> ORGANISM: Homo sapiens

<400> SEQUENCE: 60

Met Thr Ile Leu Phe Leu Thr Met Val Ile Ser Tyr Phe Gly Cys Met
1               5                   10                  15

Lys Ala
```

```
<210> SEQ ID NO 61
<211> LENGTH: 54
<212> TYPE: DNA
<213> ORGANISM: Homo sapiens

<400> SEQUENCE: 61
atgaccatcc ttttccttac tatggttatt tcatacttcg gttgcatgaa ggcg            54
```

```
<210> SEQ ID NO 62
<211> LENGTH: 18
```

<212> TYPE: PRT
<213> ORGANISM: Artificial Sequence
<220> FEATURE:
<223> OTHER INFORMATION: Amino acid sequnece: Same sequence as SEQ ID
    No. 60 but the first "T" of SEQ ID No. 60 has been replaced by a
    "R".

<400> SEQUENCE: 62

Met Arg Ile Leu Phe Leu Thr Met Val Ile Ser Tyr Phe Gly Cys Met
1               5                   10                  15

Lys Ala

<210> SEQ ID NO 63
<211> LENGTH: 54
<212> TYPE: DNA
<213> ORGANISM: Artificial Sequence
<220> FEATURE:
<223> OTHER INFORMATION: Nucleic acid sequnece: Same sequence as SEQ ID
    No. 61 but "acc" of SEQ ID No. 61 has been replaced by a "aga".

<400> SEQUENCE: 63
atgagaatcc ttttccttac tatggttatt tcatacttcg gttgcatgaa ggcg          54

<210> SEQ ID NO 64
<211> LENGTH: 19
<212> TYPE: PRT
<213> ORGANISM: Artificial Sequence
<220> FEATURE:
<223> OTHER INFORMATION: Amino acid sequnece: Same sequence as SEQ ID
    No. 60 but the first "T" of SEQ ID No. 60 has been replaced by
    "RR".

<400> SEQUENCE: 64

Met Arg Arg Ile Leu Phe Leu Thr Met Val Ile Ser Tyr Phe Gly Cys
1               5                   10                  15

Met Lys Ala

<210> SEQ ID NO 65
<211> LENGTH: 57
<212> TYPE: DNA
<213> ORGANISM: Artificial Sequence
<220> FEATURE:
<223> OTHER INFORMATION: Nucleic acid sequnece: Same sequence as SEQ ID
    No. 61 but "acc" of SEQ ID No. 61 has been replaced by a "agaaga".

<400> SEQUENCE: 65
atgagaagaa tcctttttcct tactatggtt atttcatact tcggttgcat gaaggcg       57

<210> SEQ ID NO 66
<211> LENGTH: 20
<212> TYPE: PRT
<213> ORGANISM: Artificial Sequence
<220> FEATURE:
<223> OTHER INFORMATION: Amino acid sequnece: Same sequence as SEQ ID
    No. 60 but the first "T" of SEQ ID No. 60 has been replaced by
    "RRR".

<400> SEQUENCE: 66

Met Arg Arg Arg Ile Leu Phe Leu Thr Met Val Ile Ser Tyr Phe Gly
1               5                   10                  15

Cys Met Lys Ala
            20

<210> SEQ ID NO 67
<211> LENGTH: 60
<212> TYPE: DNA

```
<213> ORGANISM: Artificial Sequence
<220> FEATURE:
<223> OTHER INFORMATION: Nucleic acid sequnece: Same sequence as SEQ ID
      No. 61 but "acc" of SEQ ID No. 61 has been replaced by a
      "agaagaaga".

<400> SEQUENCE: 67
atgagaagaa gaatcctttt ccttactatg gttatttcat acttcggttg catgaaggcg      60

<210> SEQ ID NO 68
<211> LENGTH: 18
<212> TYPE: PRT
<213> ORGANISM: Artificial Sequence
<220> FEATURE:
<223> OTHER INFORMATION: Amino acid sequnece: Same sequence as SEQ ID
      No. 60 but the first "T" of SEQ ID No. 60 has been replaced by a
      "K".

<400> SEQUENCE: 68

Met Lys Ile Leu Phe Leu Thr Met Val Ile Ser Tyr Phe Gly Cys Met
1               5                   10                  15

Lys Ala

<210> SEQ ID NO 69
<211> LENGTH: 54
<212> TYPE: DNA
<213> ORGANISM: Artificial Sequence
<220> FEATURE:
<223> OTHER INFORMATION: Nucleic acid sequnece: Same sequence as SEQ ID
      No. 61 but "acc" of SEQ ID No. 61 has been replaced by a "aaa".

<400> SEQUENCE: 69
atgaaaatcc ttttccttac tatggttatt tcatacttcg gttgcatgaa ggcg            54

<210> SEQ ID NO 70
<211> LENGTH: 19
<212> TYPE: PRT
<213> ORGANISM: Artificial Sequence
<220> FEATURE:
<223> OTHER INFORMATION: Amino acid sequnece: Same sequence as SEQ ID
      No. 60 but the first "T" of SEQ ID No. 60 has been replaced by a
      "KK".

<400> SEQUENCE: 70

Met Lys Lys Ile Leu Phe Leu Thr Met Val Ile Ser Tyr Phe Gly Cys
1               5                   10                  15

Met Lys Ala

<210> SEQ ID NO 71
<211> LENGTH: 57
<212> TYPE: DNA
<213> ORGANISM: Artificial Sequence
<220> FEATURE:
<223> OTHER INFORMATION: Nucleic acid sequnece: Same sequence as SEQ ID
      No. 61 but "acc" of SEQ ID No. 61 has been replaced by a "aaaaka".

<400> SEQUENCE: 71
atgaaaakaa tccttttcct tactatggtt atttcatact tcggttgcat gaaggcg         57

<210> SEQ ID NO 72
<211> LENGTH: 20
<212> TYPE: PRT
<213> ORGANISM: Artificial Sequence
<220> FEATURE:
<223> OTHER INFORMATION: Amino acid sequnece: Same sequence as SEQ ID
      No. 60 but the first "T" of SEQ ID No. 60 has been replaced by a
      "KKK".
```

<400> SEQUENCE: 72

Met Lys Lys Lys Ile Leu Phe Leu Thr Met Val Ile Ser Tyr Phe Gly
1               5                   10                  15

Cys Met Lys Ala
            20

<210> SEQ ID NO 73
<211> LENGTH: 60
<212> TYPE: DNA
<213> ORGANISM: Artificial Sequence
<220> FEATURE:
<223> OTHER INFORMATION: Nucleic acid sequnece: Same sequence as SEQ ID
      No. 61 but "acc" of SEQ ID No. 61 has been replaced by a
      "aaaaaaaaa".

<400> SEQUENCE: 73
atgaaaaaaa aaatcctttt ccttactatg gttatttcat acttcggttg catgaaggcg      60

<210> SEQ ID NO 74
<211> LENGTH: 20
<212> TYPE: PRT
<213> ORGANISM: Artificial Sequence
<220> FEATURE:
<223> OTHER INFORMATION: Amino acid sequnece: Same sequence as SEQ ID
      No. 60 but the first "T" of SEQ ID No. 60 has been replaced by a
      "KRR".

<400> SEQUENCE: 74

Met Lys Arg Arg Ile Leu Phe Leu Thr Met Val Ile Ser Tyr Phe Gly
1               5                   10                  15

Cys Met Lys Ala
            20

<210> SEQ ID NO 75
<211> LENGTH: 60
<212> TYPE: DNA
<213> ORGANISM: Artificial Sequence
<220> FEATURE:
<223> OTHER INFORMATION: Nucleic acid sequnece: Same sequence as SEQ ID
      No. 61 but "acc" of SEQ ID No. 61 has been replaced by a
      "aaaagaaga".

<400> SEQUENCE: 75
atgaaaagaa gaatcctttt ccttactatg gttatttcat acttcggttg catgaaggcg      60

<210> SEQ ID NO 76
<211> LENGTH: 20
<212> TYPE: PRT
<213> ORGANISM: Artificial Sequence
<220> FEATURE:
<223> OTHER INFORMATION: Amino acid sequnece: Same sequence as SEQ ID
      No. 60 but the first "T" of SEQ ID No. 60 has been replaced by a
      "RKR".

<400> SEQUENCE: 76

Met Arg Lys Arg Ile Leu Phe Leu Thr Met Val Ile Ser Tyr Phe Gly
1               5                   10                  15

Cys Met Lys Ala
            20

<210> SEQ ID NO 77
<211> LENGTH: 60
<212> TYPE: DNA
<213> ORGANISM: Artificial Sequence
<220> FEATURE:

<223> OTHER INFORMATION: Nucleic acid sequnece: Same sequence as SEQ ID
      No. 61 but "acc" of SEQ ID No. 61 has been replaced by a
      "agaaaaaga".

<400> SEQUENCE: 77
atgagaaaaa gaatcctttt ccttactatg gttatttcat acttcggttg catgaaggcg    60

<210> SEQ ID NO 78
<211> LENGTH: 20
<212> TYPE: PRT
<213> ORGANISM: Artificial Sequence
<220> FEATURE:
<223> OTHER INFORMATION: Amino acid sequnece: Same sequence as SEQ ID
      No. 60 but the first "T" of SEQ ID No. 60 has been replaced by a
      "RRK".

<400> SEQUENCE: 78

Met Arg Arg Lys Ile Leu Phe Leu Thr Met Val Ile Ser Tyr Phe Gly
1               5                   10                  15

Cys Met Lys Ala
            20

<210> SEQ ID NO 79
<211> LENGTH: 60
<212> TYPE: DNA
<213> ORGANISM: Artificial Sequence
<220> FEATURE:
<223> OTHER INFORMATION: Nucleic acid sequnece: Same sequence as SEQ ID
      No. 61 but "acc" of SEQ ID No. 61 has been replaced by a
      "agaagaaaa".

<400> SEQUENCE: 79
atgagaagaa aaatcctttt ccttactatg gttatttcat acttcggttg catgaaggcg    60

<210> SEQ ID NO 80
<211> LENGTH: 20
<212> TYPE: PRT
<213> ORGANISM: Artificial Sequence
<220> FEATURE:
<223> OTHER INFORMATION: Amino acid sequnece: Same sequence as SEQ ID
      No. 60 but the first "T" of SEQ ID No. 60 has been replaced by a
      "KKR".

<400> SEQUENCE: 80

Met Lys Lys Arg Ile Leu Phe Leu Thr Met Val Ile Ser Tyr Phe Gly
1               5                   10                  15

Cys Met Lys Ala
            20

<210> SEQ ID NO 81
<211> LENGTH: 60
<212> TYPE: DNA
<213> ORGANISM: Artificial Sequence
<220> FEATURE:
<223> OTHER INFORMATION: Nucleic acid sequnece: Same sequence as SEQ ID
      No. 61 but "acc" of SEQ ID No. 61 has been replaced by a
      "aaaaaaaga".

<400> SEQUENCE: 81
atgaaaaaaa gaatcctttt ccttactatg gttatttcat acttcggttg catgaaggcg    60

<210> SEQ ID NO 82
<211> LENGTH: 18
<212> TYPE: PRT
<213> ORGANISM: Artificial Sequence
<220> FEATURE:
<223> OTHER INFORMATION: Amino acid sequnece: Same sequence as SEQ ID -continued No. 60 but the "ILFL" sequence of SEQ ID No. 60 has been replaced by "FLFL".

<400> SEQUENCE: 82

Met Thr Phe Leu Phe Leu Thr Met Val Ile Ser Tyr Phe Gly Cys Met
1               5                   10                  15

Lys Ala

<210> SEQ ID NO 83
<211> LENGTH: 54
<212> TYPE: DNA
<213> ORGANISM: Artificial Sequence
<220> FEATURE:
<223> OTHER INFORMATION: Amino acid sequnece: Same sequence as SEQ ID
      No. 6' but the "atccttttcctt" sequence of SEQ ID No. 61 has been
      replaced by "ttccttttcctt".

<400> SEQUENCE: 83
atgaccttcc ttttccttac tatggttatt tcatacttcg gttgcatgaa ggcg        54

<210> SEQ ID NO 84
<211> LENGTH: 18
<212> TYPE: PRT
<213> ORGANISM: Artificial Sequence
<220> FEATURE:
<223> OTHER INFORMATION: Amino acid sequnece: Same sequence as SEQ ID
      No. 60 but the "ILFL" sequence of SEQ ID No. 60 has been replaced
      by "FFFL".

<400> SEQUENCE: 84

Met Thr Phe Phe Phe Leu Thr Met Val Ile Ser Tyr Phe Gly Cys Met
1               5                   10                  15

Lys Ala

<210> SEQ ID NO 85
<211> LENGTH: 54
<212> TYPE: DNA
<213> ORGANISM: Artificial Sequence
<220> FEATURE:
<223> OTHER INFORMATION: Amino acid sequnece: Same sequence as SEQ ID
      No. 61 but the "atccttttcctt" sequence of SEQ ID No. 61 has been
      replaced by "ttcttcttcctt".

<400> SEQUENCE: 85
atgaccttct cttccttac tatggttatt tcatacttcg gttgcatgaa ggcg         54

<210> SEQ ID NO 86
<211> LENGTH: 18
<212> TYPE: PRT
<213> ORGANISM: Artificial Sequence
<220> FEATURE:
<223> OTHER INFORMATION: Amino acid sequnece: Same sequence as SEQ ID
      No. 60 but the "ILFL" sequence of SEQ ID No. 60 has been replaced
      by "FIFL".

<400> SEQUENCE: 86

Met Thr Phe Ile Phe Leu Thr Met Val Ile Ser Tyr Phe Gly Cys Met
1               5                   10                  15

Lys Ala

<210> SEQ ID NO 87
<211> LENGTH: 54
<212> TYPE: DNA
<213> ORGANISM: Artificial Sequence
<220> FEATURE:
<223> OTHER INFORMATION: Amino acid sequnece: Same sequence as SEQ ID No. 61 but the "atccttttcctt" sequence of SEQ ID No. 61 has been replaced by "ttcatcttcctt".

<400> SEQUENCE: 87
atgaccttca tcttccttac tatggttatt tcatacttcg gttgcatgaa ggcg      54

<210> SEQ ID NO 88
<211> LENGTH: 18
<212> TYPE: PRT
<213> ORGANISM: Artificial Sequence
<220> FEATURE:
<223> OTHER INFORMATION: Amino acid sequnece: Same sequence as SEQ ID
      No. 60 but the "ILFL" sequence of SEQ ID No. 60 has been replaced
      by "FIFI".

<400> SEQUENCE: 88

Met Thr Phe Ile Phe Ile Thr Met Val Ile Ser Tyr Phe Gly Cys Met
1               5                   10                  15

Lys Ala

<210> SEQ ID NO 89
<211> LENGTH: 54
<212> TYPE: DNA
<213> ORGANISM: Artificial Sequence
<220> FEATURE:
<223> OTHER INFORMATION: Amino acid sequnece: Same sequence as SEQ ID
      No. 61 but the "atccttttcctt" sequence of SEQ ID No. 61 has been
      replaced by "ttcatcttcatc".

<400> SEQUENCE: 89
atgaccttca tcttcatcac tatggttatt tcatacttcg gttgcatgaa ggcg      54

<210> SEQ ID NO 90
<211> LENGTH: 18
<212> TYPE: PRT
<213> ORGANISM: Artificial Sequence
<220> FEATURE:
<223> OTHER INFORMATION: Amino acid sequnece: Same sequence as SEQ ID
      No. 60 but the "ILFL" sequence of SEQ ID No. 60 has been replaced
      by "FVFI".

<400> SEQUENCE: 90

Met Thr Phe Val Phe Ile Thr Met Val Ile Ser Tyr Phe Gly Cys Met
1               5                   10                  15

Lys Ala

<210> SEQ ID NO 91
<211> LENGTH: 54
<212> TYPE: DNA
<213> ORGANISM: Artificial Sequence
<220> FEATURE:
<223> OTHER INFORMATION: Amino acid sequnece: Same sequence as SEQ ID
      No. 61 but the "atccttttcctt" sequence of SEQ ID No. 61 has been
      replaced by "ttcgttttcatc".

<400> SEQUENCE: 91
atgaccttcg ttttcatcac tatggttatt tcatacttcg gttgcatgaa ggcg      54

<210> SEQ ID NO 92
<211> LENGTH: 18
<212> TYPE: PRT
<213> ORGANISM: Artificial Sequence
<220> FEATURE:
<223> OTHER INFORMATION: Amino acid sequnece: Same sequence as SEQ ID
      No. 60 but the "ILFL" sequence of SEQ ID No. 60 has been replaced
      by "FVFV".

<400> SEQUENCE: 92

Met Thr Phe Val Phe Val Thr Met Val Ile Ser Tyr Phe Gly Cys Met
1               5                   10                  15

Lys Ala

<210> SEQ ID NO 93
<211> LENGTH: 54
<212> TYPE: DNA
<213> ORGANISM: Artificial Sequence
<220> FEATURE:
<223> OTHER INFORMATION: Amino acid sequnece: Same sequence as SEQ ID
      No. 61 but the "atccttttcctt" sequence of SEQ ID No. 61 has been
      replaced by "ttcgttttcgtt".

<400> SEQUENCE: 93
atgaccttcg tttcgttac tatggttatt tcatacttcg gttgcatgaa ggcg            54

<210> SEQ ID NO 94
<211> LENGTH: 18
<212> TYPE: PRT
<213> ORGANISM: Artificial Sequence
<220> FEATURE:
<223> OTHER INFORMATION: Amino acid sequnece: Same sequence as SEQ ID
      No. 60 but the "ILFL" sequence of SEQ ID No. 60 has been replaced
      by "FLFV".

<400> SEQUENCE: 94

Met Thr Phe Leu Phe Val Thr Met Val Ile Ser Tyr Phe Gly Cys Met
1               5                   10                  15

Lys Ala

<210> SEQ ID NO 95
<211> LENGTH: 54
<212> TYPE: DNA
<213> ORGANISM: Artificial Sequence
<220> FEATURE:
<223> OTHER INFORMATION: Amino acid sequnece: Same sequence as SEQ ID
      No. 61 but the "atccttttcctt" sequence of SEQ ID No. 61 has been
      replaced by "ttccttttcgtt".

<400> SEQUENCE: 95
atgaccttcc tttcgttac tatggttatt tcatacttcg gttgcatgaa ggcg            54

<210> SEQ ID NO 96
<211> LENGTH: 18
<212> TYPE: PRT
<213> ORGANISM: Artificial Sequence
<220> FEATURE:
<223> OTHER INFORMATION: Amino acid sequnece: Same sequence as SEQ ID
      No. 60 but the "ILFL" sequence of SEQ ID No. 60 has been replaced
      by "FIFV".

<400> SEQUENCE: 96

Met Thr Phe Ile Phe Val Thr Met Val Ile Ser Tyr Phe Gly Cys Met
1               5                   10                  15

Lys Ala

<210> SEQ ID NO 97
<211> LENGTH: 54
<212> TYPE: DNA
<213> ORGANISM: Artificial Sequence
<220> FEATURE:
<223> OTHER INFORMATION: Amino acid sequnece: Same sequence as SEQ ID
      No. 61 but the "atccttttcctt" sequence of SEQ ID No. 61 has been
      replaced by "ttcatcttcgtt".

<400> SEQUENCE: 97
atgaccttca tcttcgttac tatggttatt tcatacttcg gttgcatgaa ggcg         54

<210> SEQ ID NO 98
<211> LENGTH: 18
<212> TYPE: PRT
<213> ORGANISM: Artificial Sequence
<220> FEATURE:
<223> OTHER INFORMATION: Amino acid sequnece: Same sequence as SEQ ID
      No. 60 but the "ILFL" sequence of SEQ ID No. 60 has been replaced
      by "FFFI".

<400> SEQUENCE: 98

Met Thr Phe Phe Phe Ile Thr Met Val Ile Ser Tyr Phe Gly Cys Met
1               5                   10                  15

Lys Ala

<210> SEQ ID NO 99
<211> LENGTH: 54
<212> TYPE: DNA
<213> ORGANISM: Artificial Sequence
<220> FEATURE:
<223> OTHER INFORMATION: Amino acid sequnece: Same sequence as SEQ ID
      No. 61 but the "atcctttcctt" sequence of SEQ ID No. 61 has been
      replaced by "ttcttcttcatc".

<400> SEQUENCE: 99
atgaccttct tcttcatcac tatggttatt tcatacttcg gttgcatgaa ggcg         54

<210> SEQ ID NO 100
<211> LENGTH: 18
<212> TYPE: PRT
<213> ORGANISM: Artificial Sequence
<220> FEATURE:
<223> OTHER INFORMATION: Amino acid sequnece: Same sequence as SEQ ID
      No. 60 but the "ILFL" sequence of SEQ ID No. 60 has been replaced
      by "FFFV".

<400> SEQUENCE: 100

Met Thr Phe Phe Phe Val Thr Met Val Ile Ser Tyr Phe Gly Cys Met
1               5                   10                  15

Lys Ala

<210> SEQ ID NO 101
<211> LENGTH: 54
<212> TYPE: DNA
<213> ORGANISM: Artificial Sequence
<220> FEATURE:
<223> OTHER INFORMATION: Amino acid sequnece: Same sequence as SEQ ID
      No. 61 but the "atcctttcctt" sequence of SEQ ID No. 61 has been
      replaced by "ttcatcctttcctt".

<400> SEQUENCE: 101
atgaccttct tcttcgttac tatggttatt tcatacttcg gttgcatgaa ggcg         54

<210> SEQ ID NO 102
<211> LENGTH: 19
<212> TYPE: PRT
<213> ORGANISM: Artificial Sequence
<220> FEATURE:
<223> OTHER INFORMATION: Amino acid sequnece: Same sequence as SEQ ID
      No. 60 but the "ILFL" sequence of SEQ ID No. 60 has been replaced
      by "FILFL".

<400> SEQUENCE: 102

Met Thr Phe Ile Leu Phe Leu Thr Met Val Ile Ser Tyr Phe Gly Cys 1            5                    10                   15
Met Lys Ala

<210> SEQ ID NO 103
<211> LENGTH: 57
<212> TYPE: DNA
<213> ORGANISM: Artificial Sequence
<220> FEATURE:
<223> OTHER INFORMATION: Amino acid sequnece: Same sequence as SEQ ID
      No. 61 but the "atccttttcctt" sequence of SEQ ID No. 61 has been
      replaced by "ttcttcttcgtt".

<400> SEQUENCE: 103
atgaccttca tccttttcct tactatggtt atttcatact tcggttgcat gaaggcg          57

<210> SEQ ID NO 104
<211> LENGTH: 1203
<212> TYPE: DNA
<213> ORGANISM: Artificial Sequence
<220> FEATURE:
<223> OTHER INFORMATION: Nucleic acid sequence of QTA021P, which is a
      plasmid containing codon optimised sequence for mBDNF-viral-2A
      peptide-eGFP.

<400> SEQUENCE: 104
atgactatcc tgtttctgac aatggttatt agctatttcg gttgcatgaa ggctcacagt        60
gatcccgcac gccgcggaga acttagcgtg tgcgacagca tcagcgagtg ggtcaccgcc      120
gccgataaga gaccgctgt ggatatgtcc ggcgggaccg tcactgtact cgaaaaagtt       180
ccagtgagca aaggccaact gaaacaatat ttctatgaaa ctaagtgcaa ccccatgggg      240
tacaccaagg agggctgccg gggaatcgac aagagacact ggaattccca gtgccggacc      300
actcagagct acgtccgcgc cttgacgatg gattcaaaga gcgcatcgg atggcggttc       360
ataagaatcg acaccagttg tgtgtgcacg ctgacgataa acgggggcg gccccccgtg       420
aagcagaccc tgaactttga tttgctcaag ttggcggggg atgtggaaag caatcccggg      480
ccaatggtga gcaagggcga ggagctgttc accggcgttg tgccaatact ggttgagttg      540
gatggcgatg tcaacggaca caaatttagc gtaagcgggg agggagaggg cgacgccaca      600
tatggcaagc tgaccctgaa gttcatttgc acgaccggca aattgcccgt cccttggccc      660
acacttgtga cgaccctgac ttatggcgta cagtgcttca gcaggtaccc tgatcatatg      720
aagcaacacg acttctttaa gagtgccatg ccagagggat acgtccagga agaaccata       780
ttcttcaaag atgatggaaa ttacaaaacc cgggcagagg tcaagtttga aggcgacacc      840
ctggtgaaca ggatcgaact caaaggcatc gatttcaaag aggacggaaa catcctcgga      900
cacaaactgg aatacaatta caacagccac aacgtctaca tcatggcaga taaacaaaag      960
aacggtatta aagtgaactt caagatccgg cacaacatcg aagacggctc cgtccagctt     1020
gccgaccact accagcaaaa taccccgatc ggcgacggcc ccgttctcct ccccgataat     1080
cactacctga gtacacagtc agccttgagc aaagaccta atgaaaagcg ggaccacatg      1140
gttttgctgg agttcgttac cgcagcgggt attacgctgg gtatggacga gctttacaag     1200
taa                                                                   1203

<210> SEQ ID NO 105
<211> LENGTH: 1203
<212> TYPE: DNA
<213> ORGANISM: Artificial Sequence
<220> FEATURE:
<223> OTHER INFORMATION: Nucleic acid sequence of QTA022P, which is a plasmid containing codon optimised sequence for mBDNF-non-
functional viral-2A peptide-eGFP.

<400> SEQUENCE: 105

```
atgactatcc tgtttctgac aatggttatt agctatttcg gttgcatgaa ggctcacagt      60
gatcccgcac gccgcggaga acttagcgtg tgcgacagca tcagcgagtg ggtcaccgcc     120
gccgataaga agaccgctgt ggatatgtcc ggcgggaccg tcactgtact cgaaaaagtt     180
ccagtgagca aaggccaact gaaacaatat ttctatgaaa ctaagtgcaa ccccatgggg     240
tacaccaagg agggctgccg gggaatcgac aagagacact ggaattccca gtgccggacc     300
actcagagct acgtccgcgc cttgacgatg gattcaaaga gcgcatcgg atggcggttc      360
ataagaatcg acaccagttg tgtgtgcacg ctgacgataa acgggggcg ggcccctgtc      420
aaacaaaccc tcaattttga cttgctgaag cttgctgggg atgtcgagtc cgctgccgcg     480
gctatggtga gcaagggcga ggagctgttc accggcgttg tgccaatact ggttgagttg     540
gatggcgatg tcaacggaca caaatttagc gtaagcgggg agggagaggg cgacgccaca     600
tatggcaagc tgaccctgaa gttcatttgc acgaccggca aattgcccgt cccttggccc     660
acacttgtga cgaccctgac ttatggcgta cagtgcttca gcaggtaccc tgatcatatg     720
aagcaacacg acttctttaa gagtgccatg ccagagggat acgtccagga agaaccata      780
ttcttcaaag atgatggaaa ttacaaaacc cgggcagagg tcaagtttga aggcgacacc     840
ctggtgaaca ggatcgaact caaaggcatc gatttcaaag aggacggaaa catcctcgga     900
cacaaactgg aatacaatta caacagccac aacgtctaca tcatggcaga taaacaaaag     960
aacggtatta aagtgaactt caagatccgg cacaacatcg aagacggctc cgtccagctt    1020
gccgaccact accagcaaaa taccccgatc ggcgacggcc ccgttctcct ccccgataat    1080
cactacctga gtacacagtc agccttgagc aaagacccta tgaaaagcg ggaccacatg     1140
gttttgctgg agttcgttac cgcagcgggt attacgctgg gtatggacga gctttacaag    1200
taa                                                                   1203
```

<210> SEQ ID NO 106
<211> LENGTH: 1203
<212> TYPE: DNA
<213> ORGANISM: Artificial Sequence
<220> FEATURE:
<223> OTHER INFORMATION: Nucleic acid sequence of QTA023P, which is a
plasmid containing codon optimised sequence for eGFP-viral-2A
peptide-mBDNF.

<400> SEQUENCE: 106

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggag acggcaacat cctggggcac      420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
```

| | |
|---|---:|
| tacctgagca cccagtccgc cctgagcaag accccaacg agaagcgcga tcacatggtc | 660 |
| ctgctggagt tcgtgaccgc cgccgggatc actctcggca tggacgagct gtacaaggct | 720 |
| cccgttaaac aaactctgaa cttcgacctg ctgaagctgg ctggagacgt ggagtccaac | 780 |
| cctggaccta tgaccatcct tttccttact atggttattt catacttcgg ttgcatgaag | 840 |
| gcgcactccg accctgcccg ccgtggggag ctgagcgtgt gtgacagtat tagcgagtgg | 900 |
| gtcacagcgg cagataaaaa gactgcagtg gacatgtctg gcgggacggt cacagtccta | 960 |
| gagaaagtcc cggtatccaa aggccaactg aagcagtatt tctacgagac caagtgtaat | 1020 |
| cccatgggtt acaccaagga aggctgcagg ggcatagaca aaaggcactg gaactcgcaa | 1080 |
| tgccgaacta cccaatcgta tgttcgggcc cttactatgg atagcaaaaa gagaattggc | 1140 |
| tggcgattca taaggataga cacttcctgt gtatgtacac tgaccattaa aggggaaga | 1200 |
| tag | 1203 |

<210> SEQ ID NO 107
<211> LENGTH: 2940
<212> TYPE: DNA
<213> ORGANISM: Artificial Sequence
<220> FEATURE:
<223> OTHER INFORMATION: Nucleic acid coding sequence of codon optimised
      2940 bp sequence for murine TrkB receptor-viral-2A peptide-mBDNF
      contained within the plasmid QTA020P (and the vector QTA020V)

<400> SEQUENCE: 107

| | |
|---|---:|
| atgagcccat ggctgaagtg cacggacca gcaatggcaa gactgtgggg cctgtgcctg | 60 |
| ctggtgctgg gcttctggag agccagcctg gcctgtccaa cctcctgcaa gtgtagctcc | 120 |
| gccaggatct ggtgcacaga gccttctcca ggcatcgtgg cctttccccg cctggagcct | 180 |
| aacagcgtga tcccgagaa tatcaccgag atcctgatcg ccaaccagaa gcggctggag | 240 |
| atcatcaatg aggacgatgt ggaggcctac gtgggcctga aaacctgac aatcgtggac | 300 |
| tccggcctga gttcgtggc ctataaggcc tttctgaaga actctaatct gaggcacatc | 360 |
| aacttcaccc gcaataagct gacatctctg agccggagac actttcggca cctggatctg | 420 |
| tccgacctga tcctgaccgg caatccattc acatgctctt gtgacatcat gtggctgaag | 480 |
| accctgcagg agacaaagtc tagccccgat acccaggacc tgtactgtct gaacgagtcc | 540 |
| tctaagaata tgcctctggc caacctgcag atccctaatt gtggactgcc aagcgcccgg | 600 |
| ctggccgcac ctaacctgac agtggaggag ggcaagtccg tgacactgtc ctgttctgtg | 660 |
| ggcggcgatc ccctgcctac cctgtattgg gacgtgggca acctggtgtc taagcacatg | 720 |
| aatgagacct cccacacaca gggctctctg agaatcacaa atatcagctc cgacgatagc | 780 |
| ggcaagcaga tctcttgcgt ggcagagaac ctggtgggag aggatcagga cagcgtgaat | 840 |
| ctgaccgtgc acttcgcccc caccatcaca tttctggagt ctcctaccag cgatcaccac | 900 |
| tggtgcatcc ccttcacagt gcggggaaac ccaaagcccg ccctgcagtg gttttacaac | 960 |
| ggcgccatcc tgaatgagtc caagtatatc tgtaccaaga tccacgtgac caaccacaca | 1020 |
| gagtaccacg gctgcctgca gctggataat cccacccaca tgaacaatgg cgactacaca | 1080 |
| ctgatggcca gaacgagta tggcaaggac gagaggcaga tcagcgccca cttcatgggc | 1140 |
| cgccctggag tggattatga accaaccct aattacccag aggtgctgta tgaggactgg | 1200 |
| accacaccta ccgatatcgg cgacaccaca aacaagtcta atgagatccc aagcacagat | 1260 |
| gtggccgacc agtctaacag ggagcacctg agcgtgtacg cagtggtggt catcgcctcc | 1320 |
| gtggtgggct tctgcctgct ggtcatgctg ctgctgctga agctggcccg ccactctaag | 1380 |

```
tttggcatga agggcccagc ctccgtgatc tctaatgacg atgacagcgc cagcccctg    1440 caccacatca gcaacggctc caataccct tctagctccg agggcggcc agatgccgtg     1500 atcatcggca tgacaaagat ccccgtgatc gagaaccctc agtacttcgg catcaccaat   1560
tcccagctga agcctgacac atttgtgcag cacatcaagc ggcacaacat cgtgctgaag   1620
agggaactgg agagggagc cttcggcaag gtgtttctgg ccgagtgcta taacctgtgc    1680
ccagagcagg ataagatcct ggtggccgtg aagaccctga aggatgccag cgacaacgcc   1740
cggaaggact ccacagaga ggccgagctg ctgacaaatc tgcagcacga gcacatcgtg    1800
aagttttacg gcgtgtgcgt ggagggcgac cctctgatca tggtgttcga gtatatgaag   1860
cacggcgatc tgaacaagtt tctgagagca cacggaccag atgccgtgct gatggcagag   1920
ggaaatcccc ctaccgagct gacacagtct cagatgctgc acattgcaca gcagattgca   1980
gcaggaatgg tgtacctggc cagccagcac ttcgtgcaca gggatctggc aaccagaaac   2040
tgcctggtgg gagagaatct gctggtgaag atcggcgact ttggcatgtc ccgggacgtg   2100
tactctaccg actactatag agtgggcggc cacacaatgc tgcccatcag gtggatgcca   2160
cccgagagca tcatgtatcg caagttcacc acagagtctg acgtgtggag cctgggcgtg   2220
gtgctgtggg agatctttac ctacggcaag cagccttggt atcagctgtc caacaatgaa   2280
gtgatcgagt gtattacaca gggacgcgtg ctgcagaggc cacgcacatg cccccaggag   2340
gtgtacgagc tgatgctggg ctgttggcag cgggagccac acaccagaaa gaacatcaag   2400
agcatccaca cactgctgca gaatctggcc aaggcctccc ccgtgtatct ggacatcctg   2460
ggcagcggag ctactaactt cagcctgctg aagcaggctg agacgtgga ggagaaccct    2520 ggacctatga gaatccttct tcttactatg gttatttcat acttcggttg catgaaggcg   2580
cactccgacc ctgcccgccg tggggagctg agcgtgtgtg acagtattag cgagtgggtc   2640
acagcggcag ataaaaagac tgcagtggac atgtctggcg ggacggtcac agtcctagag   2700
aaagtcccgg tatccaaagg ccaactgaag cagtatttct acgagaccaa gtgtaatccc   2760
atgggttaca ccaaggaagg ctgcaggggc atagacaaaa ggcactggaa ctcgcaatgc   2820
cgaactaccc aatcgtatgt cgggcccctt actatggata gcaaaagag aattggctgg    2880 cgattcataa ggatagacac ttcctgtgta tgtacactga ccattaaaag gggaagatag   2940
```

<210> SEQ ID NO 108
<211> LENGTH: 2943
<212> TYPE: DNA
<213> ORGANISM: Artificial Sequence
<220> FEATURE:
<223> OTHER INFORMATION: Nucleic acid coding sequence of codon optimised 2943 bp sequence for human TrkB receptor-viral-2A peptide-mBDNF contained within the plasmid QTA029P (and the vector QTA029V)

<400> SEQUENCE: 108

```
atgtcatctt ggatccgctg gcacgggcca gcgatggccc gattgtgggg cttctgctgg    60
cttgttgtag gcttctggcg cgcggcgttc gcgtgtccga cctcttgcaa atgctcagca   120
agccgaattt ggtgctcaga ccctagtcca ggaattgttg cattccccg actggaacca    180 aactccgtcg acccggagaa tataactgag atatttattg caaatcaaaa acgccttgaa   240
atcattaacg aggatgacgt ggaggcctac gttggtttga gaaatcttac tattgtcgac   300
tccggactta aatttgtagc tcataaagcc ttcctgaaga actctaatct gcagcacatt   360
aatttcacga gaaataagct gaccagcttg tcccggaagc atttccgcca tctcgacctg   420
```

-continued

| | | | | | |
|---|---|---|---|---|---|
| agcgagctca | tactggtcgg | aaacccattt | acgtgctcct | gtgacatcat | gtggatcaaa | 480 |
| actctgcaag | aggcgaaaag | tagtccggat | acccaagacc | tttactgtct | taatgaaagc | 540 |
| tcaaaaaata | tcccgctggc | caacctgcag | ataccgaact | gcggacttcc | tagtgcgaat | 600 |
| ttggctgccc | caaatcttac | cgtcgaagaa | ggcaaatcaa | tcacgctttc | ttgttctgta | 660 |
| gctggagatc | cagtgcctaa | tatgtattgg | gacgtgggta | acctcgtctc | aaaacatatg | 720 |
| aacgaaacga | gccacaccca | gggctctttg | cggataacaa | acatctcctc | tgatgattct | 780 |
| ggaaagcaaa | tcagttgcgt | agctgaaaat | ctggttggcg | aagatcaaga | ttcagtcaat | 840 |
| ctgacagtcc | atttcgcccc | aacgatcacc | tttctggaga | gcccaactag | cgatcaccac | 900 |
| tggtgtattc | cgtttacggt | aaaaggaaat | ccaaaacctg | cactccaatg | gttttataat | 960 |
| ggagccatct | tgaatgaaag | caaatatatc | tgtactaaaa | tccatgtgac | gaatcacacc | 1020 |
| gagtatcacg | ggtgtcttca | attggataat | ccaacccata | tgaataatgg | tgattatact | 1080 |
| ttgatagcga | agaacgaata | cggcaaagac | gaaaagcaaa | tatccgcaca | tttcatgggt | 1140 |
| tggcctggca | tcgacgacgg | tgcgaacccg | aactacccag | atgttattta | cgaggattat | 1200 |
| gggactgcgg | caaacgacat | tggcgacacc | acaaaccgaa | gcaacgagat | accaagtact | 1260 |
| gacgtcactg | acaaaacggg | tcgagagcat | ttgtctgttt | acgccgttgt | tgttatcgcc | 1320 |
| tcagttgtcg | gattttgcct | gttggtcatg | cttttcctcc | tgaagctcgc | gcgacattcc | 1380 |
| aagtttggca | tgaaggggcc | agcaagtgtt | atatccaatg | atgatgatag | cgcttctcca | 1440 |
| ttgcaccaca | taagtaacgg | ctcaaacacg | ccgtcatcta | gtgaaggtgg | accagacgcg | 1500 |
| gtcattatag | ggatgactaa | aattcccgta | atcgaaaacc | ctcagtactt | cggcataacc | 1560 |
| aacagtcagc | ttaaacccga | tactttcgtg | cagcacatca | aaaggcacaa | catagtcctc | 1620 |
| aagcgcgaac | tcggggaggg | agccttcgga | aaggtctttc | ttgctgagtg | ctataatttg | 1680 |
| tgtcctgagc | aggataaaat | tcttgtggct | gtaaaaactc | tcaaagatgc | ttccgacaac | 1740 |
| gcacggaagg | attttcatcg | ggaggccgaa | ctgttgacga | atttgcagca | cgagcatata | 1800 |
| gtaaagttct | acggggtatg | tgttgagggg | gacccgttga | ttatggtctt | cgagtatatg | 1860 |
| aagcacgggg | acctgaacaa | attttttgcgc | gcccatgggc | ctgatgccgt | ccttatggca | 1920 |
| gaagggaacc | ctccaacaga | actcacccag | agtcagatgt | tgcacatagc | gcaacagatc | 1980 |
| gcggccggca | tggtttacct | ggccagtcaa | cacttcgtgc | atagagatct | tgccactcgc | 2040 |
| aactgtttgg | tcggggagaa | ccttctggtt | aagattggtg | actttggtat | gtcacgagat | 2100 |
| gtgtattcca | ctgactatta | cagagttggg | ggtcatacaa | tgcttcctat | cggtggatg | 2160 |
| ccccccgaat | ccatcatgta | cagaaagttc | acgacagaga | gtgatgtttg | gagtctcggc | 2220 |
| gtggtgctct | gggaaatttt | cacatacgga | aagcagccgt | ggtatcaact | tagcaacaat | 2280 |
| gaggtgatag | agtgtattac | acagggtcgg | gtgttgcagc | gccctcgaac | gtgcccacaa | 2340 |
| gaagtatatg | aacttatgct | cggggtgctgg | caaagagaac | cacatatgag | aaaaaatatc | 2400 |
| aagggatac | atacattgct | tcagaacttg | gccaaggcat | cacccgtcta | cctcgatata | 2460 |
| ctgggcagcg | gagctactaa | cttcagcctg | ctgaagcagg | ctggagacgt | ggaggagaac | 2520 |
| cctggaccta | tgagaatcct | tcttcttact | atggttattt | catacttcgg | ttgcatgaag | 2580 |
| gcgcactccg | accctgcccg | ccgtggggag | ctgagcgtgt | gtgacagtat | tagcgagtgg | 2640 |
| gtcacagcgg | cagataaaaa | gactgcagtg | gacatgtctg | gcgggacggt | cacagtccta | 2700 |
| gagaaagtcc | cggtatccaa | aggccaactg | aagcagtatt | tctacgagac | caagtgtaat | 2760 |
| cccatggggtt | acaccaagga | aggctgcagg | ggcatagaca | aaaggcactg | gaactcgcaa | 2820 |

```
tgccgaacta cccaatcgta tgttcgggcc cttactatgg atagcaaaaa gagaattggc    2880
tggcgattca taaggataga cacttcctgt gtatgtacac tgaccattaa aaggggaaga    2940
tag                                                                  2943
```

The invention claimed is:

1. A genetic construct comprising a promoter operably linked to a first coding sequence, which encodes the tyrosine kinase receptor B (TrkB), and a second coding sequence, which encodes an agonist of the TrkB receptor, wherein the agonist is mature BDNF and wherein the genetic construct comprises a spacer sequence disposed between the first and second coding sequences, which spacer sequence encodes a peptide spacer that is configured to be digested to thereby produce the TrkB receptor and agonist as separate molecules.

2. A genetic construct according to claim 1, wherein the promoter is the human synapsin I (SYN I) promoter or the CAG promoter.

3. A genetic construct according to claim 1, wherein the spacer sequence comprises and encodes a viral peptide spacer sequence.

4. A genetic construct according to claim 1, wherein the peptide spacer sequence comprises an amino acid sequence substantially as set out in SEQ ID NO. 4, or a fragment or variant thereof; or (ii) an amino acid sequence substantially as set out in SEQ ID NO. 6, or a fragment or variant thereof; or (iii) an amino acid sequence substantially as set out in SEQ ID NO. 8, or a fragment or variant thereof.

5. A genetic construct according to claim 1, wherein the spacer sequence comprises: (i) a nucleotide sequence substantially as set out in SEQ ID NO. 5, or a fragment or variant thereof; or (ii) a nucleotide sequence substantially as set out in SEQ ID NO. 7, or a fragment or variant thereof.

6. A genetic construct according to claim 1, wherein the first coding sequence comprises a nucleotide sequence encoding the human canonical isoform of TrkB comprising an amino acid sequence substantially as set out in SEQ ID NO. 9, or a fragment or variant thereof, and/or wherein the first coding sequence comprises a nucleotide sequence substantially as set out in SEQ ID NO. 10, or a fragment or variant thereof.

7. A genetic construct according to claim 1, wherein the first coding sequence comprises a nucleotide sequence which encodes isoform 4 of TrkB, and (i) wherein isoform 4 of TrkB comprises an amino acid sequence substantially as set out in SEQ ID NO. 11, or a fragment or variant thereof, and/or (ii) wherein the first coding sequence comprises a nucleotide sequence substantially as set out in SEQ ID NO. 12, or a fragment or variant thereof.

8. A genetic construct according to claim 1, wherein the first coding sequence comprises a nucleotide sequence encoding a mutant form of TrkB receptor, wherein one or more tyrosine residue at position 516, 701, 705, 706 and/or 816 of SEQ ID No: 9 is modified or mutated, and/or wherein at least two, three or four tyrosine residues at position 516, 701, 705, 706 and/or 816 of SEQ ID No: 9 are modified, and/or wherein all five tyrosine residues at position 516, 701, 705, 706 and/or 816 of SEQ ID No: 9 are modified, and/or wherein the or each tyrosine residue is modified to a glutamic acid.

9. A genetic construct according to claim 8, wherein the modified form of the TrkB receptor comprises an amino acid sequence substantially as set out in SEQ ID NO. 13, or a fragment or variant thereof, and/or wherein the first coding sequence comprises a nucleotide sequence substantially as set out in SEQ ID NO. 14, or a fragment or variant thereof.

10. A genetic construct according to claim 1, wherein the second coding sequence comprises a nucleotide sequence which encodes mature BDNF, and/or wherein mature BDNF comprises an amino acid sequence substantially as set out in SEQ ID NO. 18, or a fragment or variant thereof, and/or wherein the second coding sequence comprises a nucleotide sequence substantially as set out in SEQ ID NO. 19, or a fragment or variant thereof.

11. A genetic construct according to claim 1, wherein the second coding sequence comprises a nucleotide sequence encoding a signal peptide for the agonist of the TrkB receptor.

12. A genetic construct according to claim 11, wherein the second coding sequence comprises a nucleotide sequence which encodes a signal peptide comprising an amino acid sequence substantially as set out in SEQ ID NO. 20, or a fragment or variant thereof, and/or wherein the second coding sequence comprises a nucleotide sequence substantially as set out in SEQ ID NO. 21, or a fragment or variant thereof.

13. A genetic construct according to claim 1, wherein the second coding sequence comprises a nucleotide sequence encoding a signal sequence peptide substantially as set out in any one of SEQ ID NO. 23, 25, 27 or 29, or wherein the signal peptide comprises an amino acid sequence substantially as set out in any one of SEQ ID NO. 22, 24, 26 or 28, and/or wherein the second coding sequence comprises a nucleotide sequence encoding a signal sequence peptide substantially as set out in any one of SEQ ID NO. 31, 33, 35, 37, 39, 41, 43, 45, 61, 63, 65, 67, 69, 71, 73, 75, 77, 79, 81, 83, 85, 87, 89, 91, 93, 95, 97, 99, 101 or 103; or wherein the signal peptide comprises an amino acid sequence substantially as set out in any one of SEQ ID NO. 30, 32, 34, 36, 38, 40, 42, 44, 60, 62, 64, 66, 68, 70, 72, 74, 76, 78, 80, 82, 84, 86, 88, 90, 92, 94, 96, 98, 100 or 102.

14. A genetic construct according to claim 1, wherein the construct comprises a nucleotide sequence substantially as set out in SEQ ID No: 107 or 108, or a fragment or variant thereof.

15. A recombinant vector comprising the genetic construct according to claim 1, wherein the vector is a recombinant AAV (rAAV) vector, optionally wherein the rAAV is AAV-1, AAV-2, AAV-3A, AAV-3B, AAV-4, AAV-5, AAV-6, AAV-7, AAV-8, AAV-9, AAV-10 or AAV-11.

16. A pharmaceutical composition comprising the genetic construct according to claim 1, and a pharmaceutically acceptable vehicle.

17. A method of treating, preventing or ameliorating an optic nerve disorder or a cochlear disorder in a subject, or for promoting nerve regeneration and/or survival in a subject, the method comprising administering, to a subject in need of such treatment, a therapeutically effective amount of the genetic construct according to claim 1.

18. The method according to claim 17, wherein the optic nerve disorder that is treated is any pathophysiological condition which results in loss of RGCs, optionally wherein the optic nerve disorder that is treated is glaucoma, or wherein the cochlear disorder which is treated is hearing loss or deafness.

19. A genetic construct according to claim 3, wherein the viral peptide spacer sequence is a viral 2A peptide spacer sequence.

20. A genetic construct according to claim 11, wherein signal peptide for BDNF, optionally wherein the nucleotide sequence encodes the canonical signal peptide for BDNF.

21. The method according to claim 18, wherein the pathophysiological condition is trauma to the head or face or vascular insult.

\* \* \* \* \*

UNITED STATES PATENT AND TRADEMARK OFFICE
CERTIFICATE OF CORRECTION

PATENT NO. : 11,471,539 B2
APPLICATION NO. : 16/436676
DATED : October 18, 2022
INVENTOR(S) : Peter Widdowson et al.

It is certified that error appears in the above-identified patent and that said Letters Patent is hereby corrected as shown below:

In the Specification

In Column 22, Line 11, please change "lot" to ---101---;

In the Claims

In Column 125, Line 11, please change "signal peptide" to ---the signal peptide is a signal peptide---.

Signed and Sealed this
Twenty-seventh Day of December, 2022

Katherine Kelly Vidal
*Director of the United States Patent and Trademark Office*